(12) United States Patent
Schottek et al.

(10) Patent No.: US 7,569,651 B2
(45) Date of Patent: Aug. 4, 2009

(54) TRANSITION METAL COMPOUND, LIGAND SYSTEM, CATALYST SYSTEM AND ITS USE FOR THE POLYMERIZATION AND COPOLYMERIZATION OF OLEFINS

(75) Inventors: Jörg Schottek, Frankfurt (DE); Markus Oberhoff, Soeyer (DE); Carsten Bingel, Kriftel (DE); David Fischer, Breunigweiler (DE); Horst Weiβ, Neuhofen (DE); Andreas Winter, Neuleiningen (DE); Volker Fraaije, Frankfurt (DE); Ralph-Dieter Maier, Hoergertshausen (DE); Wolfgang Bidell, Mannheim (DE); Nicola Paczkowski, Dirmstein (DE); Jürgen Suhm, Worms-Weinsheim (DE); Roland Kratzer, Hofheim (DE)

(73) Assignee: Basell Polypropylen GmbH, Mainz (DE)

( * ) Notice: Subject to any disclaimer, the term of this patent is extended or adjusted under 35 U.S.C. 154(b) by 299 days.

(21) Appl. No.: 11/131,251

(22) Filed: May 18, 2005

(65) Prior Publication Data

US 2006/0020096 A1    Jan. 26, 2006

Related U.S. Application Data

(62) Division of application No. 10/168,952, filed as application No. PCT/EP00/12642 on Dec. 13, 2000, now Pat. No. 7,342,078.

(30) Foreign Application Priority Data

Dec. 23, 1999  (DE)  ................................. 199 62 905
Sep. 11, 2000  (DE)  ................................. 100 44 983

(51) Int. Cl.
*C08F 4/6592*  (2006.01)
*C08F 210/06*  (2006.01)
*C08F 210/16*  (2006.01)
*C08L 23/14*  (2006.01)

(52) U.S. Cl. .................. 526/348; 526/127; 526/160; 526/170; 525/240

(58) Field of Classification Search ................ 525/240; 526/127, 160, 170, 348

See application file for complete search history.

(56) References Cited

U.S. PATENT DOCUMENTS

| | | | |
|---|---|---|---|
| 4,752,597 A | 6/1988 | Turner | 502/104 |
| 5,017,714 A | 5/1991 | Welborn, Jr. | 556/12 |
| 5,103,030 A | 4/1992 | Rohrmann et al. | 556/12 |
| 5,304,614 A | 4/1994 | Winter et al. | 526/127 |
| 5,414,064 A | 5/1995 | Lux et al. | 526/215 |
| 5,532,396 A | 7/1996 | Winter et al. | 556/11 |
| 5,543,535 A | 8/1996 | Lisowsky | 556/11 |
| 5,565,534 A | 10/1996 | Aulbach et al. | 526/160 |
| 5,612,462 A | 3/1997 | Lisowsky | 534/15 |
| 5,661,096 A | 8/1997 | Winter et al. | 502/103 |
| 5,770,753 A | 6/1998 | Küber et al. | 556/11 |
| 5,786,432 A | 7/1998 | Küber et al. | 526/127 |
| 5,840,644 A | 11/1998 | Küber et al. | 502/117 |
| 6,017,841 A | 1/2000 | Winter et al. | 502/103 |
| 6,051,727 A | 4/2000 | Küber et al. | 556/11 |
| 6,121,182 A | 9/2000 | Okumura et al. | 502/152 |
| 6,124,231 A | 9/2000 | Fritze et al. | 502/152 |
| 6,172,168 B1 | 1/2001 | Winter et al. | 526/127 |
| 6,242,544 B1 | 6/2001 | Küber et al. | 526/127 |
| 6,255,506 B1 | 7/2001 | Küber et al. | 556/11 |
| 6,255,531 B1 | 7/2001 | Fritz et al. | 568/3 |
| 6,271,164 B1 | 8/2001 | Fritze et al. | 502/104 |
| 6,329,313 B1 | 12/2001 | Fritze et al. | 502/202 |
| 6,350,829 B1 | 2/2002 | Lynch et al. | 526/151 |
| 6,365,689 B1 * | 4/2002 | Ushioda et al. | 526/160 |
| 6,417,302 B1 | 7/2002 | Bohnen | 526/160 |
| 6,444,606 B1 | 9/2002 | Bingel et al. | 502/152 |
| 6,469,114 B1 | 10/2002 | Schottek et al. | 526/127 |
| 6,482,902 B1 | 11/2002 | Bohnen et al. | 526/127 |
| 6,492,539 B1 | 12/2002 | Bingel et al. | 556/11 |
| 6,509,324 B1 | 1/2003 | Franzini et al. | 514/102 |
| 6,583,238 B1 | 6/2003 | Göres et al. | 526/127 |
| 6,924,248 B2 | 8/2005 | Mihan et al. | 502/132 |
| 7,094,727 B2 | 8/2006 | Hwang et al. | 502/150 |

FOREIGN PATENT DOCUMENTS

| | | |
|---|---|---|
| DE | 196 06 167 | 8/1997 |
| DE | 196 22 207 | 12/1997 |
| DE | 198 04 970 | 8/1999 |
| DE | 198 13 657 | 9/1999 |
| EP | 0 129 368 | 12/1984 |

(Continued)

OTHER PUBLICATIONS

Wild, "*Temperature Rising Elution Fractionation*", Advances in Polymer Science, Sprin ger Verlag 1990, pp. 1-47.
Ewen et al., "*Expanding the Sope of Metallocene Catalysis: Beyong Indenyl and furenyl Derivatives*" Metalorganic Catalysts for Synthesis and polymerization (1999), pp. 1150-1169.
Pasynkiewics, "*Alumoxanes: Synthesis, Structures, Complexes and Reactions*", Polyhedron 9(2/3), 429-453 (1990).

(Continued)

*Primary Examiner*—Roberto Rábago
(74) *Attorney, Agent, or Firm*—Novak Druce + Quigg LLP

(57) ABSTRACT

A process for the polymerization of olefins, in particular a process for the copolymerization of propylene with further olefins, is carried out in the presence of highly active catalyst systems comprising specifically selected metallocenes, in particular ones which bear different substituents in position 2 and position 4 on an indenyl ligand. Novel polypropylene copolymers can be obtained by this process.

16 Claims, No Drawings

FOREIGN PATENT DOCUMENTS

| | | |
|---|---|---|
| EP | 0 302 424 | 2/1989 |
| EP | 0 320 762 | 6/1989 |
| EP | 0 416 815 | 3/1991 |
| EP | 0 537 686 | 4/1993 |
| EP | 0 576 970 | 1/1994 |
| EP | 0 601 830 | 6/1994 |
| EP | 0 659 757 | 6/1995 |
| EP | 0 669 340 | 8/1995 |
| EP | 0 754 731 | 1/1997 |
| EP | 0 811 627 | 12/1997 |
| EP | 0 824 112 | 2/1998 |
| EP | 0 824 113 | 2/1998 |
| EP | 0 834 519 | 4/1998 |
| EP | 0 924 223 | 6/1999 |
| WO | WO 97/11775 | 4/1997 |
| WO | WO 98/40331 | 3/1998 |
| WO | WO 98/40416 | 9/1998 |
| WO | WO 99/06414 | 2/1999 |
| WO | WO 99/09079 * | 2/1999 |
| WO | WO 99/40129 | 8/1999 |
| WO | WO 00/44799 | 8/2000 |
| WO | WO 01/46274 | 6/2001 |
| WO | WO 01/96418 | 12/2001 |

OTHER PUBLICATIONS

Harlan et al., "tert-*Butylaluminum Hydroxides and Oxides: Structural Relationship between Alkylalumoxanes and Alumina Gels*", Organomet. 13, 2957-2969 (1994).

Harlan et al., "*Three-Coordinate Aluminum Is Not a Prerequisite for Catalytic Activity in the Zircocene-Alumoxane Polymerization of Ethylene*" J. Am. Chem. Soc. 117, 6465-6474 (1995).

Wild et al., "ansa-*Metallocene Derivatives: Synthesis and Crystal Structure of a Chiral* ansa-*Zircocene Derivative . . .* " J. Organomet. Chem. 288, 63-67 (1985).

Spaleck et al., "*New Bridged Zircocenes for Olefin Polymerization: Binuclear and Hybrid Structures*" J. Molec. Cat. A: Chem. 128, 279-287 (1998).

Wild et al., "ansa-*Metallocene Derivatives: Synthesis and Molecular Structures of Chiral* ansa-*Titanocene Derivatives . . .* " J. Organomet. Chem. 232, 233-247 (1982).

Brintzinger et al., "*Stereospezifische Olefinpolymerisation mit chiralen Metallocenkatalysatoren*" Angew. Chem. 107, 1255-1283 (1995).

* cited by examiner

TRANSITION METAL COMPOUND, LIGAND SYSTEM, CATALYST SYSTEM AND ITS USE FOR THE POLYMERIZATION AND COPOLYMERIZATION OF OLEFINS

This is a Divisional application of application Ser. No. 10/168,952, filed on Jun. 24, 2002 now U.S. Pat. No. 7,342,078, the entire disclosure of which is herewith incorporated by reference, which is a U.S. national stage application under 35 U.S.C. § 371, based on international application No. PCT/EP 00/12642, filed Dec. 13, 2000.

Transition metal compound, ligand system, catalyst system and its use for the polymerization and copolymerization of olefins The present invention relates to a process for the polymerization of olefins, in particular a process for the copolymerization of propylene with further olefins, to specifically substituted metallocenes, to ligand systems and to highly active catalyst systems.

Processes for preparing polyolefins with the aid of soluble, homogeneous catalyst systems comprising a transition metal component of the metallocene type and a cocatalyst component such as an aluminoxane, a Lewis acid or an ionic compound are known. These catalysts have a high activity and give polymers and copolymers having a narrow molar mass distribution.

In polymerization processes using soluble, homogeneous catalyst systems, heavy deposits are formed on reactor walls and stirrer if the polymer is obtained as a solid. These deposits are formed by agglomeration of the polymer particles whenever metallocene and/or cocatalyst are present in dissolved form in the suspension. Such deposits in the reactor systems have to be removed regularly, since they quickly reach considerable thicknesses, have a high strength and prevent heat exchange with the cooling medium. Such homogeneous catalyst systems cannot be used in modern industrial polymerization processes in liquid monomer or in the gas phase.

To avoid deposit formation in the reactor, supported catalyst systems in which the metallocene and/or the aluminum compound serving as cocatalyst are fixed to an inorganic support material have been proposed.

Metallocenes can, if appropriate in combination with one or more cocatalysts, be used as catalyst components for the polymerization and copolymerization of olefins. In particular, halogen-containing metallocenes are used as catalyst precursors which can be converted, for example, by means of an aluminoxane into a polymerization-active cationic metallocene complex (EP-A-129368).

The preparation of metallocenes is known per se (U.S. Pat. No. 4,752,597; U.S. Pat. No. 5,017,714; EP-A-320762; EP-A-416815; EP-A-537686; EP-A-669340; H. H. Brintzinger et al.; Angew. Chem., 107 (1995), 1255; H. H. Brintzinger et al., J. Organomet. Chem. 232 (1982), 233. For this purpose, it is possible, for example, to react cyclopentadienylmetal compounds with halides of transition metals such as titanium, zirconium and hafnium.

EP 576 970 A1 discloses metallocenes and corresponding, supported catalyst systems.

The supported catalyst systems give, at industrially relevant polymerization temperatures of 50-80° C., polymers, in particular polypropylenes, having melting points of not more than 156° C.; typical values for such systems are merely in the region around 150° C.

In the field of copolymerization, copolymers having low molar masses or low levels of ethene incorporation are usually obtained. In this area, it would be desirable to have a high molar mass and a high degree of ethene incorporation without adverse effect on the molar mass of the copolymer and also an increase in the molar mass of the resulting copolymer compared to the molar mass of the homopolymer.

EP-A-659757, Spaleck et al., J. Mol. Catal. A: Chemical 1998, 128, 279-287 and EP-A-834519 describe metallocene compounds containing two differently substituted indenyl ligands. It is found that the metallocene compounds described there give very low molecular weight copolymers in the copolymerization of, for example, ethylene and propylene. In addition, the ethene content of the copolymer is low. The systems described there additionally suffer from a considerable decrease in molar mass compared to the corresponding homopolymer. The incorporation of ethene appears to lead to a greater number of termination reactions. In addition to this observation, the polymerization activity in a heterogeneous polymerization is low compared to that in a homogeneneous polymerization. This leads to restricted commercial utilization.

For many polymer applications, for example in the fields of extrusion and injection molding, such products are not yet satisfactory in terms of hardness or mechanical strength. In the preparation of copolymers, these metallocenes and catalyst systems generally produce copolymers whose achievable molar masses decrease steadily with increasing comonomer content. Particularly in the area of block copolymer production or reactor blend production, this behavior is a disadvantage, since a high molar mass is wanted to achieve a high hardness/impact toughness of the desired copolymer or terpolymer fraction.

It is an object of the present invention to find supported metallocene catalysts which avoid the disadvantages of the prior art and, in particular, give copolymers having a high molar mass and a high degree of ethene incorporation under industrially relevant polymerization conditions as a result of their high regiospecificity and stereospecificity. In addition, these metallocenes should display a significantly increased polymerization activity in a heterogeneous polymerization and provide an environmentally friendly and economical process for preparing the polymers.

We have found that this object is achieved by a process for the polymerization of olefins, in particular for the coolymerization of propylene with at least one further olefin, in which the polymerization is carried out in the presence of a catalyst system comprising at least one specifically substituted metallocene, at least one cocatalyst, if desired a passivated support and, if desired, at least one further additive component.

The metallocene used in the process of the present invention is a compound of the formula (I)

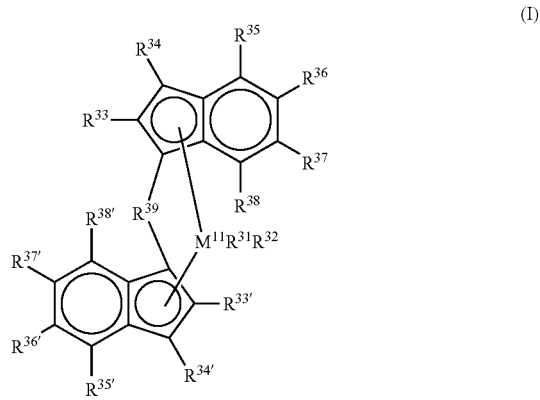

(I)

where $M^{11}$ is a metal of group IVb of the Periodic Table of the Elements, $R^{31}$, $R^{32}$ are identical or different and are each a hydrogen atom, a $C_1$-$C_{10}$-alkyl group, a $C_1$-$C_{10}$-alkoxy group, a $C_6$-$C_{20}$-aryl group, a $C_6$-$C_{10}$-aryloxy group, a $C_2$-$C_{10}$-alkenyl group, an OH group, an $N(R^{32})_2$ group, where $R^{32}$ is a $C_1$-$C_{10}$-alkyl group or a $C_6$-$C_{14}$-aryl group, or a halogen atom, where $R^{31}$ and $R^{32}$ can also be joined to form a ring, $R^{34}$, $R^{36}$, $R^{37}$ and $R^{38}$ and also $R^{34'}$, $R^{36'}$, $R^{37'}$ and $R^{38'}$ are identical or different and are each a hydrogen atom or a hydrocarbon group which may be halogenated, linear, cyclic or branched, e.g. a $C_1$-$C_{10}$-alkyl group, a $C_2$-$C_{10}$-alkenyl group, a $C_6$-$C_{20}$-aryl group, a $C_7$-$C_{40}$-arylalkyl group, a $C_7$-$C_{40}$-alkylaryl group or a $C_8$-$C_{40}$-arylalkenyl group, $R^{33}$ and $R^{33'}$ are identical or different, where $R^{33}$ is as defined for $R^{33'}$ or is a hydrocarbon group which is unbranched in the α position and may be halogenated, e.g. a $C_1$-$C_{20}$-alkyl group, a $C_2$-$C_{20}$-alkenyl group, a $C_7$-$C_{40}$-alkylaryl group or a $C_8$-$C_{40}$-alkenylaryl group, $R^{33'}$ is a hydrocarbon group which is cyclized in the α position or branched in the α position and may be halogenated, e.g. a $C_3$-$C_{20}$-alkyl group, a $C_3$-$C_{20}$-alkenyl group, a $C_6$-$C_{20}$-aryl group, a $C_7$-$C_{40}$-arylalkyl group, a $C_7$-$C_{40}$-alkylaryl group or a $C_8$-$C_{40}$-arylalkenyl group, $R^{35}$, $R^{35'}$ are identical or different and are each a $C_6$-$C_{20}$-aryl group which in the para position relative to the point of linkage to the indenyl ring bears a substituent $R^{43}$ or $R^{43'}$,

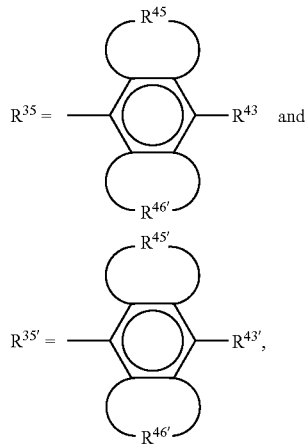

$R^{35}$ and $R^{35'}$ may not be the combinations of phenyl and 1-naphthyl or 1-naphthyl and phenyl when $R^{33}$ is methyl or ethyl and $R^{33'}$ is isopropyl, $R^{39}$ is a bridge:

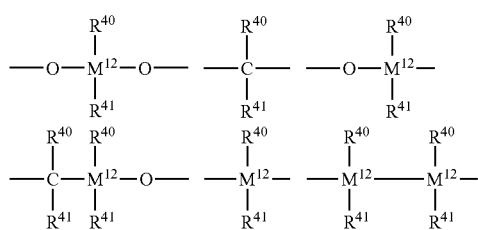

-continued

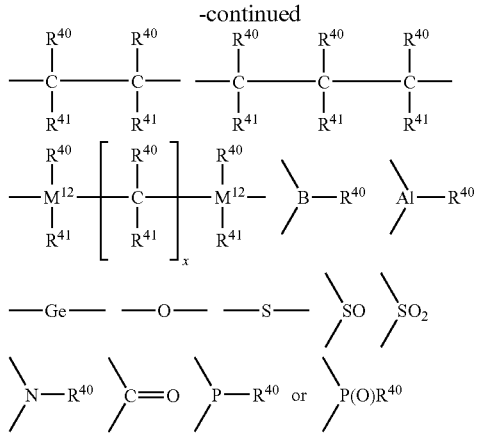

$R^{40}$, $R^{41}$ can be identical or different, even when they have the same index, and are each a hydrogen atom, a halogen atom or a $C_1$-$C_{40}$ group such as a $C_1$-$C_{20}$-alkyl group, a $C_1$-$C_{10}$-fluoroalkyl group, a $C_1$-$C_{10}$-alkoxy group, a $C_6$-$C_{14}$-aryl group, a $C_6$-$C_{10}$-fluoroaryl group, a $C_6$-$C_{10}$-aryloxy group, a $C_2$-$C_{10}$-alkenyl group, a $C_7$-$C_{40}$-arylalkyl group, a $C_7$-$C_{40}$-alkylaryl group or a $C_8$-$C_{40}$-arylalkenyl group, where $R^{40}$ and $R^{41}$ may each, together with the atoms connecting them, form one or more rings, and x is an integer from zero to 18, $M^{12}$ is silicon, germanium or tin, $R^{39}$ may also link two units of the formula I with one another, $R^{43}$ can be a hydrogen atom if $R^{35}$ is different from $R^{35'}$, or a $C_1$-$C_{20}$-alkyl radical, a $C_2C_{10}$-alkenyl radical, a $C_6$-$C_{18}$-aryl radical, a $C_7$-$C_{20}$-arylalkyl radical, a $C_7$-$C_{20}$alkylaryl radical, a $C_8$-$C_{20}$-arylalkenyl radical, where the hydrocarbon radicals may also be halogenated or partially halogenated by fluorine or chlorine, and be $-N(R^{44})_2$, $-P(R^{44})_2$, $-SR^{44}$, $-Si(R^{44})_3$, $-[N(R^{44})_3]^+$ or $-[P(R^{44})_3]^+$, where the radicals $R^{44}$ are identical or different and are each a hydrogen atom or a hydrocarbon group which may be halogenated, linear, cyclic or branched, e.g. a $C_1$-$C_{10}$-alkyl group, a $C_2$-$C_{10}$-alkenyl group, a $C_6$-$C_{20}$-aryl group, a $C_1C_{40}$arylalkyl group, a $C_7$-$C_{40}$-alkylaryl group or a $C_8$-$C_{40}$-arylalkenyl group, $R^{43'}$ is hydrogen or is as defined for $R^{43}$, $R^{45}$, $R^{45'}$, $R^{46}$ and $R^{46'}$ are each hydrogen or $C_4$-$C_{20}$-aryl, alkenyl or alkyl ring systems which may also be linked to the radicals $R^{36}$, $R^{36'}$ or $R^{34}$, $R^{34'}$.

The 4,5,6,7-tetrahydroindenyl analogs corresponding to the compounds I are likewise of importance.

In formula (I), it is preferred that $M^{11}$ is zirconium or hafnium, $R^{31}$ and $R^{32}$ are identical or different and are each a $C_1$-$C_{10}$-alkyl group, a $C_1$-$C_{10}$-alkoxy group, a $C_6$-$C_{10}$-aryloxy group or a halogen atom, where $R^{31}$ and $R^{32}$ may also be joined to form a ring, $R^{33}$, $R^{33'}$ are different, $R^{33}$ is a linear $C_1$-$C_{10}$-alkyl group or a linear $C_2$-$C_{10}$-alkenyl group, $R^{33'}$ is a hydrocarbon group which is cyclized in the α position or branched in the α position and in which the atom in the α position is bound to a total of three carbon atoms, e.g. a $C_3$-$C_{10}$-alkyl group, a $C_3$-$C_{10}$-alkenyl group, a $C_6$-$C_{14}$-aryl group, a $C_7$-$C_{15}$-arylalkyl group, a $C_7$-$C_{15}$-alkylaryl group or a $C_8$-$C_{16}$-arylalkenyl group, $R^{34}$, $R^{36}$, $R^{37}$ and $R^{38}$ and also $R^{34'}$, $R^{36'}$, $R^{37'}$ and $R^{38'}$ are identical or different and are each a hydrogen atom or a $C_1$-$C_{10}$-alkyl group which may be halogenated, linear, cyclic or branched, $R^{39}$ is $R^{40}R^{41}Si=$, $R^{40}R^{41}Ge=$, $R^{40}R^{41}C=$ or $—(R^{40}R^{41}C—CR^{40}R^{41})—$, where $R^{40}$ and $R^{41}$ are identical or different and are each hydrogen or a $C_1$-$C_{20}$-hydrocarbon group, in particular $C_1$-$C_{10}$-alkyl or $C_6$-$C_{14}$-aryl, $R^{35}$, $R^{35'}$ are identical or different and are each a $C_6$-$C_{20}$-aryl group which in the para position relative to the point of linkage to the indenyl ring bears a substituent $R^{43}$ or $R^{43'}$,

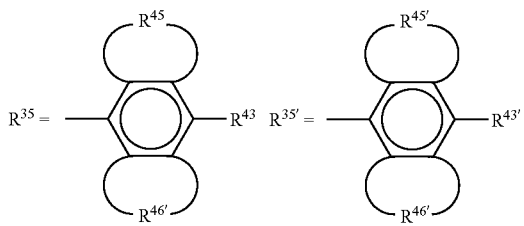

$R^{43}$ is a $C_1$-$C_{10}$-alkyl radical, a $C_2$-$C_{10}$-alkenyl radical, a $C_6$-$C_{18}$-aryl radical, a $C_7$-$C_{20}$-arylalkyl radical, a $C_7$-$C_{20}$-alkylaryl radical, a $C_8$-$C_{20}$-arylalkenyl radical, where the hydrocarbon radicals may also be halogenated or partially halogenated by fluorine or chlorine, $—N(R^{44})_2$, $—P(R^{44})_2$, $—SR^{44}$, $—Si(R^{44})_3$, $—N(R^{44})^{3+}$ or $—P(R^{44})^{3+}$, where the radicals $R^{44}$ are identical or different and are each a hydrogen atom or a hydrocarbon group which may be halogenated, linear, cyclic or branched, e.g. a $C_1$-$C_{10}$-alkyl group, a $C_2$-$C_{10}$-alkenyl group, a $C_6$-$C_{20}$-aryl group, a $C_7$-$C_{40}$-arylalkyl group, a $C_7$-$C_{40}$-alkylaryl group or a $C_8$-$C_{40}$-arylalkenyl group, $R^{43'}$ is as defined for $R^{43}$ or is hydrogen, $R^{45}$, $R^{45'}$, $R^{46}$ and $R^{46'}$ are each hydrogen or a $C_4$-$C_8$-aryl ring system.

In formula I, it is very particularly preferred that $M^{11}$ is zirconium, $R^{31}$, $R^{32}$ are identical and are each chlorine, methyl or phenoxide, $R^{33}$, $R^{33'}$ are different, $R^{33}$ is methyl, ethyl, n-propyl or n-butyl, $R^{33'}$ is a hydrocarbon group which is cyclized in the α position or branched in the α position and in which the atom in the α position is bound to a total of three carbon atoms, e.g. a $C_3$-$C_{10}$-alkyl group or a $C_3$-$C_{10}$-alkenyl group, $R^{39}$ is $R^{40}R^{41}Si=$, $R^{40}R^{41}C=$ or $—(R^{40}R^{41}C—CR^{40}R^{41})—$, where $R^{40}$ and $R^{41}$ are identical or different and are each phenyl or methyl, $R^{34}$, $R^{36}$, $R^{37}$ and $R^{38}$ and also $R^{34'}$, $R^{36'}$, $R^{37'}$ and $R^{38'}$ are each hydrogen, $R^{35}$, $R^{35'}$ are identical or different and are each a $C_6$-$C_{20}$-aryl group, in particular a phenyl or 1-naphthyl group which bears a substituent $R^{43}$ or $R^{43'}$ in the para position relative to the point of linkage to the indenyl ring, where $R^{43}$ or $R^{43'}$ is a branched $C_3$-$C_{10}$-alkyl radical, a branched $C_3$-$C_{10}$-alkenyl radical, a branched $C_7$-$C_{20}$-alkylaryl radical or an $Si(R^{44})_3$ radical where $R^{44}$ is particularly preferably as defined for $R^{33}$, where the hydrocarbon radicals may also be halogenated or partially halogenated by fluorine or chlorine.

Examples of preferred metallocene components of the catalyst system of the present invention are combinations of the following molecular fragments of the compound I:

$M^{11}R^{31}R^{32}$:

$ZrCl_2$, $Zr(CH_3)_2$, $Zr(O—C_6H_5)_2$ $R^{33}$:

methyl, ethyl, n-propyl, n-butyl, $R^{33'}$:

isopropyl, sec-butyl, cyclobutyl, 1-methylbutyl, 1-ethylbutyl, 1-methylpentyl, cyclopentyl, cyclohexyl, cyclopent-2-enyl, cyclopent-3-enyl, cyclohex-2-enyl, cyclohex-3-enyl, para-methylcyclohexyl, $R^{34}$, $R^{36}$, $R^{37}$ and $R^{38}$ and also $R^{34'}$, $R^{36'}$, $R^{37'}$ and $R^{38'}$: hydrogen, $R^{35}$, $R^{35'}$:

p-isopropylphenyl, p-tert-butylphenyl, p-s-butylphenyl, p-cyclohexyl, p-trimethylsilylphenyl, p-adamantylphenyl, p-tris(trifluoromethyl)methylphenyl, $R^{39}$:

dimethylsilanediyl, dimethylgermanediyl, ethylidene, 1-methylethylidene, 1,1-dimethylethylidene, 1,2-dimethylethylidene, 1,1,2,2-tetramethylethylidene, dimethylmethylidene, phenylmethylmethylidene, diphenylmethylidene.

Specific examples of preferred metallocene components of the catalyst system of the present invention are thus the following compounds I:

2-isopropyl, 2-methyl, symmetrically substituted in the 4 positions:

dimethylsilanediyl(2-isopropyl-4-(p-isopropylphenyl)indenyl)(2-methyl-4-(p-isopropylphenyl)indenyl)zirconium dichloride, dimethylsilanediyl(2-isopropyl-4-(p-tert-butylphenyl)indenyl)(2-methyl-4-(p-tert-butylphenyl)indenyl)zirconium dichloride, dimethylsilanediyl(2-isopropyl-4-(p-sec-butylphenyl)indenyl)(2-methyl-4-(p-sec-butylphenyl)indenyl)zirconium dichloride, dimethylsilanediyl(2-isopropyl-4-(p-cyclohexylphenyl)indenyl)(2-methyl-4-(p-cyclohexylphenyl)indenyl)zirconium dichloride, dimethylsilanediyl(2-isopropyl-4-(p-trimethylsilylphenyl)-indenyl)(2-methyl-4-(p-trimethylsilylphenyl)indenyl)zirconium dichloride, dimethylsilanediyl(2-isopropyl-4-(p-adamantylphenyl)indenyl)(2-methyl-4-(p-adamantylphenyl)inden yl)zirconium dichloride, dimethylsilanediyl(2-isopropyl-4-(p-tris(trifluoromethyl) methylphenyl)indenyl)(2-methyl-4-(p-tris(trifluoromethyl)methylphenyl)indenyl)zirconium dichloride, 2-sec-butyl, 2-methyl, symmetrically substituted in the 4 positions:

dimethylsilanediyl(2-sec-butyl-4-(p-isopropylphenyl)indenyl)(2-methyl-4-(p-isopropylphenyl)indenyl)zirconium dichloride, dimethylsilanediyl(2-sec-butyl-4-(p-tert-butylphenyl)indenyl)(2-methyl-4-(p-tert-butylphenyl)indenyl)zirconium dichloride, dimethylsilanediyl(2-sec-butyl-4-(p-sec-butylphenyl)indenyl)(2-methyl-4-(p-sec-butylphenyl)indenyl)zirconium dichloride, dimethylsilanediyl(2-sec-butyl-4-(p-cyclohexylphenyl)indenyl)(2-methyl-4-(p-cyclohexylphenyl)indenyl)zirconium dichloride, dimethylsilanediyl(2-sec-butyl-4-(p-trimethylsilylphenyl)-indenyl)(2-methyl-4-(p-trimethylsilylphenyl)indenyl)zirconium dichloride, dimethylsilanediyl(2-sec-butyl-4-(p-adamantylphenyl)indenyl)-(2-methyl-4-(p-adamantylphenyl)indenyl)zirconium dichloride,
dimethylsilanediyl(2-sec-butyl-4-(p-tris(trifluoromethyl)methyl-phenyl)indenyl)(2-methyl-4-(p-tris(trifluoromethyl)methylphenyl)-indenyl)zirconium dichloride, 2-(1-methylbutyl), 2-methyl, symmetrically substituted in the 4 positions:
dimethylsilanediyl(2-(1-methylbutyl)-4-(p-isopropylphenyl)-indenyl)(2-methyl-4-(p-isopropylphenyl)indenyl) zirconium dichloride,
dimethylsilanediyl(2-(1-methylbutyl)-4-(p-tert-butylphenyl)-indenyl)(2-methyl-4-(p-tert-butylphenyl)indenyl)zirconium dichloride,
dimethylsilanediyl(2-(1-methylbutyl)-4-(p-sec-butylphenyl)-indenyl)(2-methyl-4-(p-sec-butylphenyl)indenyl)zirconium dichloride,
dimethylsilanediyl(2-(1-methylbutyl)-4-(p-cyclohexylphenyl)-indenyl)(2-methyl-4-(p-(1-methylbutyl)phenyl)indenyl)zirconium dichloride,
dimethylsilanediyl(2-(1-methylbutyl)-4-(p-trimethylsilylphenyl)-indenyl)(2-methyl-4-(p-trimethylsilylphenyl)indenyl)zirconium dichloride,
dimethylsilanediyl(2-(1-methylbutyl)-4-(p-adamantylphenyl)-indenyl)(2-methyl-4-(p-adamantylphenyl)indenyl) zirconium dichloride,
dimethylsilanediyl(2-(1-methylbutyl)-4-(p-tris(trifluoromethyl)-methylphenyl)indenyl)(2-methyl-4-(p-tris(trifluoromethyl)methyl-phenyl)indenyl)zirconium dichloride, 2-cyclopentyl, 2-methyl, symmetrically substituted in the 4 positions:
dimethylsilanediyl(2-cyclopentyl-4-(p-isopropylphenyl)indenyl)-(2-methyl-4-(p-isopropylphenyl)indenyl)zirconium dichloride,
dimethylsilanediyl(2-cyclopentyl-4-(p-tert-butylphenyl)indenyl)-(2-methyl-4-(p-tert-butylphenyl)indenyl)zirconium dichloride,
dimethylsilanediyl(2-cyclopentyl-4-(p-sec-butylphenyl)indenyl)-(2-methyl-4-(p-sec-butylphenyl)indenyl)zirconium dichloride,
dimethylsilanediyl(2-cyclopentyl-4-(p-cyclohexylphenyl)indenyl)-(2-methyl-4-(p-cyclohexylphenyl)indenyl)zirconium dichloride,
dimethylsilanediyl(2-cyclopentyl-4-(p-trimethylsilylphenyl)-indenyl)(2-methyl-4-(p-trimethylsilylphenyl)indenyl)zirconium dichloride,
dimethylsilanediyl(2-cyclopentyl-4-(p-adamantylphenyl)indenyl)-(2-methyl-4-(p-adamantylphenyl)indenyl)zirconium dichloride,
dimethylsilanediyl(2-cyclopentyl-4-(p-tris(trifluoromethyl)-methylphenyl)indenyl)(2-methyl-4-(p-tris(trifluoromethyl)methyl-phenyl)indenyl)zirconium dichloride, 2-cyclohexyl, 2-methyl, symmetrically substituted in the 4 positions:
dimethylsilanediyl(2-cyclohexyl-4-(p-isopropylphenyl)indenyl)(2-methyl-4-(p-isopropylphenyl)indenyl)zirconium dichloride,
dimethylsilanediyl(2-cyclohexyl-4-(p-tert-butylphenyl)indenyl)-(2-methyl-4-(p-tert-butylphenyl)indenyl)zirconium dichloride,
dimethylsilanediyl(2-cyclohexyl-4-(p-sec-butylphenyl)indenyl)-(2-methyl-4-(p-sec-butylphenyl)indenyl)zirconium dichloride,
dimethylsilanediyl(2-cyclohexyl-4-(p-cyclohexylphenyl)indenyl)-(2-methyl-4-(p-cyclohexylphenyl)indenyl)zirconium dichloride,
dimethylsilanediyl(2-cyclohexyl-4-(p-trimethylsilylphenyl)-indenyl)(2-methyl-4-(p-trimethylsilylphenyl)indenyl)zirconium dichloride,
dimethylsilanediyl(2-cyclohexyl-4-(p-adamantylphenyl)indenyl)(2-methyl-4-(p-adamantylphenyl)indenyl)zirconium dichloride,
dimethylsilanediyl(2-cyclohexyl-4-(p-tris(trifluoromethyl)-methylphenyl)indenyl)(2-methyl-4-(p-tris(trifluoromethyl)methyl-phenyl)indenyl)zirconium dichloride, 2-p-methylcyclohexyl, 2-methyl, symmetrically substituted in the 4 positions:
dimethylsilanediyl(2-p-methylcyclohexyl-4-(p-isopropylphenyl)-indenyl)(2-methyl-4-(p-isopropylphenyl)indenyl)zirconium dichloride,
dimethylsilanediyl(2-p-methylcyclohexyl-4-(p-tert-butylphenyl)-indenyl)(2-methyl-4-(p-tert-butylphenyl)indenyl)zirconium dichloride,
dimethylsilanediyl(2-p-methylcyclohexyl-4-(p-sec-butylphenyl)-indenyl)(2-methyl-4-(p-sec-butylphenyl)indenyl)zirconium dichloride,
dimethylsilanediyl(2-p-methylcyclohexyl-4-(p-cyclohexylphenyl)-indenyl)(2-methyl-4-(p-cyclohexylphenyl)indenyl)zirconium dichloride,
dimethylsilanediyl(2-p-methylcyclohexyl-4-(p-trimethylsilyl-phenyl)indenyl)(2-methyl-4-(p-trimethylsilylphenyl) indenyl)-zirconium dichloride,
dimethylsilanediyl(2-p-methylcyclohexyl-4-(p-adamantylphenyl)-indenyl)(2-methyl-4-(p-adamantylphenyl)indenyl)zirconium dichloride,
dimethylsilanediyl(2-p-methylcyclohexyl-4-(p-tris(trifluoro-methyl)methylphenyl)indenyl)(2-methyl-4-(p-tris(trifluoromethyl)-methylphenyl)indenyl)zirconium dichloride, 2-isopropyl, 4-(p-tert-butylphenyl), 2-methyl, various substituents in the other 4 position:
dimethylsilanediyl(2-isopropyl-4-(p-tert-butylphenyl)indenyl)(2-methyl-4-(p-isopropylphenyl)indenyl)zirconium dichloride,
dimethylsilanediyl(2-isopropyl-4-(p-tert-butylphenyl)indenyl)(2-methyl-4-(p-sec-butylphenyl)indenyl)zirconium dichloride,
dimethylsilanediyl(2-isopropyl-4-(p-tert-butylphenyl)indenyl)(2-methyl-4-(p-cyclohexylphenyl)indenyl)zirconium dichloride,
dimethylsilanediyl(2-isopropyl-4-(p-tert-butylphenyl)indenyl)(2-methyl-4-(p-trimethylsilylphenyl)indenyl)zirconium dichloride,
dimethylsilanediyl(2-isopropyl-4-(p-tert-butylphenyl)indenyl)(2-methyl-4-(p-adamantylphenyl)indenyl)zirconium dichloride,
dimethylsilanediyl(2-isopropyl-4-(p-tert-butylphenyl)indenyl)(2-methyl-4-(p-tris(trifluoromethyl)methylphenyl)indenyl)zirconium dichloride, 2-sec-butyl, 4-(p-tert-butylphenyl), 2-methyl, various substituents in the other 4 position:
dimethylsilanediyl(2-sec-butyl-4-(p-tert-butylphenyl)indenyl)(2-methyl-4-(p-isopropylphenyl)indenyl)zirconium dichloride,
dimethylsilanediyl(2-sec-butyl-4-(p-tert-butylphenyl)indenyl)(2-methyl-4-(p-sec-butylphenyl)indenyl)zirconium dichloride,
dimethylsilanediyl(2-sec-butyl-4-(p-tert-butylphenyl)indenyl)(2-methyl-4-(p-cyclohexylphenyl)indenyl)zirconium dichloride,
dimethylsilanediyl(2-sec-butyl-4-(p-tert-butylphenyl)indenyl)(2-methyl-4-(p-trimethylsilylphenyl)indenyl)zirconium dichloride, dimethylsilanediyl(2-sec-butyl-4-(p-tert-butylphenyl)indenyl)(2-methyl-4-(p-adamantylphenyl)indenyl)zirconium dichloride,
dimethylsilanediyl(2-sec-butyl-4-(p-tert-butylphenyl)indenyl)(2-methyl-4-(p-tris(trifluoromethyl)methylphenyl)indenyl)zirconium dichloride, 2-(1-methylbutyl), 4-(p-tert-butylphenyl), 2-methyl, various substituents in the other 4 position:
dimethylsilanediyl(2-(1-methylbutyl)-4-(p-tert-butylphenyl)-indenyl)(2-methyl-4-(p-isopropylphenyl)indenyl)zirconium dichloride,
dimethylsilanediyl(2-(1-methylbutyl)-4-(p-tert-butylphenyl)-indenyl)(2-methyl-4-(p-sec-butylphenyl)indenyl)zirconium dichloride,
dimethylsilanediyl(2-(1-methylbutyl)-4-(p-tert-butylphenyl)-indenyl)(2-methyl-4-(p-cyclohexylphenyl)indenyl)zirconium dichloride,
dimethylsilanediyl(2-(1-methylbutyl)-4-(p-tert-butylphenyl)-indenyl)(2-methyl-4-(p-trimethylsilylphenyl)indenyl)zirconium dichloride,
dimethylsilanediyl(2-(1-methylbutyl)-4-(p-tert-butylphenyl)-indenyl)(2-methyl-4-(p-adamantylphenyl)indenyl)zirconium dichloride,
dimethylsilanediyl(2-(1-methylbutyl)-4-(p-tert-butylphenyl)-indenyl)(2-methyl-4-(p-tris(trifluoromethyl)methylphenyl)-indenyl)zirconium dichloride, 2-cyclopentyl, 4-(p-tert-butylphenyl), 2-methyl, various substituents in the other 4 position:
dimethylsilanediyl(2-cyclopentyl-4-(p-tert-butylphenyl)indenyl)-(2-methyl-4-(p-isopropylphenyl)indenyl)zirconium dichloride,
dimethylsilanediyl(2-cyclopentyl-4-(p-tert-butylphenyl)indenyl)-(2-methyl-4-(p-sec-butylphenyl)indenyl)zirconium dichloride,
dimethylsilanediyl(2-cyclopentyl-4-(p-tert-butylphenyl)indenyl)-(2-methyl-4-(p-cyclohexylphenyl)indenyl)zirconium dichloride,
dimethylsilanediyl(2-cyclopentyl-4-(p-tert-butylphenyl)indenyl)-(2-methyl-4-(p-trimethylsilylphenyl)indenyl)zirconium dichloride,
dimethylsilanediyl(2-cyclopentyl-4-(p-tert-butylphenyl)indenyl)-(2-methyl-4-(p-adamantylphenyl)indenyl)zirconium dichloride,
dimethylsilanediyl(2-cyclopentyl-4-(p-tert-butylphenyl)indenyl)-(2-methyl-4-(p-tris(trifluoromethyl)methylphenyl)indenyl)-zirconium dichloride, 2-cyclohexyl, 4-(p-tert-butylphenyl), 2-methyl, various substituents in the other 4 position:
dimethylsilanediyl(2-cyclohexyl-4-(p-tert-butylphenyl)indenyl)-(2-methyl-4-(p-isopropylphenyl)indenyl)zirconium dichloride,
dimethylsilanediyl(2-cyclohexyl-4-(p-tert-butylphenyl)indenyl)-(2-methyl-4-(p-sec-butylphenyl)indenyl)zirconium dichloride,
dimethylsilanediyl(2-cyclohexyl-4-(p-tert-butylphenyl)indenyl)-(2-methyl-4-(p-cyclohexylphenyl)indenyl)zirconium dichloride,
dimethylsilanediyl(2-cyclohexyl-4-(p-tert-butylphenyl)indenyl)-(2-methyl-4-(p-trimethylsilylphenyl)indenyl)zirconium dichloride,
dimethylsilanediyl(2-cyclohexyl-4-(p-tert-butylphenyl)indenyl)-(2-methyl-4-(p-adamantylphenyl)indenyl)zirconium dichloride,
dimethylsilanediyl(2-cyclohexyl-4-(p-tert-butylphenyl)indenyl)-(2-methyl-4-(p-tris(trifluoromethyl)methylphenyl)indenyl)-zirconium dichloride, 2-(p-methylcyclohexyl), 4-(p-tert-butylphenyl), 2-methyl, various substituents in the other 4 position:
dimethylsilanediyl(2-(p-methylcyclohexyl)-4-(p-tert-butylphenyl)-indenyl)(2-methyl-4-(p-isopropylphenyl)indenyl)zirconium dichloride,
dimethylsilanediyl(2-(p-methylcyclohexyl)-4-(p-tert-butylphenyl)-indenyl)(2-methyl-4-(p-sec-butylphenyl)indenyl)zirconium dichloride,
dimethylsilanediyl(2-(p-methylcyclohexyl)-4-(p-tert-butylphenyl)-indenyl)(2-methyl-4-(p-cyclohexylphenyl)indenyl)zirconium dichloride,
dimethylsilanediyl(2-(p-methylcyclohexyl)-4-(p-tert-butylphenyl)-indenyl)(2-methyl-4-(p-trimethylsilylphenyl)indenyl)zirconium dichloride,
dimethylsilanediyl(2-(p-methylcyclohexyl)-4-(p-tert-butylphenyl)-indenyl)(2-methyl-4-(p-adamantylphenyl)indenyl)zirconium dichloride,
dimethylsilanediyl(2-(p-methylcyclohexyl)-4-(p-tert-butylphenyl)-indenyl)(2-methyl-4-(p-tris(trifluoromethyl)methylphenyl)-indenyl)zirconium dichloride, 2-isopropyl, 4-(p-isopropylphenyl), 2-methyl, various substituents in the other 4 position:
dimethylsilanediyl(2-isopropyl-4-(p-isopropylphenyl)indenyl)(2-methyl-4-(p-tert-butylphenyl)indenyl)zirconium dichloride,
dimethylsilanediyl(2-isopropyl-4-(p-isopropylphenyl)indenyl)(2-methyl-4-(p-sec-butylphenyl)indenyl)zirconium dichloride,
dimethylsilanediyl(2-isopropyl-4-(p-isopropylphenyl)indenyl)(2-methyl-4-(p-cyclohexylphenyl)indenyl)zirconium dichloride,
dimethylsilanediyl(2-isopropyl-4-(p-isopropylphenyl)indenyl)(2-methyl-4-(p-trimethylsilylphenyl)indenyl)zirconium dichloride,
dimethylsilanediyl(2-isopropyl-4-(p-isopropylphenyl)indenyl)(2-methyl-4-(p-adamantylphenyl)indenyl)zirconium dichloride,
dimethylsilanediyl(2-isopropyl-4-(p-isopropylphenyl)indenyl)(2-methyl-4-(p-tris(trifluoromethyl)methylphenyl)indenyl)zirconium dichloride, 2-sec-butyl, 4-(p-isopropylphenyl), 2-methyl, various substituents in the other 4 position:
dimethylsilanediyl(2-sec-butyl-4-(p-isopropylphenyl)indenyl)(2-methyl-4-(p-tert-butylphenyl)indenyl)zirconium dichloride,
dimethylsilanediyl(2-sec-butyl-4-(p-isopropylphenyl)indenyl)(2-methyl-4-(p-sec-butylphenyl)indenyl)zirconium dichloride,
dimethylsilanediyl(2-sec-butyl-4-(p-isopropylphenyl)indenyl)(2-methyl-4-(p-cyclohexylphenyl)indenyl)zirconium dichloride,
dimethylsilanediyl(2-sec-butyl-4-(p-isopropylphenyl)indenyl)(2-methyl-4-(p-trimethylsilylphenyl)indenyl)zirconium dichloride,
dimethylsilanediyl(2-sec-butyl-4-(p-isopropylphenyl)indenyl)(2-methyl-4-(p-adamantylphenyl)indenyl)zirconium dichloride,
dimethylsilanediyl(2-sec-butyl-4-(p-isopropylphenyl)indenyl)(2-methyl-4-(p-tris(trifluoromethyl)methylphenyl)indenyl)zirconium dichloride, 2-(1-methylbutyl), 4-(p-isopropylphenyl), 2-methyl, various substituents in the other 4 position:
dimethylsilanediyl(2-(1-methylbutyl)-4-(p-isopropylphenyl)-indenyl)(2-methyl-4-(p-tert-butylphenyl)indenyl)zirconium dichloride, dimethylsilanediyl(2-(1-methylbutyl)-4-(p-isopropylphenyl)-indenyl)(2-methyl-4-(p-sec-butylphenyl)indenyl)zirconium dichloride,
dimethylsilanediyl(2-(1-methylbutyl)-4-(p-isopropylphenyl)-indenyl)(2-methyl-4-(p-cyclohexylphenyl)indenyl)zirconium dichloride,
dimethylsilanediyl(2-(1-methylbutyl)-4-(p-isopropylphenyl)-indenyl)(2-methyl-4-(p-trimethylsilylphenyl)indenyl)zirconium dichloride,
dimethylsilanediyl(2-(1-methylbutyl)-4-(p-isopropylphenyl)-indenyl)(2-methyl-4-(p-adamantylphenyl)indenyl)zirconium dichloride,
dimethylsilanediyl(2-(1-methylbutyl)-4-(p-isopropylphenyl)-indenyl)(2-methyl-4-(p-tris(trifluoromethyl)methylphenyl)-indenyl)zirconium dichloride, 2-cyclopentyl, 4-(p-isopropylphenyl), 2-methyl, various substituents in the other 4 position:
dimethylsilanediyl(2-cyclopentyl-4-(p-isopropylphenyl)indenyl)-(2-methyl-4-(p-tert-butylphenyl)indenyl)zirconium dichloride,
dimethylsilanediyl(2-cyclopentyl-4-(p-isopropylphenyl)indenyl)-(2-methyl-4-(p-sec-butylphenyl)indenyl)zirconium dichloride,
dimethylsilanediyl(2-cyclopentyl-4-(p-isopropylphenyl)indenyl)-(2-methyl-4-(p-cyclohexylphenyl)indenyl)zirconium dichloride,
dimethylsilanediyl(2-cyclopentyl-4-(p-isopropylphenyl)indenyl)-(2-methyl-4- (p-trimethylsilylphenyl) indenyl) zirconium dichloride,
dimethylsilanediyl(2-cyclopentyl-4-(p-isopropylphenyl)indenyl)-(2-methyl-4-(p-adamantylphenyl)indenyl)zirconium dichloride,
dimethylsilanediyl(2-cyclopentyl-4-(p-isopropylphenyl)indenyl)-(2-methyl-4-(p-tris(trifluoromethyl)methylphenyl)indenyl)-zirconium dichloride, 2-cyclohexyl, 4-(p-isopropylphenyl), 2-methyl, various substituents in the other 4 position:
dimethylsilanediyl(2-cyclohexyl-4-(p-isopropylphenyl)indenyl)(2-methyl-4-(p-tert-butylphenyl)indenyl)zirconium dichloride,
dimethylsilanediyl(2-cyclohexyl-4-(p-isopropylphenyl)indenyl)(2-methyl-4-(p-sec-butylphenyl)indenyl)zirconium dichloride,
dimethylsilanediyl(2-cyclohexyl-4-(p-isopropylphenyl)indenyl)(2-methyl-4-(p-cyclohexylphenyl)indenyl)zirconium dichloride,
dimethylsilanediyl(2-cyclohexyl-4-(p-isopropylphenyl)indenyl)(2-methyl-4-(p-trimethylsilylphenyl)indenyl)zirconium dichloride,
dimethylsilanediyl(2-cyclohexyl-4-(p-isopropylphenyl)indenyl)(2-methyl-4-(p-adamantylphenyl)indenyl)zirconium dichloride,
dimethylsilanediyl(2-cyclohexyl-4-(p-isopropylphenyl)indenyl)(2-methyl-4-(p-tris(trifluoromethyl)methylphenyl)indenyl)zirconium dichloride, 2-(p-methylcyclohexyl), 4-(p-isopropylphenyl), 2-methyl, various substituents in the other 4 position:
dimethylsilanediyl(2-(p-methylcyclohexyl)-4-(p-isopropylphenyl)-indenyl)(2-methyl-4-(p-tert-butylphenyl)indenyl)zirconium dichloride,
dimethylsilanediyl(2-(p-methylcyclohexyl)-4-(p-isopropylphenyl)-indenyl)(2-methyl-4-(p-sec-butylphenyl)indenyl)zirconium dichloride,
dimethylsilanediyl(2-(p-methylcyclohexyl)-4-(p-isopropylphenyl)-indenyl)(2-methyl-4-(p-cyclohexylphenyl)indenyl)zirconium dichloride,
dimethylsilanediyl(2-(p-methylcyclohexyl)-4-(p-isopropylphenyl)-indenyl)(2-methyl-4-(p-trimethylsilylphenyl)indenyl)zirconium dichloride,
dimethylsilanediyl(2-(p-methylcyclohexyl)-4-(p-isopropylphenyl)-indenyl)(2-methyl-4-(p-adamantylphenyl)indenyl)zirconium dichloride,
dimethylsilanediyl(2-(p-methylcyclohexyl)-4-(p-isopropylphenyl)-indenyl)(2-methyl-4-(p-tris(trifluoromethyl)methylphenyl)-indenyl)zirconium dichloride, 2-isopropyl, 4-(p-sec-butyl), 2-methyl, various substituents in the other 4 position:
dimethylsilanediyl(2-isopropyl-4-(p-sec-butyl)indenyl)(2-methyl-4-(p-tert-butylphenyl)indenyl)zirconium dichloride,
dimethylsilanediyl(2-isopropyl-4-(p-sec-butyl)indenyl)(2-methyl-4-(p-isopropylphenyl)indenyl)zirconium dichloride,
dimethylsilanediyl(2-isopropyl-4-(p-sec-butyl)indenyl)(2-methyl-4-(p-cyclohexylphenyl)indenyl)zirconium dichloride,
dimethylsilanediyl(2-isopropyl-4-(p-sec-butyl)indenyl)(2-methyl-4-(p-trimethylsilylphenyl)indenyl)zirconium dichloride,
dimethylsilanediyl(2-isopropyl-4-(p-sec-butyl)indenyl)(2-methyl-4-(p-adamantylphenyl)indenyl)zirconium dichloride,
dimethylsilanediyl(2-isopropyl-4-(p-sec-butyl)indenyl)(2-methyl-4-(p-tris(trifluoromethyl)methylphenyl)indenyl)zirconium dichloride, 2-sec-butyl, 4-(p-sec-butyl), 2-methyl, various substituents in the other 4 position:
dimethylsilanediyl(2-sec-butyl-4-(p-sec-butyl)indenyl)(2-methyl-4-(p-tert-butylphenyl)indenyl)zirconium dichloride,
dimethylsilanediyl(2-sec-butyl-4-(p-sec-butyl)indenyl)(2-methyl-4-(p-isopropylphenyl)indenyl)zirconium dichloride,
dimethylsilanediyl(2-sec-butyl-4-(p-sec-butyl)indenyl)(2-methyl-4-(p-cyclohexylphenyl)indenyl)zirconium dichloride,
dimethylsilanediyl(2-sec-butyl-4-(p-sec-butyl)indenyl)(2-methyl-4-(p-trimethylsilylphenyl)indenyl)zirconium dichloride,
dimethylsilanediyl(2-sec-butyl-4-(p-sec-butyl)indenyl)(2-methyl-4-(p-adamantylphenyl)indenyl)zirconium dichloride,
dimethylsilanediyl(2-sec-butyl-4-(p-sec-butyl)indenyl)(2-methyl-4-(p-tris(trifluoromethyl)methylphenyl)indenyl)zirconium dichloride, 2-(1-methylbutyl), 4-(p-sec-butyl), 2-methyl, various substituents in the other 4 position:
dimethylsilanediyl(2-(1-methylbutyl)-4-(p-sec-butyl)indenyl)(2-methyl-4-(p-tert-butylphenyl)indenyl)zirconium dichloride,
dimethylsilanediyl(2-(1-methylbutyl)-4-(p-sec-butyl)indenyl)(2-methyl-4-(p-isopropylphenyl)indenyl)zirconium dichloride,
dimethylsilanediyl(2-(1-methylbutyl)-4-(p-sec-butyl)indenyl)(2-methyl-4-(p-cyclohexylphenyl)indenyl)zirconium dichloride,
dimethylsilanediyl(2-(1-methylbutyl)-4-(p-sec-butyl)indenyl)(2-methyl-4-(p-trimethylsilylphenyl)indenyl)zirconium dichloride,
dimethylsilanediyl(2-(1-methylbutyl)-4-(p-sec-butyl)indenyl)(2-methyl-4-(p-adamantylphenyl)indenyl)zirconium dichloride, dimethylsilanediyl(2-(1-methylbutyl)-4-(p-sec-butyl)indenyl)(2-methyl-4-(p-tris(trifluoromethyl)methylphenyl)indenyl)zirconium dichloride, 2-cyclopentyl, 4-(p-sec-butyl), 2-methyl, various substituents in the other 4 position:
dimethylsilanediyl(2-cyclopentyl-4-(p-sec-butyl)indenyl)(2-methyl-4-(p-tert-butylphenyl)indenyl)zirconium dichloride,
dimethylsilanediyl(2-cyclopentyl-4-(p-sec-butyl)indenyl)(2-methyl-4-(p-isopropylphenyl)indenyl)zirconium dichloride,
dimethylsilanediyl(2-cyclopentyl-4-(p-sec-butyl)indenyl)(2-methyl-4-(p-cyclohexylphenyl)indenyl)zirconium dichloride,
dimethylsilanediyl(2-cyclopentyl-4-(p-sec-butyl)indenyl)(2-methyl-4-(p-trimethylsilylphenyl)indenyl)zirconium dichloride,
dimethylsilanediyl(2-cyclopentyl-4-(p-sec-butyl)indenyl)(2-methyl-4-(p-adamantylphenyl)indenyl)zirconium dichloride,
dimethylsilanediyl(2-cyclopentyl-4-(p-sec-butyl)indenyl)(2-methyl-4-(p-tris(trifluoromethyl)methylphenyl)indenyl)zirconium dichloride, 2-cyclohexyl, 4-(p-sec-butyl), 2-methyl, various substituents in the other 4 position:
dimethylsilanediyl(2-cyclohexyl-4-(p-sec-butyl)indenyl)(2-methyl-4-(p-tert-butylphenyl)indenyl)zirconium dichloride,
dimethylsilanediyl(2-cyclohexyl-4-(p-sec-butyl)indenyl)(2-methyl-4-(p-isopropylphenyl)indenyl)zirconium dichloride,
dimethylsilanediyl(2-cyclohexyl-4-(p-sec-butyl)indenyl)(2-methyl-4-(p-cyclohexylphenyl)indenyl)zirconium dichloride,
dimethylsilanediyl(2-cyclohexyl-4-(p-sec-butyl)indenyl)(2-methyl-4-(p-trimethylsilylphenyl)indenyl)zirconium dichloride,
dimethylsilanediyl(2-cyclohexyl-4-(p-sec-butyl)indenyl)(2-methyl-4-(p-adamantylphenyl)indenyl)zirconium dichloride,
dimethylsilanediyl(2-cyclohexyl-4-(p-sec-butyl)indenyl)(2-methyl-4-(p-tris(trifluoromethyl)methylphenyl)indenyl)zirconium dichloride, 2-(p-methylcyclohexyl), 4-(p-sec-butyl), 2-methyl, various substituents in the other 4 position:
dimethylsilanediyl(2-(p-methylcyclohexyl)-4-(p-sec-butyl)-indenyl)(2-methyl-4-(p-tert-butylphenyl)indenyl)zirconium dichloride,
dimethylsilanediyl(2-(p-methylcyclohexyl)-4-(p-sec-butyl)-indenyl)(2-methyl-4-(p-isopropylphenyl)indenyl)zirconium dichloride,
dimethylsilanediyl(2-(p-methylcyclohexyl)-4-(p-sec-butyl)-indenyl)(2-methyl-4-(p-cyclohexylphenyl)indenyl)zirconium dichloride,
dimethylsilanediyl(2-(p-methylcyclohexyl)-4-(p-sec-butyl)-indenyl)(2-methyl-4-(p-trimethylsilylphenyl)indenyl)zirconium dichloride,
dimethylsilanediyl(2-(p-methylcyclohexyl)-4-(p-sec-butyl)-indenyl)(2-methyl-4-(p-adamantylphenyl)indenyl)zirconium dichloride,
dimethylsilanediyl(2-(p-methylcyclohexyl)-4-(p-sec-butyl)-indenyl)(2-methyl-4-(p-tris(trifluoromethyl)methylphenyl)-indenyl)zirconium dichloride, 2-isopropyl, 2-ethyl, symmetrically substituted in the 4 positions:
dimethylsilanediyl(2-isopropyl-4-(p-isopropylphenyl)indenyl)(2-ethyl-4-(p-isopropylphenyl)indenyl)zirconium dichloride,
dimethylsilanediyl(2-isopropyl-4-(p-tert-butylphenyl)indenyl)(2-ethyl-4-(p-tert-butylphenyl)indenyl)zirconium dichloride,
dimethylsilanediyl(2-isopropyl-4-(p-sec-butylphenyl)indenyl)(2-ethyl-4-(p-sec-butylphenyl)indenyl)zirconium dichloride,
dimethylsilanediyl(2-isopropyl-4-(p-cyclohexylphenyl)indenyl)(2-ethyl-4-(p-cyclohexylphenyl)indenyl)zirconium dichloride,
dimethylsilanediyl(2-isopropyl-4-(p-trimethylsilylphenyl)-indenyl)(2-ethyl-4-(p-trimethylsilylphenyl)indenyl)zirconium dichloride,
dimethylsilanediyl(2-isopropyl-4-(p-adamantylphenyl)indenyl)(2-ethyl-4-(p-adamantylphenyl)indenyl)zirconium dichloride,
dimethylsilanediyl(2-isopropyl-4-(p-tris(trifluoromethyl)methyl-phenyl)indenyl)(2-ethyl-4-(p-tris(trifluoromethyl)methylphenyl)-indenyl)zirconium dichloride, 2-sec-butyl, 2-ethyl, symmetrically substituted in the 4 positions:
dimethylsilanediyl(2-sec-butyl-4-(p-isopropylphenyl)indenyl)(2-ethyl-4-(p-isopropylphenyl)indenyl)zirconium dichloride,
dimethylsilanediyl(2-sec-butyl-4-(p-tert-butylphenyl)indenyl)(2-ethyl-4-(p-tert-butylphenyl)indenyl)zirconium dichloride,
dimethylsilanediyl(2-sec-butyl-4-(p-sec-butylphenyl)indenyl)(2-ethyl-4-(p-sec-butylphenyl)indenyl)zirconium dichloride,
dimethylsilanediyl(2-sec-butyl-4-(p-cyclohexylphenyl)indenyl)(2-ethyl-4-(p-cyclohexylphenyl)indenyl)zirconium dichloride,
dimethylsilanediyl(2-sec-butyl-4-(p-trimethylsilylphenyl)-indenyl)(2-ethyl-4-(p-trimethylsilylphenyl)indenyl)zirconium dichloride,
dimethylsilanediyl(2-sec-butyl-4-(p-adamantylphenyl)indenyl)(2-ethyl-4-(p-adamantylphenyl)indenyl)zirconium dichloride,
dimethylsilanediyl(2-sec-butyl-4-(p-tris(trifluoromethyl)methyl-phenyl)indenyl)(2-ethyl-4-(p-tris(trifluoromethyl)methylphenyl)-indenyl)zirconium dichloride, 2-(1-methylbutyl), 2-ethyl, symmetrically substituted in the 4 positions:
dimethylsilanediyl(2-(1-methylbutyl)-4-(p-isopropylphenyl)-indenyl)(2-ethyl-4-(p-isopropylphenyl)indenyl)zirconium dichloride,
dimethylsilanediyl(2-(1-methylbutyl)-4-(p-tert-butylphenyl)-indenyl)(2-ethyl-4-(p-tert-butylphenyl)indenyl)zirconium dichloride,
dimethylsilanediyl(2-(1-methylbutyl)-4-(p-sec-butylphenyl)-indenyl)(2-ethyl-4-(p-sec-butylphenyl)indenyl)zirconium dichloride,
dimethylsilanediyl(2-(1-methylbutyl)-4-(p-cyclohexylphenyl)-indenyl)(2-ethyl-4-(p-(1-methylbutyl)phenyl)indenyl)zirconium dichloride,
dimethylsilanediyl(2-(1-methylbutyl)-4-(p-trimethylsilylphenyl)-indenyl)(2-ethyl-4-(p-trimethylsilylphenyl)indenyl)zirconium dichloride,
dimethylsilanediyl(2-(1-methylbutyl)-4-(p-adamantylphenyl)-indenyl)(2-ethyl-4-(p-adamantylphenyl)indenyl)zirconium dichloride,
dimethylsilanediyl(2-(1-methylbutyl)-4-(p-tris(trifluoromethyl)-methylphenyl)indenyl)(2-ethyl-4-(p-tris(trifluoromethyl)methyl-phenyl)indenyl)zirconium dichloride, 2-cyclopentyl, 2-ethyl, symmetrically substituted in the 4 positions:

dimethylsilanediyl(2-cyclopentyl-4-(p-isopropylphenyl)indenyl)-(2-ethyl-4-(p-isopropylphenyl)indenyl)zirconium dichloride,
dimethylsilanediyl(2-cyclopentyl-4-(p-tert-butylphenyl)indenyl)-(2-ethyl-4-(p-tert-butylphenyl)indenyl)zirconium dichloride,
dimethylsilanediyl(2-cyclopentyl-4-(p-sec-butylphenyl)indenyl)-(2-ethyl-4-(p-sec-butylphenyl)indenyl)zirconium dichloride,
dimethylsilanediyl(2-cyclopentyl-4-(p-cyclohexylphenyl)indenyl)-(2-ethyl-4-(p-cyclohexylphenyl)indenyl)zirconium dichloride,
dimethylsilanediyl(2-cyclopentyl-4-(p-trimethylsilylphenyl)-indenyl)(2-ethyl-4-(p-trimethylsilylphenyl)indenyl)zirconium dichloride,
dimethylsilanediyl(2-cyclopentyl-4-(p-adamantylphenyl)indenyl)-(2-ethyl-4-(p-adamantylphenyl)indenyl)zirconium dichloride,
dimethylsilanediyl(2-cyclopentyl-4-(p-tris(trifluoromethyl)-methylphenyl)indenyl)(2-ethyl-4-(p-tris(trifluoromethyl)methyl-phenyl)indenyl)zirconium dichloride, 2-cyclohexyl, 2-ethyl, symmetrically substituted in the 4 positions:

dimethylsilanediyl(2-cyclohexyl-4-(p-isopropylphenyl)indenyl)(2-ethyl-4-(p-isopropylphenyl)indenyl)zirconium dichloride,
dimethylsilanediyl(2-cyclohexyl-4-(p-tert-butylphenyl)indenyl)-(2-ethyl-4-(p-tert-butylphenyl)indenyl)zirconium dichloride,
dimethylsilanediyl(2-cyclohexyl-4-(p-sec-butylphenyl)indenyl)(2-ethyl-4-(p-sec-butylphenyl)indenyl)zirconium dichloride,
dimethylsilanediyl(2-cyclohexyl-4-(p-cyclohexylphenyl)indenyl)-(2-ethyl-4-(p-cyclohexylphenyl)indenyl)zirconium dichloride,
dimethylsilanediyl(2-cyclohexyl-4-(p-trimethylsilylphenyl)-indenyl)(2-ethyl-4-(p-trimethylsilylphenyl)indenyl)zirconium dichloride,
dimethylsilanediyl(2-cyclohexyl-4-(p-adamantylphenyl)indenyl)(2-ethyl-4-(p-adamantylphenyl)indenyl)zirconium dichloride,
dimethylsilanediyl(2-cyclohexyl-4-(p-tris(trifluoromethyl)methyl-phenyl)indenyl)(2-ethyl-4-(p-tris(trifluoromethyl)methylphenyl)-indenyl)zirconium dichloride, 2-p-methylcyclohexyl, 2-ethyl, symmetrically substituted in the 4 positions:

dimethylsilanediyl(2-p-methylcyclohexyl-4-(p-isopropylphenyl)-indenyl)(2-ethyl-4-(p-isopropylphenyl)indenyl)zirconium dichloride,
dimethylsilanediyl(2-p-methylcyclohexyl-4-(p-tert-butylphenyl)-indenyl)(2-ethyl-4-(p-tert-butylphenyl)indenyl)zirconium dichloride,
dimethylsilanediyl(2-p-methylcyclohexyl-4-(p-sec-butylphenyl)-indenyl)(2-ethyl-4-(p-sec-butylphenyl)indenyl)zirconium dichloride,
dimethylsilanediyl(2-p-methylcyclohexyl-4-(p-cyclohexylphenyl)-indenyl)(2-ethyl-4-(p-cyclohexylphenyl)indenyl)zirconium dichloride,
dimethylsilanediyl(2-p-methylcyclohexyl-4-(p-trimethylsilyl-phenyl)indenyl)(2-ethyl-4-(p-trimethylsilylphenyl)indenyl)-zirconium dichloride,
dimethylsilanediyl(2-p-methylcyclohexyl-4-(p-adamantylphenyl)-indenyl)(2-ethyl-4-(p-adamantylphenyl)indenyl)zirconium dichloride,
dimethylsilanediyl(2-p-methylcyclohexyl-4-(p-tris(trifluoro-methyl)methylphenyl)indenyl)(2-ethyl-4-(p-tris(trifluoromethyl)-methylphenyl)indenyl)zirconium dichloride, 2-isopropyl, 4-(p-tert-butylphenyl), 2-ethyl, various substituents in the other 4 position:

dimethylsilanediyl(2-isopropyl-4-(p-tert-butylphenyl)indenyl)-(2-ethyl-4-(p-isopropylphenyl)indenyl)zirconium dichloride,
dimethylsilanediyl(2-isopropyl-4-(p-tert-butylphenyl)indenyl)(2-ethyl-4-(p-sec-butylphenyl)indenyl)zirconium dichloride,
dimethylsilanediyl(2-isopropyl-4-(p-tert-butylphenyl)indenyl)(2-ethyl-4-(p-cyclohexylphenyl)indenyl)zirconium dichloride,
dimethylsilanediyl(2-isopropyl-4-(p-tert-butylphenyl)indenyl)(2-ethyl-4-(p-trimethylsilylphenyl)indenyl)zirconium dichloride,
dimethylsilanediyl(2-isopropyl-4-(p-tert-butylphenyl)indenyl)(2-ethyl-4-(p-adamantylphenyl)indenyl)zirconium dichloride,
dimethylsilanediyl(2-isopropyl-4-(p-tert-butylphenyl)indenyl)(2-ethyl-4-(p-tris(trifluoromethyl)methylphenyl)indenyl)zirconium dichloride, 2-sec-butyl, 4-(p-tert-butylphenyl), 2-ethyl, various substituents in the other 4 position:

dimethylsilanediyl(2-sec-butyl-4-(p-tert-butylphenyl)indenyl)(2-ethyl-4-(p-isopropylphenyl)indenyl)zirconium dichloride,
dimethylsilanediyl(2-sec-butyl-4-(p-tert-butylphenyl)indenyl)(2-ethyl-4-(p-sec-butylphenyl)indenyl)zirconium dichloride,
dimethylsilanediyl(2-sec-butyl-4-(p-tert-butylphenyl)indenyl)(2-ethyl-4-(p-cyclohexylphenyl)indenyl)zirconium dichloride,
dimethylsilanediyl(2-sec-butyl-4-(p-tert-butylphenyl)indenyl)(2-ethyl-4-(p-trimethylsilylphenyl)indenyl)zirconium dichloride,
dimethylsilanediyl(2-sec-butyl-4-(p-tert-butylphenyl)indenyl)(2-ethyl-4-(p-adamantylphenyl)indenyl)zirconium dichloride,
dimethylsilanediyl(2-sec-butyl-4-(p-tert-butylphenyl)indenyl)(2-ethyl-4-(p-tris(trifluoromethyl)methylphenyl)indenyl)zirconium dichloride, 2-(1-methylbutyl), 4-(p-tert-butylphenyl), 2-ethyl, various substituents in the other 4 position:

dimethylsilanediyl(2-(1-methylbutyl)-4-(p-tert-butylphenyl)-indenyl)(2-ethyl-4-(p-isopropylphenyl)indenyl)zirconium dichloride,
dimethylsilanediyl(2-(1-methylbutyl)-4-(p-tert-butylphenyl)-indenyl)(2-ethyl-4-(p-sec-butylphenyl)indenyl)zirconium dichloride,
dimethylsilanediyl(2-(1-methylbutyl)-4-(p-tert-butylphenyl)-indenyl)(2-ethyl-4-(p-cyclohexylphenyl)indenyl)zirconium dichloride,
dimethylsilanediyl(2-(1-methylbutyl)-4-(p-tert-butylphenyl)-indenyl)(2-ethyl-4-(p-trimethylsilylphenyl)indenyl)zirconium dichloride,
dimethylsilanediyl(2-(1-methylbutyl)-4-(p-tert-butylphenyl)-indenyl)(2-ethyl-4-(p-adamantylphenyl)indenyl)zirconium dichloride,
dimethylsilanediyl(2-(1-methylbutyl)-4-(p-tert-butylphenyl)-indenyl)(2-ethyl-4-(p-tris(trifluoromethyl)methylphenyl)indenyl)-zirconium dichloride, 2-cyclopentyl, 4-(p-tert-butylphenyl), 2-ethyl, various substituents in the other 4 position:

dimethylsilanediyl(2-cyclopentyl-4-(p-tert-butylphenyl)indenyl)-(2-ethyl-4-(p-isopropylphenyl)indenyl)zirconium dichloride,
dimethylsilanediyl(2-cyclopentyl-4-(p-tert-butylphenyl)indenyl)-(2-ethyl-4-(p-sec-butylphenyl)indenyl)zirconium dichloride,
dimethylsilanediyl(2-cyclopentyl-4-(p-tert-butylphenyl)indenyl)-(2-ethyl-4-(p-cyclohexylphenyl)indenyl)zirconium dichloride,
dimethylsilanediyl(2-cyclopentyl-4-(p-tert-butylphenyl)indenyl)-(2-ethyl-4-(p-trimethylsilylphenyl)indenyl)zirconium dichloride,
dimethylsilanediyl(2-cyclopentyl-4-(p-tert-butylphenyl)indenyl)-(2-ethyl-4-(p-adamantylphenyl)indenyl)zirconium dichloride,
dimethylsilanediyl(2-cyclopentyl-4-(p-tert-butylphenyl)indenyl)-(2-ethyl-4-(p-tris(trifluoromethyl)methylphenyl)indenyl)zirconium dichloride, 2-cyclohexyl, 4-(p-tert-butylphenyl), 2-ethyl, various substituents in the other 4 position:
dimethylsilanediyl(2-cyclohexyl-4-(p-tert-butylphenyl)indenyl)-(2-ethyl-4-(p-isopropylphenyl)indenyl)zirconium dichloride,
dimethylsilanediyl(2-cyclohexyl-4-(p-tert-butylphenyl)indenyl)-(2-ethyl-4-(p-sec-butylphenyl)indenyl)zirconium dichloride,
dimethylsilanediyl(2-cyclohexyl-4-(p-tert-butylphenyl)indenyl)-(2-ethyl-4-(p-cyclohexylphenyl)indenyl)zirconium dichloride,
dimethylsilanediyl(2-cyclohexyl-4-(p-tert-butylphenyl)indenyl)-(2-ethyl-4-(p-trimethylsilylphenyl)indenyl)zirconium dichloride,
dimethylsilanediyl(2-cyclohexyl-4-(p-tert-butylphenyl)indenyl)-(2-ethyl-4- (p-adamantylphenyl)indenyl) zirconium dichloride,
dimethylsilanediyl(2-cyclohexyl-4-(p-tert-butylphenyl)indenyl)-(2-ethyl-4-(p-tris(trifluoromethyl)methylphenyl)indenyl)zirconium dichloride, 2-(p-methylcyclohexyl), 4-(p-tert-butylphenyl), 2-ethyl, various substituents in the other 4 position:
dimethylsilanediyl(2-(p-methylcyclohexyl)-4-(p-tert-butylphenyl)-indenyl)(2-ethyl-4-(p-isopropylphenyl)indenyl)zirconium dichloride,
dimethylsilanediyl(2-(p-methylcyclohexyl)-4-(p-tert-butylphenyl)-indenyl)(2-ethyl-4-(p-sec-butylphenyl)indenyl)zirconium dichloride,
dimethylsilanediyl(2-(p-methylcyclohexyl)-4-(p-tert-butylphenyl)-indenyl)(2-ethyl-4-(p-cyclohexylphenyl)indenyl)zirconium dichloride,
dimethylsilanediyl(2-(p-methylcyclohexyl)-4-(p-tert-butylphenyl)-indenyl)(2-ethyl-4-(p-trimethylsilylphenyl)indenyl)zirconium dichloride,
dimethylsilanediyl(2-(p-methylcyclohexyl)-4-(p-tert-butylphenyl)-indenyl)(2-ethyl-4-(p-adamantylphenyl)indenyl)zirconium dichloride,
dimethylsilanediyl(2-(p-methylcyclohexyl)-4-(p-tert-butylphenyl)-indenyl)(2-ethyl-4-(p-tris(trifluoromethyl)methylphenyl)indenyl)-zirconium dichloride, 2-isopropyl, 4-(p-isopropylphenyl), 2-ethyl, various substituents in the other 4 position:
dimethylsilanediyl(2-isopropyl-4-(p-isopropylphenyl)indenyl)(2-ethyl-4-(p-tert-butylphenyl)indenyl)zirconium dichloride,
dimethylsilanediyl(2-isopropyl-4-(p-isopropylphenyl)indenyl)(2-ethyl-4-(p-sec-butylphenyl)indenyl)zirconium dichloride,
dimethylsilanediyl(2-isopropyl-4-(p-isopropylphenyl)indenyl)(2-ethyl-4-(p-cyclohexylphenyl)indenyl)zirconium dichloride,
dimethylsilanediyl(2-isopropyl-4-(p-isopropylphenyl)indenyl)(2-ethyl-4-(p-trimethylsilylphenyl)indenyl)zirconium dichloride,
dimethylsilanediyl(2-isopropyl-4-(p-isopropylphenyl)indenyl)(2-ethyl-4-(p-adamantylphenyl)indenyl)zirconium dichloride,
dimethylsilanediyl(2-isopropyl-4-(p-isopropylphenyl)indenyl)(2-ethyl-4-(p-tris(trifluoromethyl)methylphenyl)indenyl)zirconium dichloride, 2-sec-butyl, 4-(p-isopropylphenyl), 2-ethyl, various substituents in the other 4 position:
dimethylsilanediyl(2-sec-butyl-4-(p-isopropylphenyl)indenyl)(2-ethyl-4-(p-tert-butylphenyl)indenyl)zirconium dichloride,
dimethylsilanediyl(2-sec-butyl-4-(p-isopropylphenyl)indenyl)(2-ethyl-4-(p-sec-butylphenyl)indenyl)zirconium dichloride,
dimethylsilanediyl(2-sec-butyl-4-(p-isopropylphenyl)indenyl)(2-ethyl-4-(p-cyclohexylphenyl)indenyl)zirconium dichloride,
dimethylsilanediyl(2-sec-butyl-4-(p-isopropylphenyl)indenyl)(2-ethyl-4-(p-trimethylsilylphenyl)indenyl)zirconium dichloride,
dimethylsilanediyl(2-sec-butyl-4-(p-isopropylphenyl)indenyl)(2-ethyl-4-(p-adamantylphenyl)indenyl)zirconium dichloride,
dimethylsilanediyl(2-sec-butyl-4-(p-isopropylphenyl)indenyl)(2-ethyl-4-(p-tris(trifluoromethyl)methylphenyl)indenyl)zirconium dichloride, 2-(1-methylbutyl), 4-(p-isopropylphenyl), 2-ethyl, various substituents in the other 4 position:
dimethylsilanediyl(2-(1-methylbutyl)-4-(p-isopropylphenyl)-indenyl)(2-ethyl-4-(p-tert-butylphenyl)indenyl)zirconium dichloride,
dimethylsilanediyl(2-(1-methylbutyl)-4-(p-isopropylphenyl)-indenyl)(2-ethyl-4-(p-sec-butylphenyl)indenyl)zirconium dichloride,
dimethylsilanediyl(2-(1-methylbutyl)-4-(p-isopropylphenyl)-indenyl)(2-ethyl-4-(p-cyclohexylphenyl)indenyl)zirconium dichloride,
dimethylsilanediyl(2-(1-methylbutyl)-4-(p-isopropylphenyl)-indenyl)(2-ethyl-4-(p-trimethylsilylphenyl)indenyl)zirconium dichloride,
dimethylsilanediyl(2-(1-methylbutyl)-4-(p-isopropylphenyl)-indenyl)(2-ethyl-4-(p-adamantylphenyl)indenyl)zirconium dichloride,
dimethylsilanediyl(2-(1-methylbutyl)-4-(p-isopropylphenyl)-indenyl)(2-ethyl-4-(p-tris(trifluoromethyl)methylphenyl)indenyl)-zirconium dichloride, 2-cyclopentyl, 4-(p-isopropylphenyl), 2-ethyl, various substituents in the other 4 position:
dimethylsilanediyl(2-cyclopentyl-4-(p-isopropylphenyl)indenyl)-(2-ethyl-4- (p-tert-butylphenyl)indenyl) zirconium dichloride,
dimethylsilanediyl(2-cyclopentyl-4-(p-isopropylphenyl)indenyl)-(2-ethyl-4-(p-sec-butylphenyl)indenyl)zirconium dichloride,
dimethylsilanediyl(2-cyclopentyl-4-(p-isopropylphenyl)indenyl)-(2-ethyl-4-(p-cyclohexylphenyl)indenyl)zirconium dichloride,
dimethylsilanediyl(2-cyclopentyl-4-(p-isopropylphenyl)indenyl)-(2-ethyl-4-(p-trimethylsilylphenyl)indenyl)zirconium dichloride, dimethylsilanediyl(2-cyclopentyl-4-(p-isopropylphenyl)indenyl)-(2-ethyl-4-(p-adamantylphenyl)indenyl)zirconium dichloride,
dimethylsilanediyl(2-cyclopentyl-4-(p-isopropylphenyl)indenyl)-(2-ethyl-4-(p-tris(trifluoromethyl)methylphenyl)indenyl)zirconium dichloride,
  2-cyclohexyl, 4-(p-isopropylphenyl), 2-ethyl, various substituents in the other 4 position:
dimethylsilanediyl(2-cyclohexyl-4-(p-isopropylphenyl)indenyl)(2-ethyl-4-(p-tert-butylphenyl)indenyl)zirconium dichloride,
dimethylsilanediyl(2-cyclohexyl-4-(p-isopropylphenyl)indenyl)(2-ethyl-4-(p-sec-butylphenyl)indenyl)zirconium dichloride,
dimethylsilanediyl(2-cyclohexyl-4-(p-isopropylphenyl)indenyl)(2-ethyl-4-(p-cyclohexylphenyl)indenyl)zirconium dichloride,
dimethylsilanediyl(2-cyclohexyl-4-(p-isopropylphenyl)indenyl)(2-ethyl-4-(p-trimethylsilylphenyl)indenyl)zirconium dichloride,
dimethylsilanediyl(2-cyclohexyl-4-(p-isopropylphenyl)indenyl)(2-ethyl-4-(p-adamantylphenyl)indenyl)zirconium dichloride,
dimethylsilanediyl(2-cyclohexyl-4-(p-isopropylphenyl)indenyl)(2-ethyl-4-(p-tris(trifluoromethyl)methylphenyl)indenyl)zirconium dichloride,
  2-(p-methylcyclohexyl), 4-(p-isopropylphenyl), 2-ethyl, various substituents in the other 4 position:
dimethylsilanediyl(2-(p-methylcyclohexyl)-4-(p-isopropylphenyl)-indenyl)(2-ethyl-4-(p-tert-butylphenyl)indenyl)zirconium dichloride,
dimethylsilanediyl(2-(p-methylcyclohexyl)-4-(p-isopropylphenyl)-indenyl)(2-ethyl-4-(p-sec-butylphenyl)indenyl)zirconium dichloride,
dimethylsilanediyl(2-(p-methylcyclohexyl)-4-(p-isopropylphenyl)-indenyl)(2-ethyl-4-(p-cyclohexylphenyl)indenyl)zirconium dichloride,
dimethylsilanediyl(2-(p-methylcyclohexyl)-4-(p-isopropylphenyl)-indenyl)(2-ethyl-4-(p-trimethylsilylphenyl)indenyl)zirconium dichloride,
dimethylsilanediyl(2-(p-methylcyclohexyl)-4-(p-isopropylphenyl)-indenyl)(2-ethyl-4-(p-adamantylphenyl)indenyl)zirconium dichloride,
dimethylsilanediyl(2-(p-methylcyclohexyl)-4-(p-isopropylphenyl)-indenyl)(2-ethyl-4-(p-tris(trifluoromethyl)methylphenyl)indenyl)-zirconium dichloride,
  2-isopropyl, 4-(p-sec-butyl), 2-ethyl, various substituents in the other 4 position:
dimethylsilanediyl(2-isopropyl-4-(p-sec-butyl)indenyl)(2-ethyl-4-(p-tert-butylphenyl)indenyl)zirconium dichloride,
dimethylsilanediyl(2-isopropyl-4-(p-sec-butyl)indenyl)(2-ethyl-4-(p-isopropylphenyl)indenyl)zirconium dichloride,
dimethylsilanediyl(2-isopropyl-4-(p-sec-butyl)indenyl)(2-ethyl-4-(p-cyclohexylphenyl)indenyl)zirconium dichloride,
dimethylsilanediyl(2-isopropyl-4-(p-sec-butyl)indenyl)(2-ethyl-4-(p-trimethylsilylphenyl)indenyl)zirconium dichloride,
dimethylsilanediyl(2-isopropyl-4-(p-sec-butyl)indenyl)(2-ethyl-4-(p-adamantylphenyl)indenyl)zirconium dichloride,
dimethylsilanediyl(2-isopropyl-4-(p-sec-butyl)indenyl)(2-ethyl-4-(p-tris(trifluoromethyl)methylphenyl)indenyl)zirconium dichloride,
  2-sec-butyl, 4-(p-sec-butyl), 2-ethyl, various substituents in the other 4 position:
dimethylsilanediyl(2-sec-butyl-4-(p-sec-butyl)indenyl)(2-ethyl-4-(p-tert-butylphenyl)indenyl)zirconium dichloride,
dimethylsilanediyl(2-sec-butyl-4-(p-sec-butyl)indenyl)(2-ethyl-4-(p-isopropylphenyl)indenyl)zirconium dichloride,
dimethylsilanediyl(2-sec-butyl-4-(p-sec-butyl)indenyl)(2-ethyl-4-(p-cyclohexylphenyl)indenyl)zirconium dichloride,
dimethylsilanediyl(2-sec-butyl-4-(p-sec-butyl)indenyl)(2-ethyl-4-(p-trimethylsilylphenyl)indenyl)zirconium dichloride,
dimethylsilanediyl(2-sec-butyl-4-(p-sec-butyl)indenyl)(2-ethyl-4-(p-adamantylphenyl)indenyl)zirconium dichloride,
dimethylsilanediyl(2-sec-butyl-4-(p-sec-butyl)indenyl)(2-ethyl-4-(p-tris(trifluoromethyl)methylphenyl)indenyl)zirconium dichloride,
  2-(1-methylbutyl), 4-(p-sec-butyl), 2-ethyl, various substituents in the other 4 position:
dimethylsilanediyl(2-(1-methylbutyl)-4-(p-sec-butyl)indenyl)(2-ethyl-4-(p-tert-butylphenyl)indenyl)zirconium dichloride,
dimethylsilanediyl(2-(1-methylbutyl)-4-(p-sec-butyl)indenyl)(2-ethyl-4-(p-isopropylphenyl)indenyl)zirconium dichloride,
dimethylsilanediyl(2-(1-methylbutyl)-4-(p-sec-butyl)indenyl)(2-ethyl-4-(p-cyclohexylphenyl)indenyl)zirconium dichloride,
dimethylsilanediyl(2-(1-methylbutyl)-4-(p-sec-butyl)indenyl)(2-ethyl-4-(p-trimethylsilylphenyl)indenyl)zirconium dichloride,
dimethylsilanediyl(2-(1-methylbutyl)-4-(p-sec-butyl)indenyl)(2-ethyl-4-(p-adamantylphenyl)indenyl)zirconium dichloride,
dimethylsilanediyl(2-(1-methylbutyl)-4-(p-sec-butyl)indenyl)(2-ethyl-4-(p-tris(trifluoromethyl)methylphenyl)indenyl)zirconium dichloride,
  2-cyclopentyl, 4-(p-sec-butyl), 2-ethyl, various substituents in the other 4 position:
dimethylsilanediyl(2-cyclopentyl-4-(p-sec-butyl)indenyl)(2-ethyl-4-(p-tert-butylphenyl)indenyl)zirconium dichloride,
dimethylsilanediyl(2-cyclopentyl-4-(p-sec-butyl)indenyl)(2-ethyl-4-(p-isopropylphenyl)indenyl)zirconium dichloride,
dimethylsilanediyl(2-cyclopentyl-4-(p-sec-butyl)indenyl)(2-ethyl-4-(p-cyclohexylphenyl)indenyl)zirconium dichloride,
dimethylsilanediyl(2-cyclopentyl-4-(p-sec-butyl)indenyl)(2-ethyl-4-(p-trimethylsilylphenyl)indenyl)zirconium dichloride,
dimethylsilanediyl(2-cyclopentyl-4-(p-sec-butyl)indenyl)(2-ethyl-4-(p-adamantylphenyl)indenyl)zirconium dichloride,
dimethylsilanediyl(2-cyclopentyl-4-(p-sec-butyl)indenyl)(2-ethyl-4-(p-tris(trifluoromethyl)methylphenyl)indenyl)zirconium dichloride,
  2-cyclohexyl, 4-(p-sec-butyl), 2-ethyl, various substituents in the other 4 position:
dimethylsilanediyl(2-cyclohexyl-4-(p-sec-butyl)indenyl)(2-ethyl-4-(p-tert-butylphenyl)indenyl)zirconium dichloride,
dimethylsilanediyl(2-cyclohexyl-4-(p-sec-butyl)indenyl)(2-ethyl-4-(p-isopropylphenyl)indenyl)zirconium dichloride,
dimethylsilanediyl(2-cyclohexyl-4-(p-sec-butyl)indenyl)(2-ethyl-4-(p-cyclohexylphenyl)indenyl)zirconium dichloride, dimethylsilanediyl(2-cyclohexyl-4-(p-sec-butyl)indenyl)(2-ethyl-4-(p-trimethylsilylphenyl)indenyl)zirconium dichloride,
dimethylsilanediyl(2-cyclohexyl-4-(p-sec-butyl)indenyl)(2-ethyl-4-(p-adamantylphenyl)indenyl)zirconium dichloride,
dimethylsilanediyl(2-cyclohexyl-4-(p-sec-butyl)indenyl)(2-ethyl-4-(p-tris(trifluoromethyl)methylphenyl)indenyl)zirconium dichloride,
2-(p-methylcyclohexyl), 4-(p-sec-butyl), 2-ethyl, various substituents in the other 4 position:
dimethylsilanediyl(2-(p-methylcyclohexyl)-4-(p-sec-butyl)-indenyl)(2-ethyl-4-(p-tert-butylphenyl)indenyl)zirconium dichloride,
dimethylsilanediyl(2-(p-methylcyclohexyl)-4-(p-sec-butyl)-indenyl)(2-ethyl-4-(p-isopropylphenyl)indenyl)zirconium dichloride,
dimethylsilanediyl(2-(p-methylcyclohexyl)-4-(p-sec-butyl)-indenyl)(2-ethyl-4-(p-cyclohexylphenyl)indenyl)zirconium dichloride,
dimethylsilanediyl(2-(p-methylcyclohexyl)-4-(p-sec-butyl)-indenyl)(2-ethyl-4-(p-trimethylsilylphenyl)indenyl)zirconium dichloride,
dimethylsilanediyl(2-(p-methylcyclohexyl)-4-(p-sec-butyl)-indenyl)(2-ethyl-4-(p-adamantylphenyl)indenyl)zirconium dichloride,
dimethylsilanediyl(2-(p-methylcyclohexyl)-4-(p-sec-butyl)-indenyl)(2-ethyl-4-(p-tris(trifluoromethyl)methylphenyl)indenyl)-zirconium dichloride,
and also the corresponding dimethylgermanediyl-, ethylidene-, 1-methylethylidene-, 1,1-dimethylethylidene-, 1,2-dimethylethylidene-, 1,1,2,2-tetramethylethylidene-, dimethylmethylidene-, phenylmethylmethylidene- and diphenylmethylidene-bridged compounds.

Possible methods of preparing metallocenes of the formula I are described, for example, in Journal of Organometallic Chem. 288 (1985) 63-67, and in the documents cited therein.

Selected metallocenes, particularly those which have specifically different substituents in position 2 and position 4 on the indenyl ligand, achieve the object of the present invention particularly well.

The present invention accordingly also provides compounds of the formula (IIa)

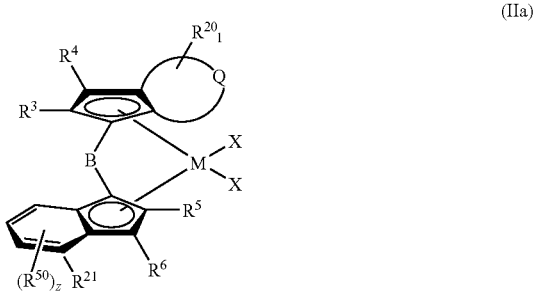

where
M is Ti, Zr or Hf, particularly preferably zirconium,
$R^3$ is a hydrogen atom or a $C_1$-$C_{20}$ group, preferably $C_1$-$C_{18}$-alkyl such as methyl, ethyl, n-butyl, n-hexyl or octyl, $C_2$-$C_{10}$-alkenyl, $C_3$-$C_{15}$-alkylalkenyl, $C_7$-$C_{20}$-arylalkyl, fluorinated $C_1$-$C_{12}$-alkyl, fluorinated $C_6$-$C_{18}$-aryl, fluorinated $C_7$-$C_{20}$-arylalkyl or fluorinated $C_7$-$C_{20}$-alkylaryl,
$R^5$ is different from $R^3$ and is sec-butyl, isopropyl, 1-methylbutyl, 1-methylpentyl, cyclopentyl or cyclohexyl, $R^4$, $R^6$, $R^{50}$ are identical or different and are each a hydrogen atom or a $C_1$-$C_{20}$ group, preferably $C_1$-$C_{18}$-alkyl such as methyl, ethyl, n-butyl, cyclohexyl or octyl, $C_2$-$C_{10}$-alkenyl, $C_3$-$C_{15}$-alkylalkenyl, $C_6$-$C_{18}$-aryl, $C_5$-$C_{18}$-heteroaryl, $C_7$-$C_{20}$-arylalkyl, $C_7$-$C_{20}$-alkylaryl, fluorinated $C_1$-$C_{12}$-alkyl, fluorinated $C_6$-$C_{18}$-aryl, fluorinated $C_7$-$C_{20}$-arylalkyl or fluorinated $C_7$-$C_{20}$-alkylaryl,
$R^{20}$, $R^{21}$ are identical or different and are each a $C_6$-$C_{18}$-aryl group which may be substituted, in particular phenyl, tolyl, xylyl, tert-butylphenyl, 3,5-dimethylphenyl, 3,5-di-tert-butylphenyl, 4-ethylphenyl, 4-trimethylsilylphenyl, methoxyphenyl, naphthyl, acenaphthyl, phenanthrenyl or anthracenyl, $C_5$-$C_{18}$-heteroaryl, $C_7$-$C_{20}$-arylalkyl, $C_7$-$C_{20}$-alkylaryl, fluorinated $C_6$-$C_{18}$-aryl, fluorinated $C_7$-$C_{20}$-arylalkyl or fluorinated $C_7$-$C_{20}$-alkylaryl and two radicals $R^{20}$ or $R^{21}$ may form a monocyclic or polycyclic ring system which may in turn be substituted, where $R^{20}$ and $R^{21}$ must not at the same time be naphthyl, phenyl, phenanthrenyl or anthracenyl or mixtures of naphthyl and phenyl,
X is a halogen atom, in particular chlorine, an alkyl group, in particular methyl, or a substituted or unsubstituted phenoxide,
Q is a $C_4$-$C_{24}$-aryl ring system which may in turn bear $R^{20}$ groups as substituents, a heteroaryl group which together with the cyclopentadienyl ring form an azapentalene, thiapentalene or phosphapentalene which may in turn be substituted by $R^{20}$,
z is 0, 1, 2 or 3,
l is an integer from zero to 4, preferably 1 or 2, particularly preferably 1,
B is a bridging structural element between the two indenyl radicals,
with the exception of rac-Me$_2$Si[2-i-Pr-4-(1-naphthyl)ind)(2'-Me-4'PhInd)]ZrCl$_2$, rac-Me$_2$Si[2-i-Pr-4-(1-naphthyl)ind)(2'-Me-4',5'-BenzInd)]ZrCl$_2$, rac-Me$_2$Si[2-i-Pr-4-(1-naphthyl)ind)(2'-Me-4',5'-BenzInd)]ZrCl$_2$, rac-Me$_2$Si[2-i-Pr-4-phenylind(2'-ethyl-4'-PhInd)]ZrCl$_2$, rac-Me$_2$Si[2-i-Pr-4-(1-naphthylind)(2'-ethyl-4' PhInd)]ZrCl$_2$, rac-Me$_2$Si[2-i-Pr-4-PhInd(2'-ethyl-4'-(1-naphthyl)ind)]ZrCl$_2$, rac-Me$_2$Si[2-i-Pr-4-PhInd(2'-Me-4'-PhInd)]ZrCl$_2$, rac-Me$_2$Si[2-i-Pr-4-(1-naphthyl)ind)(2'-ethyl-4',5'-BenzInd)]ZrCl$_2$, rac-Me$_2$Si[2-i-Pr-4-PhInd)(2'-methyl-4'-(1-naphthyl)Ind)]ZrCl$_2$ and rac-Me$_2$Si[2-i-Pr-4(1-naphthyl)Ind (2'-methyl-4'-(1-naphthyl)Ind)]ZrCl$_2$.

Examples of B are groups $M^3R^{13}R^{14}$, where $M^3$ is silicon and $R^{13}$ and $R^{14}$ are identical or different and are each a $C_1$-$C_{20}$ group such as $C_1$-$C_{10}$-alkyl, $C_6$-$C_{14}$-aryl, trialkylsilyl, in particular trimethylsilyl, triarylsilyl or alkylarylsilyl. Particularly preferred groups for B are Si(Me)$_2$, Si(Ph)$_2$, Si(MeEt), Si(PhMe), Si(PhEt), Si(Et)$_2$, where Ph is substituted or unsubstituted phenyl and Et is ethyl. It is also possible for B together with one or more radicals $R^7$ or $R^8$ to form a monocyclic or polycyclic ring system.

Very particular preference is given to bridged metallocene compounds of the formula (II)

in which
M is zirconium,
$R^3$ is a hydrogen atom or a $C_1$-$C_{12}$-alkyl group, preferably an alkyl group such as methyl, ethyl, n-butyl, n-hexyl or octyl, particularly preferably methyl or ethyl,
$R^5$ is sec-butyl, isopropyl, 1-methylbutyl, 1-methylpentyl, cyclopentyl, cyclohexyl,
$R^4$, $R^6$, $R^{50}$ are hydrogen atoms,
$R^{20}$, $R^{21}$ are identical or different and substitute the indenyl ring in the 4 position and are each a $C_6$-$C_{18}$-aryl group which may be substituted, in particular phenyl, tolyl, xylyl, tert-butylphenyl, 3,5-dimethylphenyl, 3,5-di-tert-butylphenyl, 4-ethylphenyl, 4-trimethylsilylphenyl, methoxyphenyl, naphthyl, acenaphthyl, phenanthrenyl or anthracenyl, $C_5$-$C_{18}$-heteroaryl, $C_7$-$C_{20}$-arylalkyl, $C_7$-$C_{20}$-alkylaryl, fluorinated $C_6$-$C_{18}$-aryl, fluorinated $C_7$-$C_{20}$-arylalkyl or fluorinated $C_7$-$C_{20}$-alkylaryl and two radicals $R^{20}$ or $R^{21}$ may form a monocylic or polycyclic ring system which may in turn be substituted, where $R^{20}$ and $R^{21}$ must not at the same time be naphthyl, phenyl, phenanthrenyl or anthracenyl or mixtures of naphthyl and phenyl, X is chlorine, methyl, Q is a butadienediyl group which together with the cyclopentadienyl ring forms an indenyl system which may in turn bear $R^{20}$ groups as substituents, heteroaryl which together with the cyclopentadienyl ring forms an azapentalene, thiapentalene or phosphapentalene which may in turn be substituted by $R^{20}$, l is an integer from zero to 4, preferably 1 or 2, particularly preferably 1, B is a bridging structural element between the two indenyl radicals and is preferably $Si(Me)_2$, $Si(Ph)_2$, $Si(Et)_2$, $Si(MePh)$.

The invention further provides ligand systems of the formula (IIa) in which the radicals are defined as in formula (II).

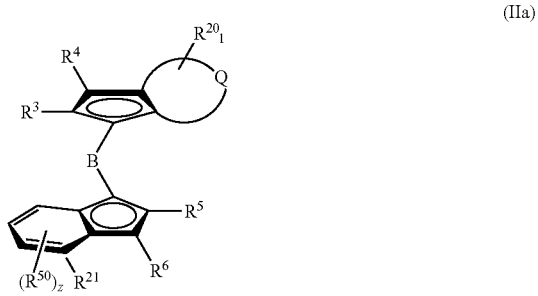

(IIa)

The metallocenes of the present invention having the formulae I and II are highly active catalyst components for the copolymerization of olefins. Depending on the substitution pattern of the ligands, the metallocenes can be obtained as an isomer mixture. The metallocenes are preferably used as pure isomers for the polymerization.

In place of the pure chiral bridged metallocene compounds of the formulae (I) and (II) (pseudo-rac), it is also possible to use mixtures of the metallocenes of the formulae (I) and (II) and the corresponding pseudo-meso metallocenes for preparing the catalyst.

Preference is given to using the pseudo-rac metallocenes of the formulae (I) and (II), but the use of pseudo-rac-enriched rac/meso mixtures is also useful. The terms pseudo-rac and pseudo-meso correspond to the formulae II and IIa disclosed on page 8 of WO 00/31090.

Illustrative but nonlimiting examples of metallocenes of the present invention are:

dimethylsilanediyl(2-methyl-4-(4'-tert-butylphenyl)indenyl)-L-zirconium dichloride
dimethylsilanediyl(2-methyl-4-(3',5'-tert-butylphenyl)indenyl)-L-zirconium dichloride
dimethylsilanediyl(2-methyl-4-(4'-tert-butylphenyl)indenyl)-L-hafnium dichloride
dimethylsilanediyl(2-methyl-4-(4'-tert-butylphenyl)indenyl)-L-titanium dichloride
dimethylsilanediyl(2-methyl-4-(4'-methylphenyl)indenyl)-L-zirconium dichloride
dimethylsilanediyl(2-methyl-4-(4'-ethylphenyl)indenyl)-L-zirconium dichloride
dimethylsilanediyl(2-methyl-4-(4'-n-propyl-phenyl)indenyl)-L-zirconium dichloride
dimethylsilanediyl(2-methyl-4-(4'-isopropylphenyl)indenyl)-L-zirconium dichloride
dimethylsilanediyl(2-methyl-4-(4'-n-butylphenyl)indenyl)-L-zirconium dichloride
dimethylsilanediyl(2-methyl-4-(4'-hexylphenyl)indenyl)-L-zirconium dichloride
dimethylsilanediyl(2-methyl-4-(4'-sec-butylphenyl)indenyl)-L-zirconium dichloride
dimethylsilanediyl(2-methyl-4-phenyl-6-isopropylindenyl)-L-zirconium dichloride
dimethylsilanediyl(2-methyl-4-(1-naphthyl)-6-isopropylindenyl)-L-zirconium dichloride
dimethylsilanediyl(2-methyl-4-(2-naphthyl)-6-isopropylindenyl)-L-zirconium dichloride
dimethylsilanediyl(2-methyl-4-(4'-trimethylsilylphenyl)indenyl)-L-zirconium dichloride
dimethylsilanediyl(2-methyl-4-(4'-adamantylphenyl)indenyl)-L-zirconium dichloride
dimethylsilanediyl(2-methyl-4-acenaphthindenyl)-L-zirconium dichloride
dimethylsilanediyl(2-methyl-4-(2',4',6'-trimethylphenyl)indenyl)-L-zirconium dichloride
dimethylsilanediyl(2-methyl-4-(3',5'-dimethylphenyl)indenyl)-L-zirconium dichloride
dimethylsilanediyl(2-ethyl-4-(3',5'-di-tert-butylphenyl)indenyl)-L-zirconium dichloride
dimethylsilanediyl(2-ethyl-4-(2',4',6'-trimethylphenyl)indenyl)-L-zirconium dichloride
dimethylsilanediyl(2-methyl-4-(4'-trifluoromethylphenyl)indenyl)-L-zirconium dichloride
dimethylsilanediyl(2-methyl-4-(4'-methoxyphenyl)indenyl)-L-zirconium dichloride
dimethylsilanediyl(2-ethyl-4-(4'-tert-butylphenyl)indenyl)-L-zirconium dichloride
dimethylsilanediyl(2-ethyl-4-(4'-trifluoromethylphenyl)indenyl)-L-zirconium dichloride
dimethylsilanediyl(2-ethyl-4-(4'-methoxyphenyl)indenyl)-L-zirconium dichloride
dimethylsilanediyl(2-ethyl-4-phenyl)indenyl-L-zirconium dichloride
dimethylsilanediyl(2-ethyl-4-(4'-methylphenyl)indenyl)-L-zirconium dichloride
dimethylsilanediyl(2-ethyl-4-(4'-ethylphenyl)indenyl)-L-zirconium dichloride
dimethylsilanediyl(2-ethyl-4-(4'-n-propylphenyl)indenyl)-L-zirconium dichloride
dimethylsilanediyl(2-ethyl-4-(4'-isopropylphenyl)indenyl)-L-zirconium dichloride
dimethylsilanediyl(2-ethyl-4-(4'-n-butylphenyl)indenyl)-L-zirconium dichloride
dimethylsilanediyl(2-ethyl-4-(4'-hexylphenyl)indenyl)-L-zirconium dichloride
dimethylsilanediyl(2-ethyl-4-(4'-pentylphenyl)indenyl)-L-zirconium dichloride
dimethylsilanediyl(2-ethyl-4-(4'-cyclohexylphenyl)indenyl)-L-zirconium dichloride
dimethylsilanediyl(2-ethyl-4-(4'-sec-butylphenyl)indenyl)-L-zirconium dichloride
dimethylsilanediyl(2-ethyl-4-(4'-tert-butylphenyl)indenyl)-L-zirconium dichloride
dimethylsilanediyl(2-ethyl-4-(9-phenanthryl)indenyl)-L-zirconium dichloride dimethylsilanediyl(2-ethyl-4-phenyl-6-isopropylindenyl)-L-zirconium dichloride
dimethylsilanediyl(2-ethyl-4-(1-naphthyl)-6-isopropylindenyl)-L-zirconium dichloride
dimethylsilanediyl(2-ethyl-4-(2-naphthyl)-6-isopropylindenyl)-L-zirconium dichloride
dimethylsilanediyl(2-ethyl-4-(4'-trimethylsilylphenyl)indenyl)-L-zirconium dichloride
dimethylsilanediyl(2-ethyl-4-(4'-adamantylphenyl)indenyl)-L-zirconium dichloride
dimethylsilanediyl(2-n-propyl-4-phenyl)indenyl-L-zirconium dichloride
dimethylsilanediyl(2-n-propyl-4-(4'-methylphenyl)indenyl)-L-zirconium dichloride
dimethylsilanediyl(2-n-propyl-4-(4'-ethylphenyl)indenyl)-L-zirconium dichloride
dimethylsilanediyl(2-n-propyl-4-(4'-n-propylphenyl)indenyl)-L-zirconium dichloride
dimethylsilanediyl(2-n-propyl-4-(4'-isopropylphenyl)indenyl)-L-zirconium dichloride
dimethylsilanediyl(2-n-propyl-4-(4'-n-butylphenyl)indenyl)-L-zirconium dichloride
dimethylsilanediyl(2-n-propyl-4-(4'-hexylphenyl)indenyl)-L-zirconium dichloride
dimethylsilanediyl(2-n-propyl-4-(4'-cyclohexylphenyl)indenyl)-L-zirconium dichloride
dimethylsilanediyl(2-n-propyl-4-(4'-sec-butylphenyl)indenyl)-L-zirconium dichloride
dimethylsilanediyl(2-n-propyl-4-(4'-tert-butylphenyl)indenyl)-L-zirconium dichloride
dimethylsilanediyl(2-propyl-4-(9-phenanthryl)indenyl)-L-zirconium dichloride
dimethylsilanediyl(2-propyl-4-phenyl-6-isopropylindenyl)-L-zirconium dichloride
dimethylsilanediyl(2-propyl-4-(1-naphthyl)-6-isopropylindenyl)-L-zirconium dichloride
dimethylsilanediyl(2-propyl-4-(2-naphthyl)-6-isopropylindenyl)-L-zirconium dichloride
dimethylsilanediyl(2-propyl-4-(4'-trimethylsilylphenyl)indenyl)-L-zirconium dichloride
dimethylsilanediyl(2-propyl-4-(4'-adamantylphenyl)indenyl)-L-zirconium dichloride
dimethylsilanediyl(2-n-butyl-(4-phenyl)indenyl)-L-zirconium dichloride
dimethylsilanediyl(2-n-butyl-4-(4'-methylphenyl)indenyl)-L-zirconium dichloride
dimethylsilanediyl(2-n-butyl-4-(4'-ethylphenyl)indenyl)-L-zirconium dichloride
dimethylsilanediyl(2-n-butyl-4-(4'-n-propylphenyl)indenyl)-L-zirconium dichloride
dimethylsilanediyl(2-n-butyl-4-(4'-isopropylphenyl)indenyl)-L-zirconium dichloride
dimethylsilanediyl(2-n-butyl-4-(4'-n-butylphenyl)indenyl)-L-zirconium dichloride
dimethylsilanediyl(2-n-butyl-4-(4'-hexylphenyl)indenyl)-L-zirconium dichloride
dimethylsilanediyl(2-n-butyl-4-(4'-cyclohexylphenyl)indenyl)-L-zirconium dichloride
dimethylsilanediyl(2-n-butyl-4-(4'-sec-butylphenyl)indenyl)-L-zirconium dichloride
dimethylsilanediyl(2-n-butyl-4-(4'-tert-butylphenyl)indenyl)-L-zirconium dichloride
dimethylsilanediyl(2-n-butyl-4-(9-phenanthryl)indenyl)-L-zirconium dichloride
dimethylsilanediyl(2-n-butyl-4-phenyl-6-isopropylindenyl)-L-zirconium dichloride
dimethylsilanediyl(2-n-butyl-4-(1-naphthyl)-6-isopropylindenyl)-L-zirconium dichloride
dimethylsilanediyl(2-n-butyl-4-(2-naphthyl)-6-isopropylindenyl)-L-zirconium dichloride
dimethylsilanediyl(2-n-butyl-4-(4'-trimethylsilylphenyl)indenyl)-L-zirconium dichloride
dimethylsilanediyl(2-n-butyl-4-(4'-adamantylphenyl)indenyl)-L-zirconium dichloride
dimethylsilanediyl(2-hexyl-(4-phenyl)indenyl)-L-zirconium dichloride
dimethylsilanediyl(2-hexyl-4-(4'-methylphenyl)indenyl)-L-zirconium dichloride
dimethylsilanediyl(2-hexyl-4-(4'-ethylphenyl)indenyl)-L-zirconium dichloride
dimethylsilanediyl(2-hexyl-4-(4-n-propylphenyl)indenyl)-L-zirconium dichloride
dimethylsilanediyl(2-hexyl-4-(4'-isopropylphenyl)indenyl)-L-zirconium dichloride
dimethylsilanediyl(2-hexyl-4-(4'-n-butylphenyl)indenyl)-L-zirconium dichloride
dimethylsilanediyl(2-hexyl-4-(4'-hexylphenyl)indenyl)-L-zirconium dichloride
dimethylsilanediyl(2-hexyl-4-(4'-cyclohexylphenyl)indenyl)-L-zirconium dichloride
dimethylsilanediyl(2-hexyl-4-(4'-sec-butylphenyl)indenyl)-L-zirconium dichloride
dimethylsilanediyl(2-hexyl-4-(4'-tert-butylphenyl)indenyl)-L-zirconium dichloride
dimethylsilanediyl(2-hexyl-4-(9-phenanthryl)indenyl)-L-zirconium dichloride
dimethylsilanediyl(2-hexyl-4-phenyl-6-isopropylindenyl)-L-zirconium dichloride
dimethylsilanediyl(2-hexyl-4-(1-naphthyl)-6-isopropylindenyl)-L-zirconium dichloride
dimethylsilanediyl(2-hexyl-4-(2-naphthyl)-6-isopropylindenyl)-L-zirconium dichloride
dimethylsilanediyl(2-hexyl-4-(4'-trimethylsilylphenyl)indenyl)-L-zirconium dichloride
dimethylsilanediyl(2-hexyl-4-(4'-adamantylphenyl)indenyl)-L-zirconium dichloride
dimethylsilanediyl(2-methylazapentalene)-L-zirconium dichloride
dimethylsilanediyl(2-methylthiapentalene)-L-zirconium dichloride
dimethylsilanediyl(2-methylphosphapentalene)-L-zirconium dichloride
dimethylsilanediyl(2-ethylazapentalene)-L-zirconium dichloride
dimethylsilanediyl(2-ethylthiapentalene)-L-zirconium dichloride
dimethylsilanediyl(2-ethylphosphapentalene)-L-zirconium dichloride.

Here, L can be 2-isopropyl-4,5-benzindenyl; 2-isopropyl-4-(4'-tert-butylphenyl)indenyl;
2-sec-butyl-4-(4'-tert-butylphenyl)indenyl;
2-isopropyl-4-phenylindenyl; 2-isopropyl-4-(2-naphthyl)indenyl;
2-isopropyl-4-(1-naphthyl)indenyl; 2-sec-butyl-4-phenylindenyl;
2-sec-butyl-4-phenylindenyl [sic];2-sec-butyl-4,5-benzindenyl;
2-sec-butyl-4-(2-naphthyl)indenyl;
2-sec-butyl-4-(1-naphthyl)indenyl;
2-(1-methylpentyl)-4,5-benzindenyl;
2-(1-methylpentyl)-4-(4'-tert-butylphenyl)indenyl;
2-(1-methylbutyl)-4-phenylindenyl;
2-isopentyl-4-(2-naphthyl)indenyl;

2-(1-methylbutyl)-4-(1-naphthylindenyl);
2-(1-methylbutyl)-4,5-benzindenyl;
2-(1-methylbutyl)-4-(4'-tert-butylphenyl)indenyl;
2-(1-methylbutyl)-4-phenylindenyl;
2-(1-methylbutyl)-4-(2-naphthyl)indenyl;
2-(1-methylbutyl)-4-(1-naphthyl)indenyl;
2-cyclopentyl-4,5-benzindenyl;
2-cyclopentyl-4-(4'-tert-butylphenyl)indenyl;
2-cyclopentyl-4-phenylindenyl;
2-cyclopentyl-4-(2-naphthylindenyl);
2-cyclopentyl-4-(1-naphthylindenyl);
2-cyclohexyl-4,5-benzindenyl;
2-cyclohexyl-4-(4'-tert-butylphenyl)indenyl;
2-cyclohexyl-4-phenylindenyl; 2-cyclohexyl-4-(2-naphthyl)indenyl;
2-cyclohexyl-4-(1-naphthyl)indenyl;
2-(1-methylbutyl)-4-(acenaphthphenyl)indenyl;
2-(1-methylbutyl)-4-(acenaphthphenyl)indenyl [sic];
2-isopropyl-4-(acenaphthphenyl)indenyl;
2-sec-butyl-4-(acenaphthphenyl)indenyl;
2-(1-methylbutyl)-4-(acenaphthphenyl)indenyl;
2-(1-methylpentyl)-4-(acenaphthphenyl)indenyl;
2-cyclopentyl-4-(acenaphthphenyl)indenyl;
2-cyclohexyl-4-(acenaphthphenyl)indenyl. Also preferred are the corresponding dimethylzirconium compounds, the corresponding η$^4$-butadienezirconium compounds; in addition, preference is given to zirconium fragments as described in German patent application P19854350, and also the corresponding compounds having an Si(Ph)$_2$, Si(MeEt), Si(PhMe), Si(PhEt) and Si(Et)$_2$ bridge.

The novel metallocenes of the formulae I and II are particularly suitable as constituents of catalyst systems for preparing polyolefins by polymerization of at least one olefin in the presence of a catalyst comprising at least one cocatalyst and at least one metallocene.

The cocatalyst which together with a novel metallocene of the formula I or II forms the catalyst system comprises at least one compound such as an aluminoxane or a Lewis acid or an ionic compound which reacts with a metallocene to convert it into a cationic compound.

The cocatalyst component which, in accordance with the present invention, may be present in the catalyst system comprises at least one compound such as an aluminoxane or a Lewis acid or an ionic compound which reacts with a metallocene to convert it into a cationic compound.

As aluminoxane, preference is given to using a compound of the formula (III)

(R AlO)$_n$   (III)

Further suitable aluminoxanes can, for example, be cyclic as in formula (IV)

or linear as in formula (V)

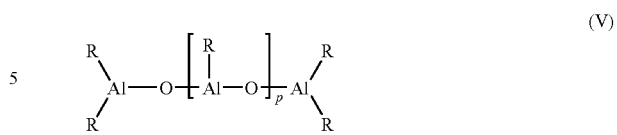

or of the cluster type as in formula (VI)

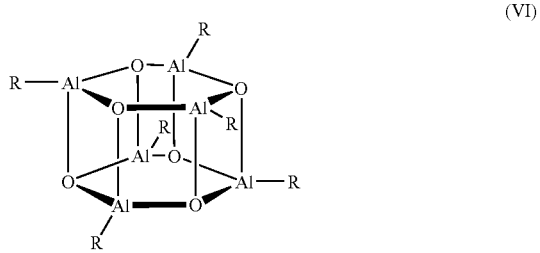

Such aluminoxanes are described, for example, in JACS 117 (1995), 6465-74, organometallics 13 (1994), 2957-2969.

The radicals R in the formulae (III), (IV), (V) and (VI) can be identical or different and can each be a $C_1$-$C_{20}$-hydrocarbon group such as a $C_1$-$C_6$-alkyl group, a $C_6$-$C_{18}$-aryl group, benzyl or hydrogen; p is an integer from 2 to 50, preferably from 10 to 35.

The radicals R are preferably identical and are methyl, isobutyl, n-butyl, phenyl or benzyl, particularly preferably methyl.

If the radicals R are different, they are preferably methyl and hydrogen, methyl and isobutyl or methyl and n-butyl, with hydrogen and/or isobutyl or n-butyl preferably being present in an amount of 0.01-40% (number of radicals R).

The aluminoxane can be prepared in various ways by known methods. One of the methods is, for example, reacting an aluminum-hydrocarbon compound and/or a hydridoaluminum-hydrocarbon compound with water (gaseous, solid, liquid or bound—for example as water of crystallization) in an inert solvent (e.g. toluene).

To prepare an aluminoxane having different alkyl groups R, two different trialkylaluminums (AIR$_3$+AIR'$_3$) corresponding to the desired composition and reactivity are reacted with water (cf. S. Pasynkiewicz, Polyhedron 9 (1990) 429 and EP-A-0,302,424).

Regardless of the method of preparation, all aluminoxane solutions have a varying content of unreacted aluminum starting compound which is present in free form of as adduct.

As Lewis acids, preference is given to using at least one organoboron or organoaluminum compound containing organic $C_1$-$C_{20}$ groups such as branched or unbranched alkyl or haloalkyl, e.g. methyl, propyl, isopropyl, isobutyl, trifluoromethyl, unsaturated groups such as aryl or haloaryl, e.g. phenyl, tolyl, benzyl groups, p-fluorophenyl, 3,5-difluorophenyl, pentachlorophenyl, pentafluorophenyl, 3,4,5-trifluorophenyl and 3,5-di(trifluoromethyl)phenyl.

Examples of Lewis acids are trimethylaluminum, triethylaluminum, triisobutylaluminum, tributylaluminum, trifluoroborane, triphenylborane, tris(4-fluorophenyl)borane, tris (3,5-difluorophenyl)borane, tris(4-fluoromethylphenyl) borane, tris(pentafluorophenyl)borane, tris(tolyl)borane, tris (3,5-dimethylphenyl)borane, tris(3,5-difluorophenyl)borane and/or tris(3,4,5-trifluorophenyl)borane. Particular preference is given to tris(pentafluorophenyl)borane.

As ionic cocatalysts, preference is given to using compounds which contain a noncoordinating anion such as tetrakis(pentafluorophenyl)borate, tetraphenylborate, $SbF_6{-}$, $CF_3SO_3{-}$ or $ClO_4{-}$. As cationic counterion, use is made of Lewis bases such as methylamine, aniline, dimethylamine, diethylamine, N-methylaniline, diphenylamine, N,N-dimethylaniline, trimethylamine, triethylamine, tri-n-butylamine, methyldiphenylamine, pyridine, p-bromo-N,N-dimethylaniline, p-nitro-N,N-dimethylaniline, triethylphosphine, triphenylphosphine, diphenylphosphine, tetrahydrothiophene and triphenylcarbenium.

Examples of such ionic compounds which can be used according to the present invention are triethylammonium tetra(phenyl)borate, tributylammonium tetra(phenyl)borate, trimethylammonium tetra(tolyl)borate, tributylammonium tetra(tolyl)borate, tributylammonium tetra(pentafluorophenyl)borate, tributylammonium tetra(pentafluorophenyl)aluminate, tripropylammonium tetra(dimethylphenyl)borate, tributylammonium tetra(trifluoromethylphenyl)borate, tributylammonium tetra(4-fluorophenyl)borate, N,N-dimethylanilinium tetra(phenyl)borate, N,N-diethylanilinium tetra(phenyl)borate, N,N-dimethylanilinium tetrakis(pentafluorophenyl)borate, N,N-dimethylanilinium tetrakis(pentafluorophenyl)aluminate, N,N-dimethylcyclohexylammonium tetrakis(pentafluorophenyl)borate, N,N-dimethylbenzylammonium tetrakis(pentafluorophenyl)borate, di(propyl)ammonium tetrakis(pentafluorophenyl)borate, di(cyclohexyl)ammonium tetrakis(pentafluorophenyl)borate, triphenylphosphonium tetrakis(phenyl)borate, triethylphosphonium tetrakis(phenyl)borate, diphenylphosphonium tetrakis(phenyl)borate, tri(methylphenyl)phosphonium tetrakis(phenyl)borate, tri(dimethylphenyl)phosphonium tetrakis(phenyl)borate, triphenylcarbenium tetrakis(pentafluorophenyl)borate, triphenylcarbenium tetrakis(pentafluorophenyl)aluminate, triphenylcarbenium tetrakis(phenyl)aluminate, ferrocenium tetrakis(pentafluorophenyl)borate and/or ferrocenium tetrakis(pentafluorophenyl)aluminate.

Preference is given to triphenylcarbenium tetrakis(pentafluorophenyl)borate and/or N,N-dimethylanilinium tetrakis(pentafluorophenyl)borate.

It is also possible to use mixtures of at least one Lewis acid and at least one ionic compound.

Further suitable cocatalyst components are borane or carborane compounds such as: 7,8-dicarbaundecaborane(13), undecahydrido-7,8-dimethyl-7,8-dicarbaundecaborane, dodecahydrido-1-phenyl-1,3-dicarbanonaborane, tri(butyl)ammonium undecahydrido-8-ethyl-7,9-dicarbaundecaborate, 4-carbanonaborane(14), bis(tri(butyl)ammonium) nonaborate, bis(tri(butyl)ammonium) undecaborate, bis(tri(butyl)ammonium) dodecaborate, bis(tri(butyl)ammonium) decachlorodecaborate, tri(butyl)ammonium 1-carbadecaborate, tri(butyl)ammonium 1-carbadodecaborate, tri(butyl)ammonium 1-trimethylsilyl-1-carbadecaborate, tri(buyl)ammonium bis(nonahydrido-1,3-dicarbanonaborato)cobaltate (III), tri(butyl)ammonium bis(undecahydrido-7,8-dicarbaundecaborato)ferrate(III).

Further cocatalyst systems which can be used are combinations of at least one amine and a support with organic element compounds, as described in the patent WO 99/40129.

Preferred cocatalyst systems are the compounds of the formulae (A) and (B),

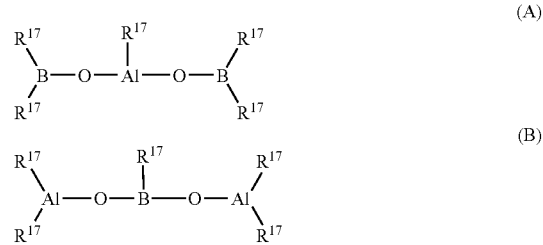

where $R^{17}$ is a hydrogen atom, a halogen atom, a $C_1$-$C_{40}$ group, in particular $C_1$-$C_{20}$-alkyl, $C_1$-$C_{20}$-haloalkyl, $C_1$-$C_{10}$-alkoxy, $C_6$-$C_{20}$-aryl, $C_6$-$C_{20}$-haloaryl, $C_6$-$C_{20}$-aryloxy, $C_7$-$C_{40}$-arylalkyl, $C_7$-$C_{40}$-haloarylalkyl, $C_7$-$C_{40}$-alkylaryl or $C_7$-$C_{40}$-haloalkylaryl. $R^{17}$ can also be an $-OSiR_3$ group, where R are identical or different and are as defined for $R^{17}$ except for a further $-OSiR_3$ group.

Further preferred cocatalysts are compounds in general which are formed by reaction of at least one compound of the formula (C) and/or (D) and/or (E) with at least one compound of the formula (F),

where $R^7$ can be a hydrogen atom or a boron-free $C_1$-$C_{40}$ group such as $C_1$-$C_{20}$-alkyl, $C_6$-$C_{20}$-aryl, $C_7$-$C_{40}$-arylalkyl, $C_7$-$C_{40}$-alkylaryl, and $R^{17}$ is as defined above, X is an element of main group VI of the Periodic Table of the Elements or an NR group, where R is a hydrogen atom or a $C_1$-$C_{20}$-hydrocarbon radical such as $C_1$-$C_{20}$-alkyl or $C_1$-$C_{20}$-aryl, D is an element of main group VI of the Periodic Table of the Elements or an NR group, where R is a hydrogen atom or a $C_1$-$C_{20}$-hydrocarbon radical such as $C_1$-$C_{20}$-alkyl or $C_1$-$C_{20}$-aryl, f is an integer from zero to 3, g is an integer from 0 to 3, with z+y being not equal to 0, h is an integer from 1 to 10.

If desired, the bimetallic compounds are combined with an organometallic compound of the formula VIII $[M^4R^{19}q]k$, where $M^4$ is an element of main group I, II or III of the Periodic Table of the Elements, $R^{19}$ are identical or different and are each a hydrogen atom, a halogen atom or a $C_1$-$C_{40}$ group, in particular a $C_1$-$C_{20}$-alkyl, $C_6$-$C_{40}$-aryl, $C_7$-$C_{40}$-arylalkyl or $C_7$-$C_{40}$-alkylaryl group, q is an integer from 1 to 3 and k is an integer from 1 to 4.

Examples of cocatalytically active compounds of the formulae A and B are:

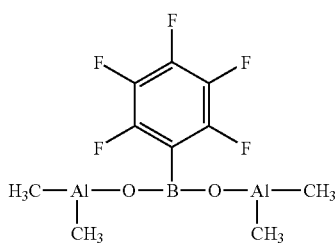

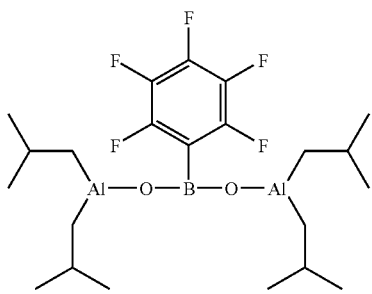

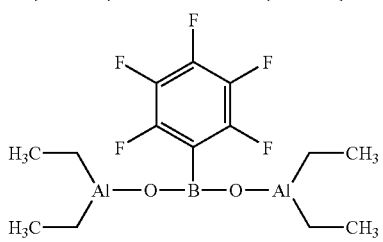

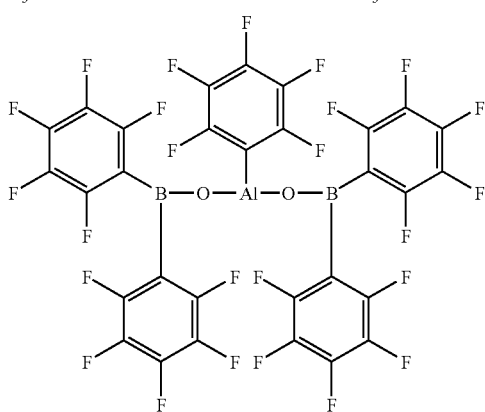

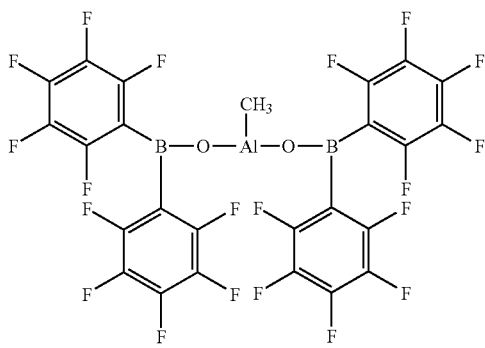

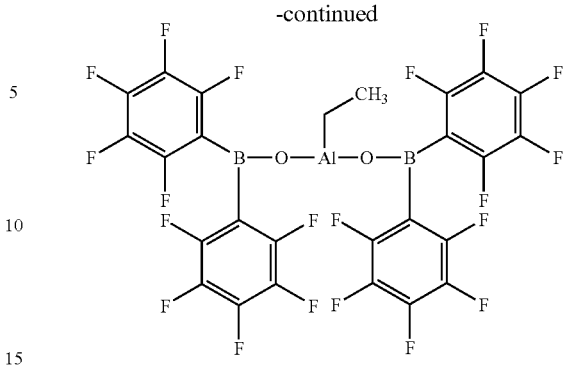

The organometallic compounds of the formula VIII are preferably unchanged Lewis acids in which $M^4$ is lithium, magnesium and/or aluminum, in particular aluminum. Examples of preferred organometallic compounds of the formula VIII are trimethylaluminum, triethylaluminum, triisopropylaluminum, trihexylaluminum, trioctylaluminum, tri-n-butylaluminum, tri-n-propylaluminum, triisoprenylaluminum, dimethylaluminum monochloride, diethylaluminum monochloride, diisobutylaluminum monochloride, methylaluminum sesquichloride, ethylaluminum sesquichloride, dimethylaluminum hydride, diethylaluminum hydride, diisopropylaluminum hydride, dimethylaluminum trimethylsiloxide, dimethylaluminum triethylsiloxide, phenylalanine, pentafluorophenylalane and o-tolylalane.

Further compounds which can be used as cocatalysts, either in unsupported or supported form, are those mentioned in EP-A-924223, DE 19622207.9, EP-A-601830, EP-A-824112, EP-A-824113, WO 99/06414, EP-A-811627, WO97/11775, DE 19606167.9 and DE 19804970.

The support component of the catalyst system of the present invention can be any organic or inorganic, inert solid, in particular a porous support such as talc, inorganic oxides and finely divided polymer powders (e.g. polyolefins).

Suitable inorganic oxides may be found among those of elements of groups 2,3,4,5,13,14,15 and 16 of the Periodic Table of the Elements. Examples of oxides preferred as supports include silicon dioxide, aluminum oxide and also mixed oxides of the elements calcium, aluminum, silicon, magnesium, titanium and corresponding oxide mixtures. Other inorganic oxides which can be used alone or in combination with the last-mentioned preferred oxidic supports are, for example, MgO, $ZrO_2$, $TiO_2$ or $B_2O_3$, to ame only a few.

The support materials used have a specific surface area in the range from 10 to 1000 $m^2/g$, a pore volume in the range from 0.1 to 5 ml/g and a mean particle size of from 1 to 500 µm. Preference is given to supports having a specific surface area in the range from 50 to 500 µm, a pore volume in the range from 0.5 to 3.5 ml/g and a mean particle size in the range from 5 to 350 µm. Particular preference is given to supports having a specific surface area in the range from 200 to 400 $m^2/g$, a pore volume in the range from 0.8 to 3.0 ml/g and a mean particle size of from 10 to 200 µm.

If the support material used naturally has a low moisture content or residual solvent content, dehydration or drying before use can be omitted. If this is not the case, for instance when using silica gel as support material, dehydration or drying is advisable. Thermal dehydration or drying of the support material can be carried out under reduced pressure and under an inert gas blanket (e.g. nitrogen) at the same time.

The drying temperature is in the range from 100 to 1000° C., preferably from 200 to 800° C. In this case, the pressure is not critical. The duration of the drying process can be from 1 to 24 hours. Shorter or longer drying times are possible, provided that equilibrium with the hydroxyl groups on the support surface can be achieved under conditions selected, which normally takes from 4 to 8 hours.

Dehydration or drying of the support material can also be achieved by chemical means, by reacting the adsorbed water and the hydroxyl groups on the surface with suitable passivating agents. The reaction with the passivating reagent enables the hydroxyl groups to be converted completely or partially into a form which leads to no adverse interactions with the catalytically active centers. Suitable passivating agents are, for example, silicon halides and silanes, e.g. silicon tetrachloride, chlorotrimethylsilane, dimethylaminotrichlorosilane, or organometallic compounds of aluminum, boron and magnesium, for example trimethylaluminum, triethylaluminum, triisobutylaluminum, triethylborane, dibutylmagnesium. Chemical dehydration or passivation of the support material is carried out by, for example, reacting a suspension of the support material in a suitable solvent with the passivating reagent in pure form or as a solution in a suitable solvent with exclusion of air and moisture. Suitable solvents are, for example, aliphatic or aromatic hydrocarbons such as pentane, hexane, heptane, toluene or xylene. Passivation is carried out at from 25° C. to 120° C., preferably from 50 to 70° C. Higher and lower temperatures are possible. The reaction time is from 30 minutes to 20 hours, preferably from 1 to 5 hours. After the chemical dehydration is complete, the support material is isolated by filtration under inert conditions, washed one or more times with suitable inert solvents as have been described above and subsequently dried in a stream of inert gas or under reduced pressure.

Organic support materials such as finely divided polyolefin powders (e.g. polyethylene, polypropylene or polystyrene) can also be used and should likewise be freed of adhering moisture, solvent residues or other impurities by appropriate purification and drying operations before use.

To prepare the supported catalyst system, at least one of the above-described metallocene components in a suitable solvent is brought into contact with at least one cocatalyst component, preferably giving a soluble reaction product, an adduct or a mixture.

The preparation obtained in this way is then mixed with the dehydrated or passivated support material, the solvent is removed and the resulting supported metallocene catalyst system is dried in order to ensure that the solvent is completely or largely removed from the pores of the support material. The supported catalyst is obtained as a free-flowing powder.

A process for preparing a free-flowing and, if desired, prepolymerized supported catalyst system comprises the following steps:
  a) preparation of a metallocene/cocatalyst mixture in a suitable solvent or suspension medium, with the metallocene component having one of the above-described structures;
  b) application of the metallocene/cocatalyst mixture to a porous, preferably inorganic dehydrated support;
  c) removal of the major part of the solvent from the resulting mixture;
  d) isolation of the supported catalyst system;
  e) if desired, prepolymerization of the resulting supported catalyst system using one or more olefinic monomer(s) to give a prepolymerized supported catalyst system.

Preferred solvents for the preparation of the metallocene/cocatalyst mixture are hydrocarbons and hydrocarbon mixtures which are liquid at the reaction temperature selected and in which the individual components preferably dissolve. However, the solubility of the individual components is not a prerequisite as long as it is ensured that the reaction product of metallocene and cocatalyst components is soluble in the solvent selected. Examples of suitable solvents include alkanes such as pentane, isopentane, hexane, heptane, octane and nonane; cycloalkanes such as cyclopentane and cyclohexane; and aromatics such as benzene, toluene, ethylbenzene and diethylbenzene. Very particular preference is given to toluene.

The amounts of aluminoxane and metallocene used in the preparation of the supported catalyst system can be varied within a wide range. Preference is given to a molar ratio of aluminum to the transition metal in the metallocene of from 10:1 to 1000:1, very particularly preferably from 50:1 to 500:1.

In the case of methylaluminoxane, preference is given to using 30% strength solutions in toluene; however, the use of 10% strength solutions is also possible.

For the preactivation, the metallocene in the form of a solid is dissolved in a solution of the aluminoxane in a suitable solvent. It is also possible to dissolve the metallocene separately in a suitable solvent and subsequently to combine this solution with the aluminoxane solution. Preference is given to using toluene.

The preactivation time is from 1 minute to 200 hours.

The preactivation can take place at room temperature (25° C.). In particular cases, the use of higher temperatures can shorten the preactivation time required and effect an additional increase in the activity. In this case, the expression higher temperatures refers to a range from 50 to 100° C.

The preactivated solution or the metallocene/cocatalyst mixture is subsequently combined with an inert support material, usually silica gel, which may be in the form of a dry powder or as a suspension in one of the abovementioned solvents. The support aterial is preferably used as powder. The order of addition is immaterial. The preactivated metallocene/cocatalyst solution or he metallocene/cocatalyst mixture can be added to the support aterial or else the support material can be introduced into the solution.

The volume of the preactivated solution or of the metallocene/cocatalyst mixture can exceed 100% of the total pore volume of the support material used or else can be up to 100% of the total pore volume.

The temperature at which the preactivated solution or the metallocene/cocatalyst mixture is brought into contact with the support material can vary in a range from 0 to 100° C. However, lower or higher temperatures are also possible.

Subsequently, the solvent is completely or mostly removed from the supported catalyst system, during which the mixture can be stirred and, if desired, also heated. Preference is given to removing both the visible proportion of the solvent. and also the proportion in the pores of the support material. The removal of the solvent can be carried out in a conventional way with use of reduced pressure and/or flushing with inert gas. During the drying procedure, the mixture can be heated until the free solvent has been removed, which usually takes from 1 to 3 hours at a preferred temperature in the range from 30 to 60° C. The free solvent is the visible proportion of solvent in the mixture. In the present context, residual solvent is the proportion enclosed in the pores.

As an alternative to complete removal of the solvent, it is also possible to dry the supported catalyst system only to a particular residual solvent content, with the free solvent having been completely removed. The supported catalyst system can subsequently be washed with a low-boiling hydrocarbon such as pentane or hexane and dried again.

The supported catalyst system prepared according to the present invention can either be used directly for the polymerization of olefins or can be prepolymerized using one or more olefinic monomers prior to its use in a polymerization process. The procedure for prepolymerizing supported catalyst systems is described, for example, in WO 94/28034.

As additive, it is possible to add a small amount of an olefin, preferably an α-olefin (for example vinylcyclohexane, styrene or phenyldimethylvinylsilane), as modifying component or an antistatic (as described in U.S. Ser. No. 08/365,280 now abandoned) during or after the preparation of the supported catalyst system. The molar ratio of additive to metallocene component compound I is preferably from 1:1000 to 1000:1, very particularly preferably from 1:20 to 20:1.

The present invention also provides a process for preparing a polyolefin by polymerization of one or more olefins in the presence of the catalyst system of the present invention comprising at least one transition metal component of the formula I. For the purposes of the present invention, the term polymerizaton refers to both homopolymerization and copolymerization.

Preference is given to polymerizing olefins of the formula $R_m$—CH=CH—$R_n$, where $R_m$ and $R_n$ are identical or different and are each a hydrogen atom or an organic radical having from 1 to 20 carbon atoms, in particular from 1 to 10 carbon atoms, and $R_m$ and $R_n$ together with the atoms connecting them may form one or more rings.

Examples of such olefins are 1-olefins having 2-20, preferably from 2 to 10, carbon atoms, e.g. ethene, propene, 1-butene, 1-pentene, 1-hexene, 4-methyl-1-pentene or 1-octene, styrene, dienes such as 1,3-butadiene, 1,4-hexadiene, vinylnorbornene, norbornadiene or ethylnorbornadiene and cyclic olefins such as norbornene, tetracyclododecene or methylnorbornene. In the process of the present invention, preference is given to homopolymerizing propene or ethene or copolymerizing propene with ethene and/or with one or more 1-olefins having from 4 to 20 carbon atoms, e.g. butene, hexene or vinylcyclohexane, and/or one or more dienes having from 4 to 20 carbon atoms, e.g. 1,4-butadiene, norbornadiene, ethylidenenorbornene or ethylnorbornadiene. Examples of such copolymers are ethene-propene copolymers or ethene-propene-1,4-hexadiene terpolymers.

The polymerization is carried out at from 0 to 300° C., preferably from 50 to 200° C., very particularly preferably 50-80° C. The pressure is from 0.5 to 2000 bar, preferably from 5 to 64 bar.

The polymerization can be carried out in solution, in bulk, in suspension or in the gas phase, continuously or batchwise, in one or more stages.

The catalyst system prepared according to the present invention can be used as sole catalyst component for the polymerization of olefins having from 2 to 20 carbon atoms, but is preferably used in combination with at least one alkyl compound of elements of main groups I to III of the Periodic Table, e.g. an aluminum, magnesium or lithium alkyl or an aluminoxane. The alkyl compound is added to the monomer or suspension medium and serves to free the monomer of substances which can adversely affect the catalyst activity. The amount of alkyl compound added depends on the quality of the monomers used.

As molar mass regulator and/or to increase the activity, hydrogen is added if necessary.

The catalyst system can be introduced in pure form into the polymerization system or can be admixed with inert components such as paraffins, oils or waxes to allow better metering. Furthermore, an antistatic can be metered into the polymerization system either together with or separately from the catalyst system used.

The polymers (also (co)polymers of the present invention below) prepared using the catalyst system of the present invention have a uniform particle morphology and contain no fines. No deposits or caked material are obtained in the polymerization using the catalyst system of the present invention.

The (co)polymers of the present invention include both homopolymers and random copolymers of polypropylene. Their molar mass $M_w$ (measured using gel permeation chromatography) is in the range from 100 000 to 1 000 000 g/mol and their $M_w/M_n$ (measured using gel permeation chromatography) is in the range from 1.8 to 4.0, preferably from 1.8 to 3.5. Random copolymers of propylene comprise subordinate amounts of monomers which can be copolymerized with propylene, for example $C_2$-$C_8$-alk-1-enes such as ethylene, 1-butene, 1-pentene, 1-hexene or 4-methyl-1-pentene. It is also possible to use two or more different comonomers; this then gives, for example, random terpolymers.

Homopolymers of propylene or copolymers of propylene with up to 50% by weight of other copolymerized 1-alkenes having up to 8 carbon atoms are particularly useful. The copolymers of propylene are random copolymers or block or impact copolymers. If the copolymers of propylene have a random structure, they generally contain up to 50% by weight, preferably up to 15% by weight, particularly preferably up to 1% by weight, of other 1-alkenes having up to 8 carbon atoms, in particular ethylene, 1-butene, 4-methyl-1-pentene or a mixture of ethylene and 1-butene, ethylene and 1-hexene or ethylene and 4-methyl-1-pentene.

The random copolymer of propylene may be a random propylene-ethylene copolymer having an ethylene content of from 0.01 to 50% by weight, a molar mass $M_w$ (measured using gel permeation chroma-tography) in the range from 100 000 to 1 000 000 g/mol, an $M_w/M_n$ (measured using gel permeation chromatography) in the range from 1.8 to 4.0, a ratio of the intensities of the signal for $C^1$ to the sum of the intensities of the signals for $C^{15}$ and $C^{16}$ (in each case determined from the 13C-NMR spectrum of the random copolymer of the present invention) of more than 100, a ratio of the intensities of the signal for $C^7$ to the sum of the intensities of the signals for $C^9$ and $C^{10}$ (in each case determined from the 13C-NMR spectrum of the random copolymer of the present invention) of more than 0.1. Particular random propyleneethylene copolymers of this type have a difference in ethylene content between copolymer fractions of differing molar masses of not more than 10% by weight (determined by TREF as described in the experimental section).

The copolymers of the present invention also include block or impact copolymers of propylene, in the case of which a propylene homopolymer, e.g. one according to the present invention, or a random copolymer according to the present invention of propylene with from 0.001 to 15% by weight, preferably from 0.01 to 6% by weight, of other 1-alkenes having up to 8 carbon atoms (e.g. ethylene, 1-butene, 1-hexene, 1-octene, 4-methyl-1-pentene) is prepared in the first stage and a propylene-ethylene copolymer which has an ethylene content of from 15 to 80% by weight and may further comprise additional $C_4$-$C_8$-alk-1-enes (e.g. ethylene, 1-butene, 1-hexene, 1-octene, 4-methyl-1-pentene) is then polymerized onto this in the second stage. In general, the amount of the propylene-ethylene copolymer (which may contain ethylene, 1-butene, 1-hexene, 1-octene, 4-methyl-1-pentene as further monomers) polymerized on is such that the copolymer produced in the second stage is present in a proportion of from 3 to 60% by weight in the end product.

Propylene homopolymers and copolymers of the present invention have a content of meso-configured diads (measured using 13C-NMR spectroscopy, see examples) of at least 90%, preferably at least 95% and particularly preferably at least 98%.

Random copolymers of the present invention have a minimum content of 2,1 insertions (measured using 13C-NMR spectroscopy, see examples) of propene monomers ((intrachain) reverse insertions). The random copolymers of the present invention have at least four, preferably at least six and particularly preferably at least 7.5, (intra-chain) reverse insertions per polymer chain. This property of the copolymers of the present invention is at present explained by the following mechanistic theory, although its correctness does not impose a restriction on the subject matter of the invention: random copolymers which are not according to the present invention are produced using single-site catalysts (e.g. metallocene catalysts) which allow the growing polymer chain to be terminated on a coordinated ethylene after a reverse insertion. This reaction route leads to a cis-2-butenyl end group (which can be reduced to an n-butyl group by the hydrogen which may be present in the reactor) and to a low content of (intrachain) reverse insertions. This mechanism generally leads directly to decreasing molar masses with increasing ethylene content. In the case of the copolymers of the present invention, the catalyst system of the present invention suppresses the indicated chain termination mechanism, so that chain continuation follows reverse insertions. This leads directly to copolymers whose molar mass increases with increasing ethylene content.

Random copolymers produced using single-site catalysts (e.g. metallocene catalysts) are distinguished from, for example, Ziegler-Natta catalyzed copolymers having a comparable comonomer content by a series of properties.

Thus, single-site-catalyzed copolymers have a uniform comonomer distribution over their molar mass spectrum. Such a distribution can be determined, for example, by means of coupled GPC-IR measurement.

In single-site-catalyzed copolymers, the comonomers are randomly distributed, while Ziegler-Natta-catalyzed copolymers tend to incorporate the comonomer in blocks even at low comonomer contents. It fluctuates only slightly as long as the fractions make up a sufficiently large proportion (at least 10%) of the total polymer. In the case of copolymers of the present invention, the monomer content fluctuates up to a maximum of 10%, preferably a maximum of 5%, particularly preferably a maximum of 1.5%, between the fractions having a sufficiently large proportion.

Single-site-catalyzed copolymers have a narrow molar mass distribution ex reactor (generally $M_w/M_n \leq 3.5$). Ziegler-Natta-catalyzed copolymers have broader molar mass distributions ex reactor.

Furthermore, single-site-catalyzed copolymers have a low proportion of soluble material. At an ethylene content of 10 mol %, the proportion of ether-soluble material is less than 2% by weight.

In addition, a combination of the abovementioned features leads to the polymers of the present invention (homopolymers and copolymers) being eluted within a narrow temperature range in a TREF (for measurement method, see examples). In the case of the homopolymers and random copolymers of the present invention, from 80 to 100% by weight are eluted within a temperature interval extending from 15° C. below to 15° C. above the temperature at which aximum elution occurs ("peak temperature"). The range preferably extends from 15° C. below to 10° C. above the peak temperature and particularly preferably from 10° C. below to 10° C. above the peak temperature.

The polymers prepared by the process of the present invention are suitable for producing high-strength, hard and rigid shaped odies such as fibers, filaments, injection-molded parts, films, sheets or large hollow bodies (e.g. pipes). The moldings display, in particular, a high toughness, even at below 20° C., combined with high stiffness.

Moldings (e.g. injection-molded articles) made of the block polymers of the present invention are generally produced using the customary injection-molding process known to those skilled in the art and have a novel property combination of stiffness, toughness and transparency and additionally display little stress whitening.

The E modulus, as a measure of the stiffness of the copolymers of the present invention, measured in a tensile test in accordance with ISO 527, is generally in the range from 500 to 6,000 MPa, preferably from 800 to 2,000 MPa and very particularly preferably from 900 to 1,400 MPa.

The Charpy impact toughness, as a measure of the toughness of the copolymers of the present invention, measured in accordance with ISO 179-2/1 eU, is >200 kJ/m² at 23° C. and is >20 kJ/m² at −20° C. Preferably, no fracture of the test specimen is recorded at 23° C.

The haze, as complementary value for transparency (% transparency−% haze=100%), determined in accordance with ASTM D 1003, is preferably less than 40%, particularly preferably less than 30%, for the copolymers of the present invention.

The injection-molded articles produced according to the invention may further comprise the customary thermoplastic additives in the customary amounts. Possible additives are antistatics, lubricants such as fatty acid amides, for example erucamide, stabilizers, flame retardants, neutralizing agents such as calcium stearate, colorants such as pigments or liquid dyes, carbon black and also inorganic fillers such as talc, chalk, aluminum oxide, aluminum sulfate, barium sulfate, calcium magnesium carbonate, silicon dioxide, titanium dioxide, glass fibers and organic fillers such as polyesters, polystyrene, polyamide and halogenated organic polymers.

Further preferred additives are nucleating agents such as talc, alkali metal, alkaline earth metal or aluminum salts of alkylcarboxylic, arylcarboxylic, arylalkylcarboxylic or alkylarylcarboxylic acids, certain polymers such as polyvinylcyclohexane or polycyclopentane, and also polyhydroxy compounds such as sorbitol derivatives. Preference is given to talc, aluminum salts, alkali metal salts and alkaline earth metal salts of cyclic arylalkylcarboxylic acids, and also sorbitol derivatives. Particular preference is given to sorbitol derivatives.

The homopolymers and copolymers of the present invention are suitable for producing hard and stiff moldings, fibers, filaments, injection-molded parts, films, sheets or large hollow bodies (e.g. pipes) having a high ultimate tensile strength.

The block copolymers of the present invention are well suited to producing moldings by means of injection molding and extrusion. They are particularly useful for producing injection-molded articles for various applications, as described below by way of example.

The block copolymers of the present invention are suitable for applications in the audio/video/computer sector, for example SACD/DVD/CD/minidisk/CD-ROM packaging, cassette outers, boxes for disks and tapes, chip cards, protective sheathing for chip cards;

in the medical sector, for example Petri dishes, cuvettes, blood analysis tubes, pipettes, disposable pipette tips, drug packaging, in particular bottles, vials, tubes, blisters or lids, syringe cylinders and syringe plungers;

for dairy and food packaging, in particular for refrigerated and frozen products, for example yoghurt tubs, dessert tubs, milk and dairy product packaging such as cheese packaging, delicatessen tubs, single-portion containers, TV dinner containers, tubes, bottles such as ketchup bottles, bottle caps, containers for refrigerated and frozen goods, e.g. ice cream containers;

in the household articles sector, in particular for use in refrigerator and freezer applications, for example drinking cups, cutlery, bowls, containers for food, in particular for refrigerated and frozen goods, e.g. cheese boxes or sausage boxes, microwave applications, catering, blow-molded containers, bottles, tubes, waste containers, filter housings, coathangers, insulated flasks, baby's bottles, tops for baby's bottles, pacifier parts, cartridges, clips;

in the office articles sector, for example in-trays and out-trays, sorting boxes, magazine boxes, wastepaper baskets, upright filing boxes, files, spines of files, drawing utensils, cartridges, ink cartridges, office equipment such as hole punches or staplers, writing instruments such as ballpoint pen outers or marker pens;

in the cosmetics packaging sector, for example containers for creams, lotions and toothpaste, e.g. tubes or dispensing bottles, ointment containers, caps, bottles, tubes, outers, pots, boxes such as wet-wipe boxes, roll-on deodorants (ball and housing), closures, caps, lids of all types;

in the laundry detergent packaging sector, for example sales packaging for laundry detergents, e.g. boxes, bottles or tubes, measuring cups, dispensing balls;

in the bathroom sector, for example toothbrush holders, cups, brush bodies, wet shaver bodies, trays and shelves in the bathroom, bathroom furniture, mirror cabinets, toilet seats and toilet lids, soap dispensers;

in the electrical goods sector, for example coffee machine housings, viewing windows for coffee machines or electric kettles, egg cooker covers, internal parts for refrigerators and freezers, e.g. lining, crispers or baskets, bathroom scales, irons, lampshades, housings for electrical appliances, e.g. computer and monitor housings, tool casings;

in the storage and transport container sector, for example screw containers, tool containers, blister packaging, boxes, baskets, bottles, tubes, cartridges, cases, pallets, viewing windows, transport containers, jewelry and gift packaging, wall-mounted holders;

in the toy sector, for example toys or toy components and also packaging for them, e.g. packaging for playing cards, toy storage containers;

in the laboratory sector, for example measuring cups, measuring cylinders, laboratory flasks, for example for aggressive substances, buckets, cases;

in the motor vehicle sector, for example covers for interior lights, substitutes for glass, polycarbonate or polystyrene, impact-resistant interior lining and exterior cladding;

in the furniture sector, preferably for outdoor furniture, for example transparent, colored or uncolored garden furniture;

in the gardening requisites sector, for example flower boxes, flower pots, watering cans, water containers, compost bins, buckets, irrigation systems, components of garden equipment.

The invention is illustrated by the following examples, which do not, however, restrict the scope of the invention.

I SYNTHESIS OF THE METALLOCENES

General procedures: the preparation and handling of the organometallic compounds was carried out with exclusion of air and moisture under argon (Schlenk technique or glovebox). All solvents required were flushed with argon and dried over molecular sieves before use.

The preparation of heteropentalene systems is carried out using a method of Ewen et al., Metalorganic Catalysts for Synthesis and Polymerization, 1999, Springer-Verlag, 150-169.

Example 1

Preparation of 2-chloroisopentyrophenone 29.2 g of magnesium turnings and 80 ml of THF are placed in a reaction vessel. After starting the reaction using 1/60 (2 ml) of the total amount of the 1-isobutyl bromide, the remaining amount of the 136 ml of isobutyl bromide is added dropwise as a mixture with 300 ml of THF over a period of 1 hour under reflux. The dark brown solution is then heated for another 1 hour under reflux. 15 ml of DME are subsequently added. After cooling to room temperature, the Grignard suspension is added a little at a time by means of a syringe to a suspension of 305 mg of copper(I) iodide and 137.6 g of 2-chlorobenzonitrile dissolved in 240 ml of THF. Toward the end of the Grignard addition, the suspension is refluxed for 2 hours. A solution of 327 ml of water is added dropwise to the suspension while stirring vigorously. Subsequently, 218 ml of 37% strength hydrochloric acid are added over a period of 20 minutes. The emulsion is stirred vigorously for 1 hour at 50° C., after which the aqueous phase is separated from the organic phase. The solvent is removed completely and the residue is subsequently admixed with 50 ml of toluene. The toluene is removed on a rotary evaporator, with the remaining water being distilled off azeotropically. This leaves 205.5 g of crude product which is used without further purification for the next step.

1H-NMR (400 MHz, $CDCl_3$): 7.37-7.26 (m, 4H, arom-H), 2.81 (d, 2H, $CH_2$—H), 2.23 (m, 1H, CH—H), 0.97 (d, 6H, isopropyl-$CH_3$).

Example 2

Preparation of 2-isopropyl-7-chloro-1-indanone 134 g of 2-chloropentyrophenone are placed in a reacton vessel at room temperature together with 200.6 g of urotropin and treated dropwise with 173.6 g of acetic anhydride. The resulting mixture is stirred for 4.5 hours at 80° C. After the reaction is complete, 142.3 ml of water and subsequently 360 g of 20% strength NaOH are added at 80° C. and the viscous reaction mixture is brought into solution. After cooling to room temperature, the mixture is extracted twice with a total of 400 ml of dichloromethane and the combined organic phases are washed twice with a total of 200 ml of 10% strength hydrochloric acid and dried over 140 g of sodium sulfate. The organic dichloromethane phase is added dropwise over a period of 2.5 hours to 273 ml of concentrated sulfuric acid which has been heated to 70° C., with the rate of addition being chosen so that the temperature of the sulfuric acid solution does not go below 70° C. during the reaction as a result of dichloromethane distilling off. The sulfuric acid solution is subsequently allowed to cool to room temperature and the cooled solution is introduced while stirring vigorously into 1000 ml of ice water. The sulfuric acid solution is then extracted three times with a total of 700 ml of dichloromethane, and the combined organic phases are washed with 250 ml of saturated sodium hydrogen carbonate solution and dried over 140 g of sodium sulfate. The solvent is removed on a rotary evaporator. The crude product obtained is distilled in an oil pump vacuum via a Vigreux column with column head. This gives 67.34 g (47%) of 2-isopropyl-7-chloro-1-indanone as a yellow liquid.

1H-NMR (400 MHz, CDCl$_3$): 7.39-7.28 (m, 3H, arom-H), 3.14 (dd, 1H, CH$_2$—H), 2.91 (dd, 1H, CH$_2$—H), 2.70 (m, 1H, CH—H), 2.42 (m, 1H, isopropyl-CH), 1.08, 0.84 (each d, each 3H, isopropyl-CH$_3$).

Example 3

Preparation of 2-isopropyl-7-(4'-tert-butylphenyl)-1-indanone 28.0 g of 2-isopropyl-7-chloro-1-indanone, 28.64 g of 4-tert-butylphenylboronic acid, 35.56 g of sodium carbonate, 302 ml of ethylene glycol and 21.6 ml of water are placed in a reaction vessel. The mixture is degassed a number of times by careful application of an oil pump vacuum and subsequent admission of argon, and thus saturated with argon. It is heated to 80° C. and a freshly prepared catalyst solution comprising 60.23 mg of palladium acetate and 1.79 ml of an aqueous TPPTS solution (0.6 molar) in 25 ml of water is then added while stirring vigorously and the reaction mixture is refluxed for 5 hours with further stirring until completely reacted. After cooling to room temperature, 300 ml of water are added. After renewed cooling to room temperature, the ethylene glycol phase is washed 6 times with a total of 900 ml of toluene. The combined toluene phases are washed twice with a total of 250 ml of sodium chloride solution and dried over 150 g of sodium sulfate. Removal of the solvent on a rotary evaporator, drying of the residue and subsequent distillation in an oil pump vacuum gives 40 g (97%) of 2-isopropyl-7-(4'-tert-butylphenyl)-1-indanone as an orange-brown, viscous oil.

1H-NMR (400 MHz, CDCl$_3$): 7.39-7.24 (m, 7H, arom-H), 3.17 (dd, 1H, CH$_2$—H), 2.94 (dd, 1H, CH$_2$—H), 2.63 (m, 1H, CH—H), 2.38 (m, 1H, isopropyl-CH), 1.31 (s, 9H, tert-butyl-H), 1.06, 0.78 (each d, each 3H, isopropyl-CH$_3$).

Example 4

Preparation of 2-isopropyl-4-(4'-tert-butylphenyl)indene 4.83 g of sodium borohydride and 39.1 g of 2-isopropyl-7-(4'-tert-butylphenyl)-1-indanone together with 11.8. ml of toluene are placed in a reaction vessel. At 50° C., 22.5 ml of methanol are slowly added and the reaction mixture is stirred for 6 hours at 50° C. After cooling to room temperature, 50 ml of 2N sulfuric acid are added and the mixture is stirred vigorously for another 30 minutes. The mixture is subsequently transferred to a separating funnel, the phases are separated and the aqueous phase is shaken twice with a total of 60 ml of 2N sulfuric acid. The organic phases are combined and dried over magnesium sulfate. The solvent of the reaction mixture is removed virtually completely and 200 ml of toluene and 0.4 g of p-toluenesulfonic acid are subsequently added to the residue. Water is distilled from the reaction mixture by heating for 1.5 hours on a water separator until reaction is complete. The reaction mixture is subsequently washed once with 100 ml of saturated sodium hydrogen carbonate solution and dried over magnesium sulfate. After separating off the magnesium sulfate, the residue is dried in an oil pump vacuum. This gives 35.7 g of 2-isopropyl-4-(4'-tert-butylphenyl)indene (total yield: 96%).

1H-NMR (400 MHz, CDCl$_3$): 7.11-6.91 (m, 7H, arom-H), 6.48 (s, 1H, olefin-H), 3.17 (s, 2H, CH$_2$—H), 2.55 (m, 1H, isopropyl-CH), 1.15 (s, 9H, tert-butyl-H), 0.96 (d, 6H, isopropyl-CH$_3$).

2-Isopropyl-4-phenylindene (2), 2-isopropyl-4-(2-naphthyl)indene (3) and 2-isopropyl-4-(1-naphthyl)indene (4) are prepared analogously by coupling with the corresponding boronic acids as described in Example 3. The NMR data of these compounds are shown in the table below.

|   | Aromatics range | Olefin-H | Aliphatic H | Isopropyl-CH | Isopropyl-CH$_3$ |
|---|---|---|---|---|---|
| 2 | 7.13-6.95 | 6.53 | 3.19 | 2.61 | 0.97 |
| 3 | 7.45-7.30 | 6.24 | 3.67 | 2.81 | 0.98 |
| 4 | 7.40-7.26 | 6.22 | 3.60 | 2.80 | 0.96 |

Example 5

Preparation of 2-methyl-4-(4'-tert-butylphenyl)-1-dimethylchlorosilylindene 20.0 g (76 mmol) of 2-methyl-4-(4'-tert-butylphenyl)indene together with 160 ml of toluene and 5 ml of DME are placed in a reaction vessel. 28.4 ml (76 mmol) of a butyllithium solution are added dropwise to this solution, and the mixture is stirred for another 1 hour at 80° C. after the addition is complete. The resulting reaction solution is slowly added dropwise to a solution of 27.7 ml (229 mmol) of dimethyldichlorosilane in 260 ml of THF which has been precooled to −40° C. The reaction mixture is allowed to warm to room temperature and is stirred overnight. The solvent is subsequently removed in an oil pump vacuum and the residue is taken up in 100 ml of toluene. The insoluble lithium chloride is separated off via a G4 frit and the solvent is removed from the filtrate in an oil pump vacuum. This gives 24.8 g (98%) of the desired product.

1H-NMR (400 MHz, CDCl$_3$): 7.3-7.0 (m, 7H, arom-H), 6.7 (s, 1H, olefin-H-indene), 3.5 (s, 1H, H-indene), 2.1 (s, 3H, CH$_3$), 1.3 (s, 9H, tert-butyl), 0.3, 0.05 (each s, each 3H, CH$_3$—Si).

Example 6

Preparation of 2-ethyl-4-(4'-tert-butylphenyl)-1-dimethylchlorosilylindene 20.0 g (72.4 mmol) of 2-ethyl-4-(4'-tert-butylphenyl)indene together with 153 ml of toluene and 4.8 ml of DME are placed in a reaction vessel. 27.0 ml (72.4 mmol) of a butyllithium solution are added dropwise to this solution, and the mixture is stirred for another 1 hour at 80° C. after the addition is complete. The resulting reaction solution is slowly added dropwise to a solution of 26.3 ml (217 mmol) of dimethyldichlorosilane in 248 ml of THF which has been precooled to −40° C. The reaction mixture is allowed to warm to room temperature and is stirred overnight. The solvent is subsequently removed in an oil pump vacuum and the residue is taken up in 100 ml of toluene. The insoluble lithium chloride is separated off via a G4 frit and the solvent is removed from the filtrate in an oil pump vacuum. This gives 25.5 g (95%) of the desired product.

1H-NMR (400 MHz, $CDCl_3$): 7.3-7.0 (m, 7H, arom-H), 6.7 (s, 1H, olefin-H-indene), 3.6 (s, 1H, H-indene), 2.6, 2.4 (each m, 1H, $CH_2$), 1.3 (S, 9H, tert-butyl), 1.1 (t, 3H, $CH_3$), 0.3, 0.0 (each s, each 3H, $CH_3$—Si).

Example 7

Preparation of 2-methyl-(4-thiapentalene)-1-dimethylchlorosilane 20.0 g (148 mmol) of 2-methyl-(2-hydrocyclopenta[2,1-b]thiophene) together with 260 ml of toluene and 8 ml of DME are placed in a reaction vessel. 55.3 ml (148 mmol) of a butyllithium solution are added dropwise to this solution, and the mixture is stirred for another 1 hour at 80° C. after addition is complete. The resulting reaction solution is slowly added dropwise to a solution of 53.9 ml (446 mmol) of dimethyldichlorosilane in 460 ml of THF which has been precooled to −40° C. The reaction mixture is allowed to warm to room temperature and is stirred overnight. The solvent is subsequently removed in an oil pump vacuum and the residue is taken up in 100 ml of toluene. The insoluble lithium chloride is separated off via a G4 frit and the solvent is removed from the filtrate in an oil pump vacuum. This gives 29.1 g (86%) of the desired product.

1H-NMR (400 MHz, $CD_2Cl_2$): 7.3-6.8 (m, 2H), 6.7-6.4 (m, 1H), 4.0-3.4 (m, 2H), 2.6 (m, 3H, $CH_3$), 0.3-0.05 (each s, each 3H, $CH_3$—Si).

Example 8

Preparation of 2-methyl-4-(1-naphthyl)-1-dimethylchlorosilylindene 18.5 g (72 mmol) of 2-methyl-4-(1-naphthyl)indene together with 150 ml of toluene and 4.8 ml of DME are placed in a reaction vessel. 26.9 ml (72 mmol) of a butyllithium solution are added dropwise to this solution, and the mixture is stirred for another 1 hour at 80° C. after addition is complete. The resulting reaction solution is slowly added dropwise to a solution of 26.2 ml (216 mmol) of dimethyldichlorosilane in 250 ml of THF which has been precooled to −40° C. The reaction mixture is allowed to warm to room temperature and is stirred overnight. The solvent is subsequently removed in an oil pump vacuum and the residue is taken up in 100 ml of toluene. The insoluble lithium chloride is separated off via a G4 frit and the solvent is removed from the filtrate in an oil pump vacuum. This gives 23.4 g (93%) of the desired products.

1H-NMR (400 MHz, $CDCl_3$): 7.45-7.32 (m, 7H, arom-H), 6.26 (s, 1H, olefin-H-indene), 3.69 (s, 1H, H-indene), 2.15 (s, 3H, $CH_3$), 0.46, 0.18 (each s, each 3H, $CH_3$—Si).

Other indenyldimethylchlorosilane and heteropentalenedimethylchlorosilane systems can be synthesized using methods analogous to the above-described examples.

Example 9

Preparation of dimethylsilanediyl(2-methyl-4-(4'-tert-butylphenyl)-1-indene)(2-isopropyl-4-(4'-tert-butylphenyl)-1-indene)

16.8 g (57.7 mmol) of 2-isopropyl-7-(4'-tert-butylphenyl)-1-indene together with 131 ml of toluene and 5.0 ml of THF are placed in a reaction vessel, and 21.5 ml of butyllithium solution (2.68 M in toluene) are added all at once at room temperature. After the addition is complete, the mixture is heated to 80° C. and stirred at this temperature for 1 hour. This reaction solution is subsequently allowed to cool to room temperature and is then added dropwise to a solution of 20.5 g (57.7 mmol) of 2-methyl-7-(4'-tert-butylphenyl)-1-indenyldimethylchlorosilane in 246 ml of toluene over a period of 1 hour. The mixture is subsequently stirred overnight at room temperature. 60 ml of water are added and the phases which form are separated. The organic phase is washed with 100 ml of water and the combined aqueous phases are extracted twice with a total of 100 ml of toluene. The combined organic phases are then dried over magnesium sulfate. After separating off the magnesium sulfate, the solvent is removed and the residue is dried in an oil pump vacuum. The desired dimethylsilanediyl(2-methyl-4-(4'-tert-butylphenyl)-1-indene)(2-isopropyl-4-(4'-tert-butylphenyl)-1-indene) is isolated in a yield of 31.6 g (90%) (purity: 90%).

1H-NMR (400 MHz, $CDCl_3$): 7.5-7.1 (m, 14H, arom-H), 6.71, 6.62 (each s, each 1H, olefin-H-indene), 3.31, 3.35 (each s, each 2H, $CH_2$—H), 2.65 (m, 1H, CH-isopropyl), 2.41 (s, 3H, $CH_3$—H), 1.35, 1.33 (each s, each 9H, tert-butyl), 1.15 (d, 6H, isopropyl-$CH_3$), 0.0, 0.2 (each d, each 3H, Si—$CH_3$).

Example 10

Preparation of dimethylsilanediyl(2-ethyl-4-(4'-tert-butylphenyl)-1-indene)(2-isopropyl-4-(4'-tert-butylphenyl)-1-indene)

9.4 g (32.5 mmol) of 2-isopropyl-7-(4'-tert-butylphenyl)-1-indene together with 74 ml of toluene and 3 ml of THF are placed in a reaction vessel, and 12.1 ml of butyllithium solution (2.68 M in toluene) are added all at once at room temperature. After the addition is complete, the mixture is heated to 80° C. and stirred at this temperature for 1 hour. This reaction solution is subsequently allowed to cool to room temperature and is added dropwise to a solution of 12.0 g (32.5 mmol) of 2-ethyl-7-(4'-tert-butylphenyl)-1-indenyldimethyichlorosilane in 138 ml of toluene over a period of 1 hour. The mixture is subsequently stirred overnight at room temperature. 50 ml of water are added and the phases which form are separated. The organic phase is washed with 100 ml of water and the combined aqueous phases are extracted twice with a total of 100 ml of toluene. The combined organic phases are then dried over magnesium sulfate. After separating off the magnesium sulfate, the solvent is removed and the residue is dried in an oil pump vacuum. The desired dimethylsilanediyl(2-ethyl-4-(4'-tert-butylphenyl)-1-indene)(2-isopropyl-4-(4'-tert-butylphenyl)-1-indene) is isolated in a yield of 19.3 g (95%) (purity: 90%).

1H-NMR (400 MHz, CDCl$_3$): 7.48-7.12 (m, 14H, arom-H), 6.91, 6.72 (each s, each 1H, olefin-H-indene), 3.51, 3.47 (each s, each 2H, CH$_2$—H), 2.81 (m, 2H, CH$_2$—H), 2.65 (m, 1H, CH-isopropyl), 1.41, 1.37 (each s, each 9H, tert-butyl), 1.28 (d, 6H, isopropyl-CH$_3$), 0.98 (t, 3H, CH$_3$—H), 0.1, 0.3 (each d, each 3H, Si—CH$_3$).

Example 11

Preparation of dimethylsilanediyl(2-methyl-4-phenyl)-1-indene)(2-isopropyl-4-(4'-tert-butylphenyl)-1-indene)

16.8 g (57.7 mmol) of 2-isopropyl-7-(4'-tert-butylphenyl)-1-indene together with 131.2 ml of toluene and 5 ml of THF are placed in a reaction. vessel, and 21.5 ml of butyllithium solution (2.68 M in toluene) are added all at once at room temperature. After the addition is complete, the mixture is heated to 80° C. and stirred at this temperature for 1 hour. This reaction solution is subsequently allowed to cool to room temperature and is added dropwise to a solution of 17.2 g (57.7 mmol) of 2-methyl-4-phenyl-1-indenyldimethylchlorosilane in 150 ml of toluene over a period of 1 hour. The mixture is subsequently stirred overnight at room temperature. 50 ml of water are added and the phases which form are separated. The organic phase is washed with 100 ml of water and the combined aqueous phases are extracted twice with a total of 100 ml of toluene. The combined organic phases are then dried over magnesium sulfate. After separating off the magnesium sulfate, the solvent is removed and the residue is dried in an oil pump vacuum. The desired dimethylsilanediyl (2-methyl-4-phenyl-1-indene)(2-isopropyl-4-(4'-tert-butylphenyl)-1-indene) is isolated in a yield of 24.9 g (80%) (purity: 80%).

1H-NMR (400 MHz, CDCl$_3$): 7.35-7.10 (m, 14H, arom-H), 6.89, 6.69 (each s, each 1H, olefin-H-indene), 3.45, 3.39 (each s, each 2H, CH$_2$—H), 2.55 (m, 1H, CH-isopropyl), 2.39 (s, 3H, CH$_3$—H), 1.40 (s, 9H, tert-butyl), 1.3 (d, 6H, isopropyl-CH$_3$), 0.05, 0.25 (each d, each 3H, Si—CH$_3$).

Example 12

Preparation of dimethylsilanediyl(2-methylthiapentalene)(2-isopropyl-4-(4'-tert-butylphenyl)indene)

8.4 g (28.9 mmol) of 2-isopropyl-4-(4'-tert-butylphenyl) indene together with 80 ml of toluene and 3.0 ml of THF are placed in a reaction vessel and admixed with 10.7 ml (33.9 mmol) of butyllithium solution. After the addition is complete, the reaction solution is heated to 80° C. and stirred at this temperature for 1 hour. This solution is subsequently allowed to cool to room temperature and added drQpwise at room temperature to a solution of 6.6 g (28.9 mmol) of 2-methyl-1-thiapentalenyldimethylchlorosilane in 140 ml of toluene over a period of 1 hour. The resulting reaction mixture is stirred overnight at room temperature. The reaction solution is then poured into 100 ml of water and the organic phase is separated off. The aqueous phase is extracted once with 50 ml of toluene and the combined organic phases are dried over magnesium sulfate. The solvent is taken off in an oil pump vacuum to give 10.2 g (75%) of the desired ligand system.

1H-NMR (400 MHz, CDCl$_3$): 7.6-6.8 (m, 10H, arom-H), 6.5 (m, 1H), 6.6, 6.4 (each d, each 1H, H-indene), 3.7-3.6 (dd, 2H), 3.3-3.0 (m, 2H), 2.55 (m, 1H, CH-isopropyl), 2.4 (m, 3H, CH$_3$), 1.40 (s, 9H, tert-butyl), 1.25 (d, 6H, isopropyl-CH$_3$), −0.1, −0.3 (each d, each 3H, CH$_3$—Si).

Example 13

Preparation of dimethylsilanediyl(2-isopropyl-4-(4'-tert-butylphenyl)indene)(2-methyl-4,5-benzoindene)

17.0 g (58.4 mmol) of 2-isopropyl-7-(4'-tert-butylphenyl)-1-indene together with 135 ml of toluene and 5 ml of THF are placed in a reaction vessel, and 21.8 ml of butyllithium solution (2.68 M in toluene) are added all at once at room temperature. After the addition is complete, the mixture is heated to 80° C. and stirred at this temperature for 1 hour. This reaction solution is subsequently allowed to cool to room temperature and is added dropwise to a solution of 15.9 g (58.4 mmol) of 2-methyl-4,5-benzoindenyldimethylchlorosilane in 150 ml of toluene over a period of 1 hour. The mixture is subsequently stirred overnight at room temperature. 70 ml of water are added and the phases which form are separated. The organic phase is washed with 100 ml of water and the combined aqueous phases are extracted twice with a total of 100 ml of toluene. The combined organic phases are then dried over magnesium sulfate. After separating off the magnesium sulfate, the solvent is removed and the residue is dried in an oil pump vacuum. The desired dimethylsilanediyl (2-isopropyl-4-(4'-tert-butylphenyl)indene)(2-methyl-4,5-benzoindene) is isolated in a yield of 24.5 g (80%) (purity: 80%).

1H-NMR (400 MHz, CDCl$_3$): 7.6-7.1 (m, 12H, arom-H), 6.7, 6.5 (each d, each 1H, H-indene), 3.2, 3.05 (each s, each 2H, CH$_2$—H), 2.55 (m, 1H, CH-isopropyl), 2.4 (s, 3H, CH$_3$), 1.4 (s, 9H, tert-butyl), 1.2 (d, 6H, isopropyl-CH$_3$), 0.1, −0.15 (each d, each 3H, Si—CH$_3$).

Example 14

Preparation of dimethylsilanediyl(2-isopropyl-4-(1-naphthyl)indene)(2-methyl-4-(4'-tert-butylphenyl)indene)

16.6 g (58.4 mmol) of 2-isopropyl-4-(1-naphthyl)-1-indene together with 135 ml of toluene and 5 ml of THF are placed in a reaction vessel, and 21.8 ml of butyllithium solution (2.68 M in toluene) are added all at once at room temperature. After the addition is complete, the mixture is heated to 80° C. and stirred at this temperature for 1 hour. This reaction solution is subsequently allowed to cool to room temperature and is added dropwise to a solution of 20.7 g (58.4 mmol) of 2-methyl-7-(4'-tert-butylphenyl)-1-indenyldimethylchlorosilane in 240 ml of toluene over a period of 1 hour. The mixture is subsequently stirred overnight at room temperature. 60 ml of water are added and the phases which form are separated. The organic phase is washed with 100 ml of water and the combined aqueous phases are extracted twice with a total of 100 ml of toluene. The combined organic phases are then dried over magnesium sulfate. After separating off the magnesium sulfate, the solvent is removed and the residue is dried in an oil pump vacuum. The desired dimethylsilanediyl(2-isopropyl-4-(1-naphthyl)indene)(2-methyl-4-(4'-tert-butylphenyl)indene) is isolated in a yield of 31.6 g (90%) (purity: 80%).

1H-NMR (400 MHz, CDCl$_3$): 7.4-7.05 (m, 17H, arom-H), 6.8, 6.6 (each d, each 1H, H-indene), 3.2, 3.1 (each s, each 2H, CH$_2$—H), 2.45 (m, 1H, CH-isopropyl), 2.35 (s, 3H, CH$_3$), 1.4 (s, 9H, tert-butyl), 1.25 (d, 6H, isopropyl-CH$_3$), 0.15, −0.25 (each d, each 3H, Si—CH$_3$).

Example 15

Preparation of dimethylsilanediyl(2-isopropyl-4-phenyl-1-indene) (2-methyl-4-(4'-tert-butylphenyl)-1-indene)

13.6 g (58 mmol) of 2-isopropyl-4-phenyl-1-indene together with 135 ml of toluene and 5 ml of THF are placed in a reaction vessel, and 21.6 ml of butyllithium solution (2.68 M in toluene) are added all at once at room temperature. After the addition is complete, the mixture is heated to 80° C. and stirred at this temperature for 1 hour. This reaction solution is subsequently allowed to cool to room temperature and is added dropwise to a solution of 19.2 g (58 mmol) of 2-methyl-4-(4'-tert-butylphenyl)-1-indenyldimethylchlorosilane in 150 ml of toluene over a period of 1 hour. The mixture is subsequently stirred overnight at room temperature. 70 ml of water are added and the phases which form are separated. The organic phase is washed with 90 ml of water and the combined aqueous phases are extracted twice with a total of 100 ml of toluene. The combined organic phases are then dried over magnesium sulfate. After separating off the magnesium sulfate, the solvent is removed and the residue is dried in an oil pump vacuum. The desired dimethylsilanediyl(2-isopropyl-4-phenyl-1-indene)(2-methyl-4-(4'-tert-butylphenyl-1-indene) is isolated in a yield of 25.9 g (85%).

1H-NMR (400 MHz, CDCl$_3$): 7.45-7.10 (m, 14H, arom-H), 6.91, 6.71 (each s, each 1H, olefin-H-indene), 3.45, 3.40 (each s, each 2H, CH$_2$—H), 2.46 (m, 1H, CH-isopropyl), 2.45 (, 3H, CH$_3$—H), 1.40 (s, 9H, tert-butyl), 1.15 (d, 6H, isopropyl-CH$_3$), 0.00, −0.20 (each d, each 3H, Si—CH$_3$).

Example 16

Preparation of dimethylsilanediyl(2-isopropyl-4-phenyl-1-indene) (2-ethyl-4-(4'-tert-butylphenyl)-1-indene)

13.6 g (58 mmol) of 2-isopropyl-4-phenyl-1-indene together with 135 ml of toluene and 5 ml of THF are placed in a reaction vessel, and 21.6 ml of butyllithium solution (2.68 M in toluene) are added all at once at room temperature. After the addition is complete, the mixture is heated to 80° C. and stirred at this temperature for 1 hour. This reaction solution is subsequently allowed to cool to room temperature and is added dropwise to a solution of 20.0 g (58 mmol) of 2-ethyl-4-(4'-tert-butylphenyl)-1-indenyldimethylchlorosilane in 150 ml of toluene over a period of 1 hour. The mixture is subsequently stirred overnight at room temperature. 70 ml of water are added and the phases which form are separated. The organic phase is washed with 90 ml of water and the combined aqueous phases are extracted twice with a total of 100 ml of toluene. The combined organic phases are then dried over magnesium sulfate. After separating off the magnesium sulfate, the solvent is removed and the residue is dried in an oil pump vacuum. The desired dimethylsilanediyl(2-isopropyl-4-phenyl-1-indene)(2-ethyl-4-(4'-tert-butylphenyl)-1-indene) is isolated in a yield of 22.0 g (70%).

1H-NMR (400 MHz, CDCl$_3$): 7.48-7.13 (m, 14H, arom-H), 6.91, 6.72 (each s, each 1H, olefin-H-indene), 3.52, 3.47 (each s, each 2H, CH$_2$—H), 2.81 (m, 2H, CH$_2$—H), 2.65 (m, 1H, CH-isopropyl), 1.37 (each s, each 9H, tert-butyl), 1.28 (d, 6H, isopropyl-CH$_3$), 0.96 (t, 3H, CH$_3$—H), 0.1, −0.3 (each d, each 3H, Si—CH$_3$).

Example 17

Preparation of dimethylsilanediyl(2-methyl-4-(1-naphthyl)indene) (2-isopropyl-4-(4'-tert-butylphenyl)indene)

16.8 g (57.7 mmol) of 2-isopropyl-4-(4'-tert-butylphenyl) indene together with 140 ml of toluene and 5 ml of THF are placed in a reaction vessel, and 21.5 ml of butyllithium solution (2.68 M in toluene) are added all at once at room temperature. After the addition is complete, the mixture is heated to 80° C. and stirred at this temperature for 1 hour. This reaction solution is subsequently allowed to cool to room temperature and is added dropwise to a solution of 20.1 g (57.7 mmol) of 2-methyl-4-(1-naphthyl)-1-indenyldimethylchlorosilane in 240 ml of toluene over a period of 1 hour. The mixture is subsequently stirred overnight at room temperature. 60 ml of water are added and the phases which form are separated. The organic phase is washed with 800 ml of water and the combined aqueous phases are extracted twice with a total of 80 ml of toluene. The combined organic phases are then dried over magnesium sulfate. After separating off the magnesium sulfate, the solvent is removed and the residue is dried in an oil pump vacuum. The desired dimethylsilanediyl (2-methyl-4-(1-naphthyl)indene)(2-isopropyl-4-(4'-tert-butylphenyl)indene) is isolated in a yield of 22.6 g (65%).

1H-NMR (400 MHz, CDCl$_3$): 7.6-7.1 (m, 16H, arom-H), 6.7, 6.5 (each d, each 1H, H-indene), 3.2, 3.1 (each s, each 2H, CH$_2$—H), 2.45 (m, 1H, CH-isopropyl), 2.35 (s, 3H, CH$_3$), 1.35 (s, 9H, tert-butyl), 1.25 (d, 6H, isopropyl-CH$_3$), 0.10, −0.20 (each d, each 3H, Si—CH$_3$).

Example 18

Preparation of dimethylsilanediyl(2-methyl-4-(4'-tert-butylphenyl) indenyl)(2-isopropyl-4-(4'-tert-butylphenyl)indenyl) zirconium dichloride 36.6 g of dimethylsilanediyl(2-methyl-4-(4'-tert-butylphenyl)-1-indene)(2-isopropyl-4-(4'-tert-butylphenyl)-1-indene) together with 366 ml of diethyl ether are placed in a reaction vessel and admixed at room temperature with 44.9 ml of butyllithium solution (2.68 M in toluene). After the addition is complete, the mixture is stirred overnight at this temperature. It is subsequently cooled to 0° C. and 14.0 g of zirconium tetrachloride are added a little at a time. The mixture is allowed to warm to room temperature and is stirred for another 2 hours at this temperature. The orange precipitate formed is then separated off via a G3 frit and washed twice with 50 ml each time of THF and once with 70 ml of pentane. The residue is subsequently dried in an oil pump vacuum. The complex is obtained in a yield of 23.5 g (50%).

1H-NMR (400 MHz, CDCl$_3$): pseudo-rac: 7.7-6.9 (m, 14 H, arom-H), 3.26 (m, 1H, CH-isopropyl), 2.23 (s, 3H, CH$_3$), 1.31 (s, 18H, tert-butyl), 1.33, 1.32 (each s, each 3H, Si—CH$_3$), 1.08, 1.03 (each d, each 3H, isopropyl-CH$_3$). Pseudo-meso: 7.7-6.7 (m, 14 H, arom-H), 3.18 (m, 1H, CH-isopropyl), 2.44 (s, 3H, CH$_3$), 1.34 (s, 18H, tert-butyl), 1.47, 1.25 (each s, each 3H, Si—CH$_3$), 1.20 (m, 6H, isopropyl-CH$_3$).

Example 19

Preparation of dimethylsilanediyl(2-ethyl-4-(4'-tert-butylphenyl)indenyl)(2-isopropyl-4-(4'-tert-butylphenyl)indenyl)zirconium dichloride 18.1 g (29 mmol) of dimethylsilanediyl(2-ethyl-4-(4'-tert-butylphenyl)-1-indene)(2-isopropyl-4-(4'-tert-butylphenyl)-1-indene) together with 181 ml of diethyl ether are placed in a reaction vessel and admixed at room temperature with 21.7 ml of butyllithium solution (2.68 M in toluene). After the addition is complete, the mixture is stirred overnight at this temperature. It is subsequently cooled to 0° C. and 6.8 g (29 mmol) of zirconium tetrachloride are added a little at a time. The mixture. is allowed to warm to room temperature and is stirred for another 2 hours at this temperature. The orange precipitate formed is then separated off via a G3 frit and washed twice with 50 ml each time of THF and once with 70 ml of pentane. The residue is subsequently dried in an oil pump vacuum. The complex is obtained in a yield of 13.6 g (60%).

1H-NMR (400 MHz, CDCl$_3$): pseudo-rac: 7.6-6.8 (m, 14 H, arom-H), 3.15 (m, 1H, CH-isopropyl), 2.7, 2.5 (each m, each 1H, CH$_2$), 1.38, 1.35 (each s, each 3H, Si—CH$_3$), 1.32 ([lacuna], 18H, tert-butyl), 1.10, 1.05 (each d, each 3H, CH$_3$-isopropyl), 0.85 (t, 3H, CH$_3$). Pseudo-meso: 7.7-6.7 (m, 14 H, arom-H), 3.25 (m, 1H, CH-isopropyl), 2.6, 2.4 (each m, each 1H, CH$_2$), 1.50, 1.21 (each s, each 3H, Si—CH$_3$), 1.33 ([lacuna], 18H, tert-butyl), 1.20 (m, 6H, CH$_3$-isopropyl), 1.05 (t, 3H, CH$_3$).

Example 20

Preparation of dimethylsilanediyl(2-methyl-4-(4'-tert-butylphenyl)indenyl)(2-isopropyl-4-phenylindenyl)zirconium dichloride 16.0 g (29 mmol) of dimethylsilanediyl(2-isopropyl-4-phenyl-1-indene)(2-methyl-4-(4'-tert-butylphenyl)-1-indene) together with 190 ml of diethyl ether are placed in a reaction vessel and admixed at room temperature with 21.7 ml of butyllithium solution (2.68 M in toluene). After the addition is complete, the mixture is stirred overnight at this temperature. It is subsequently cooled to 0° C. and 6.8 g (29 mmol) of zirconium tetrachloride are added a little at a time. The mixture is allowed to warm to room temperature and is stirred for another 4 hours at this temperature. The orange precipitate formed is then separated off via a G4 frit and washed twice with 60 ml each time of THF and once with 100 ml of pentane. The residue is subsequently dried in an oil pump vacuum. The complex is obtained in a yield of 11.4. g (55%).

1H-NMR (400 MHz, CDCl$_3$): pseudo-rac: 7.8-7.0 (m, 15 H, arom-H), 3.24 (m, 1H, CH-isopropyl), 2.22 (s, 3H, CH$_3$), 1.31 (s, 9H, tert-butyl), 1.32, 1.30 (each s, each 3H, Si—CH$_3$), 1.10, 1.05 (each d, each 3H, isopropyl-CH$_3$). Pseudo-meso: 7.8-6.9 (m, 15 H, arom-H), 3.21 (m, 1H, CH-isopropyl), 2.41 (s, 3H, CH$_3$), 1.33 (s, 18H, tert-butyl), 1.49, 1.27 (each s, each 3H, Si—CH$_3$), 1.17 (m, 6H, isopropyl-CH$_3$).

Example 21

Preparation of dimethylsilanediyl(2-methyl-4-phenyl-1-indenyl)(2-isopropyl-4-(4'-tert-butylphenyl)-1-indenyl)zirconium dichloride 17.1 g (31 mmol) of dimethylsilanediyl(2-methyl-4-phenyl-1-indene)(2-isopropyl-4-(4'-tert-butylphenyl)-1-indene) together with 200 ml of diethyl ether are placed in a reaction vessel and admixed at room temperature with 23.2 ml of butyllithium solution (2.68 M in toluene). After the addition is complete, the mixture is stirred overnight at this temperature. It is subsequently cooled to 0° C. and 7.3 g (31 mmol) of zirconium tetrachloride are added a little at a time. The mixture is allowed to warm to room temperature and is stirred for another 3 hours at this temperature. The orange precipitate formed is then separated off via a G4 frit and washed twice with 60 ml each time of THF and once with 100 ml of pentane. The residue is subsequently dried in an oil pump vacuum. The complex is obtained in a yield of 10.4 g (50%).

1H-NMR (400 MHz, CDCl$_3$): pseudo-rac: 7.8-7.1 (m, 15 H, arom-H), 3.24 (m, 1H, CH-isopropyl), 2.23 (s, 3H, CH$_3$), 1.31 (s, 9H, tert-butyl), 1.32, 1.30 (each s, each 3H, Si—CH$_3$), 1.11, 1.06 (each d, each 3H, isopropyl-CH$_3$). Pseudo-meso: 7.8-7.0 (m, 15 H, arom-H), 3.22 (m, 1H, CH-isopropyl), 2.41 (s, 3H, CH$_3$), 1.33 (s, 18H, tert-butyl), 1.49, 1.27 (each s, each 3H, Si—CH$_3$), 1.18 (m, 6H, isopropyl-CH$_3$).

Example 22

Preparation of dimethylsilanediyl(2-ethyl-4-(4'-tert-butylphenyl)indenyl)(2-isopropyl-4-phenylindenyl)zirconium dichloride 10.8 g (20 mmol) of dimethylsilanediyl(2-isopropyl-4-phenyl-1-indene)(2-ethyl-4-(4'-tert-butylphenyl)-1-indene) together with 120 ml of toluene and 5 ml of THF are placed in a reaction vessel and admixed at room temperature with 15.0 ml of butyllithium solution (2.68 M in toluene). After the addition is complete, the mixture is stirred at this temperature for 4 hours. It is subsequently cooled to 0° C. and 4.7 g (20 mmol) of zirconium tetrachloride are added a little at a time. The mixture is allowed to warm to room temperature and is stirred for another 5 hours at this temperature. The orange precipitate formed is then separated off via a G3 frit and washed twice with 50 ml each time of THF. The residue is subsequently dried in an oil pump vacuum. The complex is obtained in a yield of 6.3 g (45%).

1H-NMR (400 MHz, CDCl$_3$): pseudo-rac: 7.5-6.8 (m, 15 H, arom-H), 3.19 (m, 1H, CH-isopropyl), 2.5, 2.3 (each m, each 1H, CH$_2$), 1.33, 1.31 (each s, each 3H, Si—CH$_3$), 1.32 (s, 9H, tert-butyl), 1.10, 1.07 (each d, each 3H, CH$_3$-isopropyl), 0.87 (t, 3H, CH$_3$). Pseudo-meso: 7.7-6.7 (m, 14 H, arom-H), 3.27 (m, 1H, CH-isopropyl), 2.6, 2.3 (each m, each 1H, CH$_2$), 1.35 (each s, each 3H, Si—CH$_3$), 1.34 (s, 18H, tert-butyl), 1.25 (m, 6H, CH$_3$-isopropyl), 0.93 (t, 3H, CH$_3$).

Example 23

Preparation of dimethylsilanediyl(2-methylthiapentalenyl)(2-isopropyl-4-(4'-tert-butylphenyl)indenyl)zirconium dichloride 16.5 g (35 mmol) of dimethylsilanediyl(2-methylthiapentalene)(2-isopropyl-4-(4'-tert-butylphenyl)indene) together with 150 ml of diethyl ether are placed in a reaction vessel and admixed at room temperature with 26.2 ml of butyllithium solution (2.68 M in toluene). After the addition is complete, the mixture is stirred overnight at this temperature. It is subsequently cooled to 0° C. and 8.2 g (35 mmol) of zirconium tetrachloride are added a little at a time. The mixture is allowed to warm to room temperature and is stirred for another 5 hours at this temperature. The precipitate formed is then separated off via a G3 frit and washed twice with 60 ml each time of THF and once with 80 ml of pentane. The residue is subsequently dried in an oil pump vacuum. The complex is obtained in a yield of 8.8 g (40%).

1H-NMR (400 MHz, $CDCl_3$): pseudo-rac: 7.7-6.8 (m, 10 H, arom-H), 6.6-6.5 (m, 1H, H-thiapentalene), 3.23 (m, 1H, CH-isopropyl), 2.1 (m, 3H, $CH_3$), 1.4 (s, 9H, tert-butyl), 1.5, 1.3 (each s, each 3H, Si—$CH_3$), 1.10, 1.05 (each d, each 3H, isopropyl-$CH_3$). Pseudo-meso: 7.7-6.8 (m, 10 H, arom-H), 6.4-6.2 (m, 1H, H-thiapentalene), 3.35 (m, 1H, CH-isopropyl), 2.3 (m, 3H, $CH_3$), 1.35 (s, 9H, tert-butyl), 1.2 (s, 6H, Si—$CH_3$), 1.15 (m, 6H, isopropyl-$CH_3$).

Example 24

Preparation of dimethylsilanediyl(2-isopropyl-4-(4'-tert-butylphenyl)indenyl)-(2-methyl-4,5-benzoindenyl)zirconium dichloride 7.9 g (15 mmol) of dimethylsilanediyl(2-methyl-4,5-benzoindene)(2-isopropyl-4-(4'-tert-butylphenyl)-1-indene) together with 90 ml of diethyl ether are placed in a reaction vessel and admixed at room temperature with 11.2 ml of butyllithium solution (2.68 M in toluene). After the addition is complete, the mixture is stirred overnight at this temperature. It is subsequently cooled to 0° C. and 3.53 g (15 mmol) of zirconium tetrachloride are added a little at a time. The mixture is allowed to warm to room temperature and is stirred for another 4 hours at this temperature. The precipitate formed is then separated off via a G4 frit and washed twice with 60 ml each time of THF. The complex is recrystallized from a toluene/pentane mixture. The residue is subsequently dried in an oil pump vacuum. The complex is obtained in a yield of 3.1 g (30%).

1H-NMR (400 MHz, $CDCl_3$): pseudo-rac: 8.0-6.9 (m, 12 H, arom-H), 3.15 (m, 1H, CH-isopropyl), 2.25 (s, 3H, $CH_3$), 1.35 (s, 9H, tert-butyl), 1.36, 1.35 (each s, each 3H, Si—$CH_3$), 1.09, 1.07 (each d, each 3H, isopropyl-$CH_3$). Pseudo-meso: 8.0-6.9 (m, 12 H, arom-H), 3.39 (m, 1H, CH-isopropyl), 2.25 (s, 3H, $CH_3$, coincides with that of the rac form), 1.35 (s, 9H, tert-butyl, coincides with that of the rac form), 1.37 (s, 6H, Si—$CH_3$), 1.24 (m, 6H, isopropyl-$CH_3$).

Example 25

Preparation of dimethylsilanediyl(2-methyl-4-(4'-tert-butylphenyl)indenyl)(2-isopropyl-4-(1-naphthyl)indenyl)zirconium dichloride 11.4 g (19 mmol) of dimethylsilanediyl(2-isopropyl-4-(1-naphthyl)-1-indene)(2-methyl-4-(4'-tert-butylphenyl)-1-indene) together with 150 ml of toluene and 15 ml of THF are placed in a reaction vessel and admixed at room temperature with 14.3 ml of butyllithium solution (2.68 M in toluene). After the addition is complete, the mixture is stirred overnight at this temperature. It is subsequently cooled to 0° C. and 4.4 g (19 mmol) of zirconium tetrachloride are added a little at a time. The mixture is allowed to warm to room temperature and is stirred for another 2 hours at this temperature. The precipitate formed is then separated off via a G4 frit and washed twice with 50 ml each time of THF. The residue is subsequently dried in an oil pump vacuum. The complex is obtained in a yield of 5.9 g (41%).

1H-NMR (400 MHz, $CDCl_3$): pseudo-rac: 7.8-6.95 (m, 17 H, arom-H), 3.21 (m, 1H, CH-isopropyl), 2.25 (s, 3H, $CH_3$), 1.33, 1.31 (each s, each 3H, Si—$CH_3$), 1.32 (s, 9H, tert-butyl), 1.09, 1.07 (each d, each 3H, $CH_3$-isopropyl). Pseudo-meso: 7.9-7.07 (m, 17 H, arom-H), 3.37 (m, 1H, CH-isopropyl), 2.50 (s, 3H, $CH_3$), 1.35 (each s, each 3H, Si—$CH_3$), 1.32 (s, 18H, tert-butyl, coincides with that of the rac form), 1.25 (m, 6H, $CH_3$-isopropyl).

Example 26

Preparation of dimethylsilanediyl(2-isopropyl-4-(4'-tert-butylphenyl)indenyl)-(2-methyl-4-(1-naphthyl)indenyl)zirconium dichloride 15.0 g (25 mmol) of dimethylsilanediyl(2-methyl-4-(1-naphthyl)-1-indene)(2-isopropyl-4-(4'-tert-butylphenyl)-1-indene) together with 170 ml of toluene and 20 ml of THF are placed in a reaction vessel and admixed at room temperature with 17.9 ml of butyllithium solution (2.68 M in toluene). After the addition is complete, the mixture is stirred overnight at this temperature. It is subsequently cooled to 0° C. and 5.9 g (25 mmol) of zirconium tetrachloride are added a little at a time. The mixture is allowed to warm to room temperature and is stirred for another 2 hours at this temperature. The precipitate formed is then separated off via a G4 frit and washed twice with 50 ml each time of THF and with 70 ml of pentane. The residue is subsequently dried in an oil pump vacuum. The complex is obtained in a yield of 6.8 g (41%).

1H-NMR (400 MHz, $CDCl_3$): pseudo-rac: 7.8-6.95 (m, 17 H, arom-H), 3.22 (m, 1H, CH-isopropyl), 2.23 (s, 3H, $CH_3$), 1.33, 1.31 (each s, each 3H, Si—$CH_3$), 1.32 (s, 9H, tert-butyl), 1.08, 1.06 (each d, each 3H, $CH_3$-isopropyl). Pseudo-meso: 7.9-7.05 (m, 17 H, arom-H), 3.35 (m, 1H, CH-isopropyl), 2.48 (s, 3H, CH$_3$), 1.35 (each s, each 3H, Si—CH$_3$), 1.32 (s, 18H, tert-butyl, coincides with that of the rac form), 1.22 (m, 6H, CH$_3$-isopropyl).

II CATALYST PREPARATION AND POLYMERIZATION

Abbreviations:

| | |
|---|---|
| PP = | Polypropylene |
| MC = | Metallocene |
| Cat = | supported catalyst system |
| h = | hour |
| Standard dm$^3$ = | Standard liters |
| rpm = | Revolutions per minute |
| VN = | Viscosity number in cm$^3$/g |
| M$_w$ = | Weight average molar mass in g/mol |
| M$_w$/M$_n$ = | Molar mass distribution, determined by gel permeation chromatography |
| BD = | Bulk density in g/dm$^3$ and |
| M.p. = | Melting point in ° C., determined in accordance with ISO 3146 by differential scanning calorimetry (DSC) at a heating and cooling rate of 10° C./min. |
| TT = | Triad tacticity in percent determined by $^{13}$C-NMR spectroscopy |
| RI = | Reverse insertions in %; determined in accordance with ISO 3146 by $^{13}$C-NMR spectroscopy |

NMR Measurements:

From 110 to 135 mg of the samples were weighed into 10 mm NMR tubes and dissolved at elevated temperature in a solvent mixture of dideuterotetrachloroethane (C$_2$D$_2$Cl$_4$) and hexachlorobutadiene (C$_4$Cl$_6$). The NMR spectra of the solutions were recorded at 353 K (instrument setting) on a Bruker DMX 500 NMR spectrometer in accordance with SOP 1030-038 (GLP), using a spinning sample, under the following conditions:

| | |
|---|---|
| Radio frequency (BF1) | 125.7577 MHz |
| Pulse angle (P1) | 30° |
| Spectral width (SW) | 250 ppm |
| Acquisition time (AQ) | 2.08 sec |
| Delay time (D1) | 1.92 sec |
| Number of data points (TD) | 131 072 |
| Number of pulses (NS) | >8000 |

The $^{13}$C-NMR measurement was carried out with broadband decoupling of the protons.

Before Fourier transformation of the FIDs, an exponential multiplication by a line broadening factor LB=1 Hz was carried out. After the Fourier transformation, a linear baseline correction in the region of the relevant signals in the range from about 10 to 60 ppm was carried out. The chemical shifts were calibrated relative to the signal of dideuterotetrachloroethane at 73.81 ppm.

In the integration of the propylene homopolymers, the following conventions were employed: integration range for signals of the mm triads: 22.55 ppm to 20.85 ppm; mr triads: 20.85 ppm to 20.0 ppm; rr triads: 20.0 to 19.15 ppm; 2,1 insertion: 17.35 ppm to 16.75 ppm; 1,3 insertion: sum of the integrals from 37 ppm to 36.5 ppm and from 30.7 to 30.2 ppm. It is known that a single 2,1 insertion produces two signals in the integration range, while regioregular insertions produce only one signal. To convert the ratios of the mr triads to the 2,1 insertions into molar ratios, the values for the 2,1 insertions have to be divided by two. In the case of the convention employed, on the other hand, the ratios of the signals of the 2,1 insertions to the 1,3 insertions are identical to the molar ratios.

It is also known that both 2,1 and 1,3 insertions each produce a further signal located in the integration range of the mr triads. Since the signals in the integration range of the mr triads can sometimes not be detected with separation on the baseline, the molar ratios cannot be obtained directly. To calculate the molar ratios of the mm triads to the mr triads, the signal intensities of the reverse insertions firstly have to be subtracted from the intensities observed for the mr triads.

In the evaluation of the spectra of propylene-ethylene copolymers, the carbon atoms are numbered as follows:
—C$^1$H$_2$—CH(CH$_3$)—;
—CH$_2$—CH(CH$_3$)—C$^5$H$_2$—C$^7$H$_2$—CH$_2$—CH(CH$_3$)—;
—CH$_2$—CH(CH$_3$)—C$^5$H$_2$—C$^6$H$_2$—C$^9$H$_2$—CH$_2$—CH$_2$—CH(CH$_3$)—;
—CH$_2$—CH(CH$_3$)—C$^5$H$_2$—C$^6$H$_2$—C$^9$H$_2$—(C$^{10}$H$_2$—CH$_2$)$_n$—CH$_2$—CH(CH$_3$)—;
—CH$_2$—CH(CH$_3$)—C$^{12}$H$_2$—C$^{13}$H$_2$—CH$_2$—CH$_2$—CH(CH$_3$)—;
—CH$_2$—CH(CH$_3$)—C$^{16}$H$_2$—C$^{15}$H$_2$—CH(CH$_3$)—C$^{15}$H$_2$—C$^{16}$H$_2$—CH(CH$_3$)—.

Both ends of the sequences shown are in each case adjoined by —CH$_2$—CH(CH$_3$)—. The assignment of the signals to the numbered carbon atoms is well known to those skilled in the art.

Coupled GPC-IR Measurements

GPC was carried out on a Waters 150C HT-GPC apparatus. The results were calibrated using polystyrene. An interface model 300 from Lab Connections, Marlborough, Mass. (USA) was employed for coupling. Here, the eluant is atomized in a vacuum chamber by means of an ultrasound signal and removed by heating and vacuum. The polymer which remains is continuously collected on a rotating germanium disk. This disk. is subsequently scanned by means of an optic module in a Nicolet Impact 40OD FTIR spectrometer.

Conditions: GPC: eluant: trichlorobenzene, flow rate: 1.1 ml/min, injection volume: 150 µl, temperature: 150° C. Interface: nozzle temperature: 110° C., flow rate: 1.1 ml/min, Ge disk heating: 165° C., transfer line: 145° C., rotation rate: 10°/min. FTIR: continuous recording of spectra at 10°/min using Omnic standard software: 270 spectra in 30 minutes (one spectrum every 8 seconds), each based on 16 scans, detector: DTGS.

Evaluation was carried out using a method established by Dekmezian, as has been published, for example, in the applications leaflet No. 16 from LabConnections. Here, the ratio of the C—H stretching vibrations to the ethylene content is calculated. A person skilled in the art will know that the constants in this ratio depend on the measurement conditions employed. They were determined by means of blending of linear polyethylene (PE) and isotactic polypropylene. Analogous experimental conditions were selected for this purpose (same GPC, same coupling, same recording of spectra), but the GPC columns were not employed; rather, spraying was carried out directly from the injector onto the Ge plate so that no demixing occurs. This calibration results in the following formula:

mol % of $PE=39.7*ln[A(2922$ cm$^{-1})+A(2850$ cm$^{-1})/A(2953$ cm$^{-1})]-9.2$ In this formula, A is the peak height of the signal at the wave number indicated in brackets.

Determination of Ether-Soluble Material

About 5 g of polymer are extracted with 280 ml of peroxide-free diethyl ether (stabilized with 0.1% of Irganox 1010, 1 g of stabilizer/1 of ether) under reflux in a 1 l round-bottom flask for 4 hours. The undisclosed material is separated off and the solution is evaporated to about 50 ml. The dissolved material is precipitated by addition of a large excess [lacuna], aggregated by stirring using a magnetic stirrer and isolated by filtration on a glass filter crucible Dab 1 (diameter: 30 mm).

Example 27

Preparation of the supported catalyst system: 70 mg (0.091 mmol) of rac-dimethylsilanediyl(2-methyl-4-(para-tert-butylphenyl)indenyl)(2-isopropyl-4-(para-tert-butylphenyl)indenyl)zirconium dichloride (Example 18) were dissolved at room temperature in 4.3 cm$^3$ (20 mmol of Al) of 30% strength methylaluminoxane solution in toluene (Albemarle Corporation, Baton Rouge, La., USA). The solution was diluted with 3.7 cm$^3$ of toluene and stirred at 25° C. for 1 hour while being protected from light. This solution was added a little at a time while stirring to 4 g of Soothed 2 (grade MS 948, W. R. Grace, Davison Chemical Division, Baltimore, Md., USA, pore volume: 1.6 ml/g, claimed at 600° C.) and, after the addition was complete, the mixture was stirred for another 10 minutes. The ratio of the volume of solution to the total pore volume of the support material was 1.25. The mixture was subsequently dried for 4 hours at 40° C. and 10$^{-3}$ mbar. This gave 5.5 g of a free-flowing powder which, according to elemental analysis, contained 0.13% by weight of Zr and 9.5% by weight of Al.

Polymerization:

A dry 16 dm$^3$ reactor which had been flushed firstly with nitrogen and subsequently with propene was charged with 10 dm$^3$ of liquid propene. 8 cm$^3$ of 20% strength triethylaluminum solution in Verso (Witco) were added as scavenger and the mixture was stirred for 15 minutes at 30° C. A suspension of 2 g of the supported etallocene catalyst in 20 cm$^3$ of Exxsol was subsequently introduced into the reactor, the reaction mixture was heated to the polymerization temperature of 70° C. and the polymerization system was maintained at 70° C. for 1 hour. The polymerization was stopped by venting and the polymer obtained was dried under reduced pressure. This gave 2.7 kg of polypropylene powder.

The catalyst activity was 123 kg of PP/(g of MC×h) or 1.4 kg of PP/(g of Cat×h)

The isotactic polypropylene prepared had the following properties: M.p.=157° C.; $M_w$=4.5×10$^5$ g/mol, $M_w/M_n$=2.6, VN=430 cm$^3$/g, BD=460 g/dm$^3$, TT=>99%, RI=0.32%.

Examples 28 to 34

Preparation of the supported catalyst system: The procedure of Example 27 was repeated using further metallocenes.

The results are summarized in the following table.

| Ex. no. | Metallocene | | Weight of metallocene used [mg] | Zr content [% by weight] | Al content [% by weight] |
|---|---|---|---|---|---|
| 28 | Dimethylsilanediyl(2-ethyl-4-(4'-tert-butylphenyl)indenyl)-(2-isopropyl-4-(4'-tert-butylphenyl)indenyl)zirconium dichloride | E19 | 71.3 | 0.16 | 9.5 |
| 29 | Dimethylsilanediyl(2-methyl-4-(4'-tert-butylphenyl)indenyl)-(2-isopropyl-4-phenylindenyl)-zirconium dichloride | E20 | 64.8 | 0.15 | 9.5 |
| 30 | Dimethylsilanediyl(2-methyl-4-phenyl)-1-indenyl)(2-isopropyl-4-(4'-tert-butylphenyl)-1-indenyl)zirconium dichloride | E21 | 64.8 | 0.14 | 9.5 |
| 31 | Dimethylsilanediyl(2-ethyl-4-(4'-tert-butylphenyl)indenyl)-(2-isopropyl-4-phenylindenyl)-zirconium dichloride | E22 | 66.1 | 0.14 | 9.5 |
| 32 | Dimethylsilanediyl(2-isopropyl-4-(4'-tert-butylphenyl)-indenyl)(2-methyl-4,5-benzoindenyl)zirconium dichloride | E24 | 62.5 | 0.13 | 9.5 |
| 33 | Dimethylsilanediyl(2-methyl-4-(4'-tert-butylphenyl)indenyl)-(2-isopropyl-4-(1-naphthyl)-indenyl)zirconium dichloride | E25 | 69.4 | 0.16 | 9.5 |
| 34 | Preparation of dimethylsilanediyl(2-isopropyl-4-(4'-tert-butylphenyl)-indenyl)(2-methyl-4-(1-naphthyl)indenyl)zirconium dichloride | E26 | 69.3 | 0.13 | 9.5 |

Polymerization:

The procedure of Example 27 was repeated using further catalysts. The results are listed in the following table.

| Ex. no. | Metallocene no. | Yield of PP [kg] | Activity [kg of PP/g of Cat * h] | M.p. | $M_w$ | $M_w/M_n$ | BD |
|---|---|---|---|---|---|---|---|
| 28 | E19 | 2.1 | 1.1 | 157 | 515000 | 3.1 | 450 |
| 29 | E20 | 2.3 | 1.2 | 156 | 433000 | 2.8 | 430 |

-continued

| Ex. no. | Metallocene no. | Yield of PP [kg] | Activity [kg of PP/g of Cat * h] | M.p. | $M_w$ | $M_w/M_n$ | BD |
|---|---|---|---|---|---|---|---|
| 30 | E21 | 2.6 | 1.3 | 156 | 365000 | 2.7 | 420 |
| 31 | E22 | 2.4 | 1.2 | 156 | 467000 | 2.6 | 440 |
| 32 | E24 | 2.1 | 1.1 | 156 | 376000 | 2.3 | 450 |
| 33 | E25 | 2.6 | 1.3 | 157 | 569000 | 2.5 | 455 |
| 34 | E26 | 2.4 | 1.2 | 158 | 589000 | 2.3 | 435 |

Example 35

The polymerization was carried out using a method analogous to Example 27, but additionally using 5 standard dm³ of hydrogen in the polymerization. This gave 3.2 kg of polypropylene powder.

The catalyst activity was 146 kg of PP/(g of MC×h) or 1.6 kg of PP/(g of Cat×h).

The isotactic polypropylene prepared had the following properties: M.p.=159° C.; $M_w$=2.5×10⁵ g/mol, $M_w/M_n$=3.0, VN=270 cm³/g, BD=450 g/dm³, TT>99%, RI=0.3%.

Examples 36 to 40a (Comparative Examples) 1

Preparation of the Supported Catalyst System:

The preparation was carried out using a method analogous to Examples 27 to 34. The results are summarized in the following table.

| Ex. no. | Metallocene | Weight used [mg] | Zr content [% by weight] | Al content [% by weight] |
|---|---|---|---|---|
| 36 | Dimethylsilanediylbis-(2-methyl-4-(4'-tert-butylphenyl)indenyl)-zirconium dichloride | 67.4 | 0.16 | 9.5 |
| 37 | Dimethylsilanediyl-(2-methyl-4-phenyl)-indenyl)(2-isopropyl-4-phenyl)indenyl)zirconium dichloride | 59.7 | 0.14 | 9.5 |
| 38 | Dimethylsilanediyl-(2-methyl-4-(1-naphthyl)indenyl(2-isopropyl-4-phenyl)indenyl)-zirconium dichloride | 64.1 | 0.16 | 9.5 |
| 39 | Dimethylsilanediyl-(2-methyl-4-phenyl-indenyl)(2-methyl-4,5-benzoindenyl)zirconium dichloride | 54.9 | 0.16 | 9.5 |
| 40 | Dimethylsilanediyl-(2-methyl-4-(1-naphthyl)indenyl)(2-methyl-4-phenylindenyl)zirconium dichloride | 64.1 | 0.16 | 9.5 |
| 40a | Dimethylsilanediylbis-(2-methyl-4-(1-naphthyl)indenyl)zirconium dichloride | 1.7 | 0.15 | 9.4 |

Polymerization:

The polymerizations were carried out using a method analogous to Examples 27 to 34. The results are summarized in the following table.

| Ex. no. | Metallocene | Weight of PP obtained [kg] | Activity [kg/(g × h)] | M.p. | $M_w$ | $M_w/M_n$ | BD |
|---|---|---|---|---|---|---|---|
| 36 | Dimethylsilanediylbis-(2-methyl-4-(4'-tert-butylphenyl)indenyl)-zirconium dichloride | 3.2 | 1.6 | 154 | 900000 | 2.6 | 460 |
| 37 | Dimethylsilanediyl-(2-methyl-4-phenylindenyl)(2-isopropyl-4-phenylindenyl)-zirconium dichloride | 1.1 | 0.6 | 152 | 322000 | 3.1 | 450 |
| 38 | Dimethylsilanediyl-(2-methyl-4-(1-naphthyl)indenyl)(2-isopropyl-4-phenylindenyl)zirconium dichloride | 1.3 | 0.7 | 153 | 390000 | 2.9 | 435 |
| 39 | Dimethylsilanediyl-(2-methyl-4-phenylindenyl)(2-methyl-4,5-benzoindenyl)zirconium dichloride | 1.6 | 0.8 | 149 | 340000 | 2.5 | 450 |
| 40 | Dimethylsilanediyl-(2-methyl-4-(1-naphthyl)indenyl)(2-methyl-4-phenylindenyl)-zirconium dichloride | 1.7 | 0.9 | 150 | 360000 | 2.6 | 460 |

TABLE

| Ex. no. | Metallocene from Example no.: | Monomers | Weight of PP obtained [kg] | Activity [kg of PP/(g of Cat * h)] | M.p. | $M_w$ | $M_w/M_n$ | C2 content [% by weight] |
|---|---|---|---|---|---|---|---|---|
| 41 | E18 | 12 l of propene/150 g of ethene | 2.42 | 3.5 | 141 | 522000 | 2.3 | 6.1 |
| 42 | E19 | 12 l of propene/150 g of ethene | 2.5 | 3.6 | 142 | 688000 | 3.1 | 6.5 |
| 43 | E20 | 12 l of propene/150 g of ethene | 2.6 | 3.7 | 140 | 578000 | 2.8 | 5.8 |
| 44 | E21 | 12 l of propene/150 g of ethene | 2.4 | 3.4 | 141 | 555000 | 2.7 | 5.9 |
| 45 | E22 | 12 l of propene/150 g of ethene | 2.1 | 3.0 | 142 | 589000 | 2.6 | 6 |
| 46 | E24 | 12 l of propene/150 g of ethene | 2.6 | 3.7 | 141 | 569000 | 2.3 | 5.8 |
| 47 | E25 | 12 l of propene/150 g of ethene | 2.7 | 3.9 | 142 | 621000 | 2.5 | 6.3 |
| 48 | E26 | 12 l of propene/150 g of ethene | 2.6 | 3.7 | 142 | 643000 | 2.3 | 6.7 |
| 49 | E18 | 12 l of propene/450 g of ethene | 2.52 | 3.6 | 115 | 592000 | 2.5 | 18.1 |
| 50 | E19 | 12 l of propene/450 g of ethene | 2.62 | 3.7 | 116 | 699000 | 3.1 | 18.5 |
| 51 | E20 | 12 l of propene/450 g of ethene | 2.74 | 3.9 | 114 | 589000 | 2.5 | 16 |
| 52 | E21 | 12 l of propene/450 g of ethene | 2.54 | 3.6 | 113 | 576000 | 2.8 | 17.1 |
| 53 | E22 | 12 l of propene/450 g of ethene | 2.5 | 3.6 | 115 | 599000 | 2.5 | 16.5 |
| 54 | E24 | 12 l of propene/450 g of ethene | 2.65 | 3.8 | 113 | 589000 | 2.4 | 18.2 |
| 55 | E25 | 12 l of propene/450 g of ethene | 2.8 | 4.0 | 117 | 643000 | 2.7 | 19.9 |
| 56 | E26 | 12 l of propene/450 g of ethene | 2.76 | 3.9 | 118 | 651000 | 2.6 | 19.8 |

Example 41 to 56

A dry 24 dm³ reactor was flushed with propylene and charged with 12 dm³ of liquid propylene, 150 g of ethylene (Examples 41 to 48) or 450 g of ethylene (Examples 49 to 56) and 22 cm³ of a solution of triisobutylaluminum in hexane (8 mmol of Al, 2 cm³ of triisobutylaluminum diluted with 20 cm³ of hexane), and the reactor stirrer was set to 250 rpm. 0.7 g of the supported catalyst prepared in Examples 27 to 34 was suspended in 25 cm³ of a dearomatized petroleum fraction having a boiling range of 100-120_C and the suspension was introduced into the reactor. The reactor was heated to the polymerization temperature of 70_C (7.5_C/min) and maintained at this polymerization temperature for 1 hour by cooling the reactor jacket. The polymerization was stopped by quickly venting the excess monomers. The polymer was dried under reduced pressure. Polymer yield, catalyst activity and product data are shown in the following table.

Examples 57 to 68 (Comparative Examples)

The procedure of Examples 41 to 56 was repeated. The results are shown in the following table. When using the catalyst system which is not according to the present invention, the molar mass $M_w$ drops significantly below the value obtained in the homopolymerizations in Examples 36 to 40.

TABLE

| Ex. no. | Metallocene from Example no.: | Monomers | Weight of PP obtained [kg] | Activity [kg of PP/(g of Cat * h)] | M.p. | $M_w$ | $M_w/M_n$ | C2 content [% by weight] |
|---|---|---|---|---|---|---|---|---|
| 57 | 36 | 12 l of propene/150 g of ethene | 2.24 | 3.2 | 140 | 815000 | 2.2 | 3 |
| 58 | 36 | 12 l of propene/450 g of ethene | 2.38 | 3.4 | 109 | 586000 | 2.4 | 10.6 |
| 59 | 40a | 12 l of propene/150 g of ethene | 1.19 | 1.7 | 133 | 509000 | 2.3 | 3 |
| 60 | 40a | 12 l of propene/450 g of ethene | 1.26 | 1.8 | 106 | 464000 | 2.8 | 10.5 |
| 61 | 37 | 12 l of propene/450 g of ethene | 1.8 | 2.6 | 108 | 149000 | 2.4 | 11 |
| 62 | 37 | 12 l of propene/150 g of ethene | 1.6 | 2.3 | 138 | 210000 | 2.2 | 3.5 |
| 63 | 38 | 12 l of propene/450 g of ethene | 1.9 | 2.7 | 107 | 256000 | 2.4 | 10.9 |
| 64 | 38 | 12 l of propene/150 g of ethene | 1.6 | 2.3 | 141 | 305000 | 2.2 | 3.1 |
| 65 | 39 | 12 l of propene/450 g of ethene | 1.7 | 2.4 | 108 | 215000 | 2.4 | 10.2 |
| 66 | 39 | 12 l of propene/150 g of ethene | 1.5 | 2.1 | 140 | 280000 | 2.2 | 3.2 |
| 67 | 40 | 12 l of propene/450 g of ethene | 1.8 | 2.6 | 109 | 223000 | 2.4 | 11.1 |
| 68 | 40 | 12 l of propene/150 g of ethene | 1.6 | 2.3 | 138 | 289000 | 2.2 | 3.1 |

Examples 69 to 76

Preparation of the Supported Catalyst System 0.5 ml of N,N-dimethylaniline is added at room temperature to a suspension of 2 g of Soothed 2 (see Example 27) in 30 ml of toluene. The mixture is cooled to 0° C. and 40 ml of a clear, light-yellow solution (0.1M based on Al) of bis(pentafluorophenylboroxy)methylalane in 95 ml of toluene are added dropwise from a dropping funnel. The mixture is allowed to warm to room temperature and is stirred for another 3 hours. The suspension is subsequently filtered and the solid is washed with pentane. The residue is then dried to constant weight in an oil pump vacuum. This gives 3.96 g of a pale purple support material.

0.06 mmol of metallocene in 35 ml of toluene are stirred with 0.08 ml of TMA (2M in toluene, 0.16 mmol) for 10 minutes. Subsequently, 1.6 g of the supported cocatalyst prepared above are added at room temperature. The catalyst solution is stirred for 1 hour and the solvent is then taken off in an oil pump vacuum. This gives a pink, free-flowing powder.

| Ex. no. | Metallocene from Example no: | Weight of metallocene used [mg] |
|---|---|---|
| 69 | E18 | 46.1 |
| 70 | E19 | 47.0 |
| 71 | E20 | 42.7 |
| 72 | E21 | 42.7 |
| 73 | E22 | 43.6 |
| 74 | E24 | 41.2 |
| 75 | E25 | 45.8 |
| 76 | E26 | 45.7 |

Polymerization:

The polymerization was carried out using a method analogous to Example 27. The results are shown in the following table.

TABLE

| Ex. no. | Metallocene from Example no.: | Calculated weight of catalyst used | Weight of PP obtained [kg] | Activity [kg of PP/(g of Cat * h)] | M.p. | $M_w$ | $M_w/M_n$ | BD |
|---|---|---|---|---|---|---|---|---|
| 69 | E18 | 0.80 | 2.5 | 3.1 | 158 | 450000 | 2.3 | 410 |
| 70 | E19 | 0.80 | 2.1 | 2.6 | 158 | 515000 | 2.7 | 450 |
| 71 | E20 | 0.80 | 2 | 2.5 | 158 | 433000 | 2.8 | 430 |
| 72 | E21 | 0.80 | 2.2 | 2.8 | 157 | 365000 | 2.6 | 440 |
| 73 | E22 | 0.80 | 2.4 | 3.0 | 156 | 467000 | 2.4 | 420 |
| 74 | E24 | 0.80 | 2.5 | 3.1 | 157 | 376000 | 2.3 | 430 |
| 75 | E25 | 0.80 | 2.3 | 2.9 | 158 | 569000 | 2.3 | 450 |
| 76 | E26 | 0.80 | 2.2 | 2.8 | 159 | 589000 | 2.5 | 450 |

Example 77

The polymerization was carried out using a method analogous to Example 69, but only 0.4 g of catalyst were used and, in addition, 5 standard dm³ of hydrogen were used in the polymerization. This gave 3.2 kg of polypropylene powder.

The catalyst activity was 8 kg of PP/(g of Cat×h).

The isotactic polypropylene prepared had the following properties: M.p.=160° C.; $M_w$=250000 g/mol, $M_w/M_n$=2.6, BD=420 g/dm³.

Example 78

A dry 24 dm³ reactor was flushed with propylene and placed under a hydrogen pressure of 0.5 bar. The reactor was subsequently charged with 12 dm³ of liquid propylene and 22 cm³ of a solution of triisobutylaluminum in hexane (8 mmol of Al, 2 cm³ of triisobutylaluminum diluted with with 20 cm³ of hexane) and the reactor stirrer was set to 250 rpm. 0.7 g of the supported catalyst prepared in Example 27 was suspended in 25 cm³ of a dearomatized petroleum fraction having a boiling range of 100-120° C. and the suspension was introduced into the reactor. The reactor was heated to the polymerization temperature of 70° C. (7.5° C./min)-and maintained at this polymerization temperature for 1 hour by cooling the reactor jacket.

The reactor was subsequently depressurized to 10 bar and pressurized with 20 bar of ethylene. The mixture was polymerized further for 2 hours at 60° C. and the polymerization was then stopped by quickly venting the excess monomers. This gave a block copolymer having the following properties:

Homopolymer matrix (iPP from fractionation): M.p.=159° C.; $M_w$=2.6×10⁵ g/mol; $M_w/M_n$=2.5, VN=240 cm³/g. Rubber (ethylene-propylene copolymer): $T_g$=−47° C.; 56% by weight of $C_2$; VN=680 cm³/g; $M_w$=6.9×10⁵ g/mol; $M_w/M_n$=3.0.

Example 79 (Comparative Example)

Example 78 was repeated using a supported catalyst prepared as described in Example 36. This gave a block copolymer having the following properties:

Homopolymer matrix (iPP from fractionation): M.p.=155° C.; $M_w$=2.8×10⁵ g/mol; $M_w/M_n$=2.6, VN=230 cm³/g. Rubber (ethylene-propylene copolymer): $T_g$=−49° C.; 44% by weight of $C_2$; VN=374 cm³/g; $M_w$=4.03×10⁵ g/mol; $M_w/M_n$=3.0.

Comparative Example 80

Example 78 was repeated using a supported catalyst containing dimethylsilanediylbis(2-methyl-4-(1-naphthyl)indenyl)zirconium dichloride as metallocene. This gave a block copolymer having the following properties:

Homopolymer matrix (iPP from fractionation): M.p.=154° C.; $M_w$=1.99×10⁵ g/mol; $M_w/M_n$=2.6; VN=168 cm³/g. Rubber (ethylene-propylene copolymer): $T_g$=−50° C.; 46% by weight of $C_2$; VN=280 cm$^3$/g; $M_w$=3.54×10$^5$ g/mol; $M_w/M_n$=2.7.

Example 81

Example 78 was repeated, except that the reactor was charged with only 10 dm$^3$ of liquid propylene and the catalyst was introduced as a paste. For this purpose, 20 g of the catalyst prepared in Example 27 were stirred into 100 ml of an oil (white oil Ondina G 33, Deutsche Shell AG)/Vaseline (Deutsche Shell AG) mixture (4/1). An aliquot of the resulting paste corresponding to 0.7 g of catalyst powder was introduced into a pressure lock and rinsed into the reactor using 2 dm$^3$ of liquid propylene.

This gave a block copolymer having properties comparable to those in Example 78.

Example 82

Example 78 was repeated, except that the first polymerization stage was carried out at 65° C. in the presence of 60 g of ethylene. This gave a block copolymer having the following properties:

Homopolymer matrix (iPP from fractionation): M.p.=158° C.; $M_w$=2.5×10$^5$ g/mol; $M_w/M_n$=2.5; VN=260 cm$^3$/g. Rubber (ethylene-propylene copolymer): $T_g$=−26° C.; 14% by weight of $C_2$; VN=576 cm$^3$/g; $M_w$=6.02×10$^5$ g/mol; $M_w/M_n$=2.8.

High molecular weight copolymers with olefins higher than ethylene can also be prepared using the metallocenes of the present invention. Some examples are presented below to illustrate the principle:

Example 83

Example 27 was repeated, except that the reactor was depressurized to 18 bar and then pressurized with only 5 bar of ethylene prior to the second polymerization step. This gave a block copolymer which suffered from little stress whitening and had the following properties:

Homopolymer matrix (iPP from fractionation): M.p.=150° C.; $M_w$=3.35×10$^5$ g/mol; $M_w/M_n$=2.7; VN=315 cm$^3$/g. Rubber (ethylene-propylene copolymer): $T_g$=−52° C.; 47% by weight of $C_2$; VN=295 cm$^3$/g; $M_w$=3.43×10$^5$ g/mol; $M_w/M_n$=2.8.

Examples 84 to 86

A dry 24 dm$^3$ reactor was flushed with propylene and charged with 12 dm$^3$ of liquid propylene and 22 cm$^3$ of a solution of triisobutylaluminum in hexane (8 mmol of Al, 2 cm$^3$ of triisobutylaluminum diluted with 20 cm$^3$ of hexane), and the reactor stirrer was set to 250 rpm. After addition of a third of the total 9.62 mol of comonomer intended for the polymerization, 0.7 g of the catalyst prepared in Example 27, suspended in 25 cm$^3$ of a dearomatized petroleum fraction having a boiling range of 100-120° C., was introduced into the reactor. The reactor was heated to the polymerization temperature of 65° C. (7.5° C./min) and maintained at this polymerization temperature for 1 hour by cooling the reactor jacket. During this polymerization time, the remaining two thirds of the comonomer were metered continuously into the reactor. The polymerization was stopped by quickly venting the excess monomers. The polymer was dried under reduced pressure. Polymer yield, metallocene activities and product data are shown in the table below.

Examples 87 to 89 (Comparative Examples)

Examples 84 to 86 were repeated using a catalyst prepared from dimethylsilanediylbis(2-methyl-4-(1-naphthyl)indenyl)zirconium dichloride as metallocene. Polymer yield, metallocene activities and product data are shown in the following table.

| Ex. | Comonomer | Yield [kg of copolymer] | Activity [kg/ (g × h)] | M.p. [° C.] | VN [cm$^3$/g] | Comonomer content [% by weight] |
|---|---|---|---|---|---|---|
| 84 | 1-Butene | 2.40 | 3.43 | 132 | 546 | 4.8 |
| 85 | 4-Methyl-1-pentene | 1.55 | 2.21 | 122 | 536 | 3.5 |
| 86 | 1-Hexene | 2.87 | 4.10 | 108 | 606 | 6.1 |
| 87 | 1-Butene | 1.16 | 1.65 | n.d. | 452 | 2.4 |
| 88 | 4-Methyl-1-pentene | 0.81 | 1.15 | n.d. | 437 | 2.6 |
| 89 | 1-Hexene | 1.44 | 2.06 | n.d. | 490 | 3.0 |

High molecular weight terpolymers can also be prepared using the catalysts of the present invention. Some examples are presented below to illustrate the principle:

Examples 90 to 93

A dry 24 dm$^3$ reactor was charged with 10 l of a dearomatized petroleum fraction having a boiling range of 100-120° C. The gas space was then flushed by pressurizing the reactor five times with 2 bar of propylene and venting it each time. After addition of 2000 g of propylene, 300 g of ethylene and, if required for the particular example, 100 g of a further monomer (see Table 3), 10 cm$^3$ of methylaluminoxane solution in toluene (corresponding to 15 mmol of Al, molar mass determined by cryoscopy=1200 g/mol) were added. The contents of the reactor were heated to 60° C. 2.1 mg of rac-dimethylsilanediyl(2-methyl-4-(para-tert-butylphenyl)indenyl)(2-isopropyl-4-(para-tert-butylphenyl)indenyl) zirconium dichloride were dissolved in 10 cm$^3$ of the methylaluminoxane solution in toluene (corresponding to 15 mmol of Al) and likewise introduced into the reactor. During the polymerization time of 2 hours, a further 300 g of ethylene were metered in. The polymerization was stopped by quickly venting the excess monomers. The polymer was separated from the petroleum spirit and dried under reduced pressure at 100° C. Polymer yields, metallocene activities and product data are shown in the table below.

Examples 94 to 97 (Comparative Examples)

Examples 90 to 93 were repeated using 2.0 mg of dimethylsilanediylbis(2-methyl-4-(1-naphthyl)indenyl)zirconium dichloride. Polymer yields, metallocene activities and product data are shown in the following table.

| Ex. | Further monomer | Yield [kg of copolymer] | Activity [kg/(g × h)] | VN [cm³/g] | C₂ content [% by weight] | Comonomer content [% by weight] |
|---|---|---|---|---|---|---|
| 90 | — | 2.01 | 479 | 595 | 52.2 | — |
| 91 | 1-Butene | 1.80 | 429 | 426 | 44.7 | 4.5 |
| 92 | 4-Methyl-1-pentene | 1.02 | 243 | 444 | 48.3 | 4.0 |
| 93 | 1-Hexene | 1.78 | 424 | 463 | 46.9 | 4.1 |
| 94 | — | 1.54 | 385 | 405 | 45.0 | — |
| 95 | 1-Butene | 1.22 | 305 | 349 | 40.8 | 3.0 |
| 96 | 4-Methyl-1-pentene | 1.34 | 336 | 328 | 44.0 | 2.3 |
| 97 | 1-Hexene | 1.52 | 380 | 400 | 42.6 | 3.2 |

Examples 98 to 102

High-Impact Copolymers by Gas-Phase polymerization
A: Preparation of the Metallocene Catalyst 3 kg of Sylopol 948 are placed in a process filter whose filter plate points downward, and suspended in 15 l of toluene. 7 l of a 30% strength by weight MAO solution (from Albemarle) are metered in while stirring at such a rate that the internal temperature does not exceed 35° C. After stirring for another 1 hour at a low stirrer speed, the suspension is filtered, firstly under atmospheric pressure and then using 3 bar of nitrogen pressure. In parallel to the treatment of the support material, 2.0 l of 30% strength by weight MAO solution and 92.3 g of rac-dimethylsilyl(2-methyl-4-(para-tert-butylphenyl)-indenyl)(2-isopropyl-4-(para-tert-butyl-phenyl)indenyl)-zirconium dichloride are placed in a reaction vessel, the solution is stirred for 1 hour and allowed to settle for a further 30 minutes. The solution is subsequently added to the pretreated support material with the outlet closed. After addition is complete, the outlet is opened and the filtrate is allowed to drain. When no more runs off, the outlet is closed, the filter cake is stirred for 15 minutes and allowed to rest for 1 hour. A nitrogen pressure of 3 bar is subsequently applied with the outlet open. 15 l of isododecane are added to the remaining solid, the mixture is stirred for 15 minutes and filtered. The washing step is repeated, and the solid is subsequently pressed dry by means of a nitrogen pressure of 3 bar. For use in the polymerization, the total amount of the catalyst is resuspended in 15 l of isododecane.

B: Polymerization

The process was carried out in two stirring autoclaves connected in series, each provided with a free-standing helical stirrer and each having a utilizable capacity of 200 l. Both reactors contained an agitated fixed bed of finely divided propylene polymer.

The propylene was introduced in gaseous form into the first polymerization reactor and polymerized at a mean residence time as shown in Table 1 with the aid of the metallocene catalyst A (see above) at a pressure and temperature as shown in Table 1. The above-described metallocene catalyst was metered in at such a rate that the transfer from the first polymerization reactor to the second polymerization reactor corresponds, on average, to the amounts of polymer shown in Table 1. The metallocene catalyst was introduced together with the fresh propylene added to regulate the pressure. Triethylaluminum (in the form of a 1 molar solution in heptane, in an amount corresponding to Table 1) was likewise metered into the reactor. Polymer powder was taken intermittently from the reactor by briefly venting the reactor via an immersed tube. The propylene polymer formed in the first reactor together with the catalyst and together with unreacted monomers was thus introduced into the second reactor.

There, a mixture of propylene and ethylene was polymerized onto it at a total pressure, a temperature and a mean residence time corresponding to Table 1. The proportion of ethylene was the percentage by volume indicated in Table 1; the ethylene concentration in the reaction gas was determined by gas chromatography. The weight ratio of the propylene polymer formed in the first reactor (PP(I)) to the copolymer formed in the second reactor (EPR(II)) is shown in Table 1. Isopropanol (in the form of a 0.5 molar solution in heptane) was likewise metered into the second reactor. The isopropanol was metered-in in such an amount that the weight ratio of PP(I):EPR(II) shown in Table 1 was maintained.

The analytical experiments on the polymer powders and their constituents are shown in Table 2:

TABLE 1

| | Polymerization conditions | | | | |
|---|---|---|---|---|---|
| | Ex. 98 | Ex. 99 | Ex. 100 | Ex. 101 | Ex. 102 |
| Reactor I | | | | | |
| Pressure [bar] | 28 | 29 | 29 | 26 | 26 |
| Temperature [° C.] | 75 | 75 | 75 | 70 | 70 |
| Triethylaluminum (1 molar in heptane) [ml/h] | 60 | 60 | 60 | 90 | 90 |
| Residence time [h] | 2.25 | 2.25 | 2.25 | 1.5 | 1.5 |
| MFR of powder [dg/min] (ISO 1133) | 11.0 | 9.8 | 9.2 | 10.0 | 9.8 |
| Powder output [kg/h] | 20 | 20 | 20 | 30 | 30 |
| Reactor II | | | | | |
| Pressure [bar] | 15 | 15 | 15 | 15 | 15 |
| Temperature [° C.] | 65 | 65 | 65 | 65 | 65 |
| Ethylene [% by vol.] | 30 | 41 | 49 | 28 | 33 |
| Residence time [h] | 1.7 | 1.7 | 1.7 | 1.0 | 1.2 |
| Powder output [kg/h] | 24.1 | 24.2 | 24.3 | 39.2 | 37.7 |
| MFR of powder [dg/min] (ISO 1133) | 10.7 | 8.7 | 5.5 | 9.5 | 10.4 |
| Weight ratio of PP (I):EPR (II) | 4.9 | 4.8 | 4.7 | 3.3 | 3.9 |

TABLE 2

Analysis of the copolymer powders:

| | Ex. 98 | Ex. 99 | Ex. 100 | Ex. 101 | Ex. 102 |
|---|---|---|---|---|---|
| Homopolymer content [% by wt.] (Prepared in reactor I) | 80 | 79 | 79 | 71 | 76 |
| Copolymer content [% by wt.] (Prepared in reactor II) | 20 | 21 | 21 | 29 | 24 |
| C2 content of copolymer fraction [% by wt.] (IR determination) | 7.5 | 23.3 | 40.0 | 6.5 | 22.5 |
| Viscosity number (ISO 1628) [cm3/g] | | | | | |
| Homopolymer fraction | 175 | 164 | 185 | 160 | 162 |
| Copolymer fraction | 152 | 157 | 191 | 168 | 160 |
| Glass transition temperatures [° C.] (DMA measurement) | −6 | 2/−42 | 2/−56 | −4 | −5 |
| GPC measurements | | | | | |
| Molar mass $M_n$ [g/mol] | 101000 | 95000 | 105900 | 105500 | 100600 |
| Molar mass distribution $M_w/M_n$ | 2.1 | 2.1 | 2.0 | 2.1 | 2.0 |

Determination of analytical data on product fractions: Fractionation of the polymer by means of TREF (as described by L. Wild, "Temperature rising elution fractionation", Advanced Polym. Sci. 98, 1-47 (1990). Fractions were eluted with xylene at 40, 80, 90, 100 and 120° C. and assigned correspondingly to the homopolymer fraction (prepared in reactor I) or the copolymer fraction (prepared in reactor II).

Granulation of the Polymer Powders:

The dried polymer powders were intimately mixed with a standard additive mixture (addition of 0.05% by weight of Irganox 1010, 0.05% by weight of Irgafos 168, 0.1% by weight of calcium stearate and 0.2% by weight of Millad 3988). The resultant powders were extruded on a Werner & Pfleiderer ZSK 30 twin-screw extruder at a melt temperature of 250° C. and subsequently granulated in a granulator. The production of the test specimens required for the applications-related tests and the tests themselves were carried out in accordance with the standards indicated in Table 3.

TABLE 3

Applications-related testing of the granulated polymers

| | Test method | Ex. 98 | Ex. 99 | Ex. 100 | Ex. 101 | Ex. 102 |
|---|---|---|---|---|---|---|
| MFR (230° C./2.16 kg) [dg/min] | ISO 1133 | 12.3 | 8.7 | 6.9 | 11.0 | 12.6 |
| Hexane extract [%] | FDA | 0.9 | 0.4 | 0.2 | 0.6 | 0.5 |
| E modulus [MPa] | ISO 527 | 1156 | 1006 | 1093 | 1120 | 1020 |
| Charpy impact toughness (23° C.) [kJ/m$^2$] | ISO 179-2/1 eU | no fracture | no fracture | no fracture | no fracture | no fracture |
| Charpy impact toughness (0° C.) [kJ/m$^2$] | ISO 179-2/1 eU | 163 | no fracture | no fracture | 160 | no fracture |
| Charpy impact toughness (−20° C.) [kJ/m$^2$] | ISO 179-2/1 eU | 28 | 180 | 130 | 26 | 123 |
| Heat distortion resistance HDT B [° C.] | ISO 75-2 Method B | 81 | 76 | 78 | 80 | 79 |
| Softening temperature Vicat A [° C.] | ISO 306 VST/A50 | 141 | 139 | 140 | 140 | 141 |
| DSC melting point [° C.] | ISO 3146 | 156 | 157 | 157 | 156 | 156 |
| Haze [%] | ASTM D 1003 | 10 | 20 | 17 | 8 | 9 |

Examples 103 to 109:

Homopolymers and Random Copolymers of Propylene and Their Properties

Production of Catalysts

Catalyst Al:

Work is initially carried out under an argon atmosphere in a glove box. 319.3 mg of the complex rac-dimethylsilyl-(2-methyl-4-(para-tert-butylphenyl)indenyl)(2-iso-propyl-4-(para-tert-butylphenyl)indenyl)zirconium dichloride are dissolved in a mixture of 18.4 ml of 30% strength by weight MAO solution (from Albemarle) and 22 ml of toluene. After stirring for 1 hour at room temperature, the solution is clear and is added to 20.16 g of silica gel Sylopol 948 from Grace Davison ($d_{50}$=50 µm; dried for 8 hours at 300° C. in a stream of nitrogen). After all of the solution has been added, the mixture is stirred for another 10 minutes and the paste-like mass is transferred to a Schlenk vessel (N2 flask).

Outside the glove box, the volatile constituents are removed on a vacuum line equipped with an oil pump using an oil bath heated to 40° C., until approximately constant weight is achieved after about 4 hours. The residual content of volatile constituents is determined on a Mettler-Toledo moisture analyzer and is 2.05%.

Comparative Catalyst B:

The catalyst preparation of experiment $ [sic] is repeated using 155.1 mg of the complex rac-dimethylsilylbis-(2-methyl-4-(para-tert-butylphenyl)indenyl)zirconium dichloride, 9.3 ml of 30% strength by weight MAO solution and 10.17 g of silica gel. The residual moisture is 2.3%.

Comparative Catalyst C:

4 kg of silica gel Sylopol 948 from Grace Davison ($d_{50}$=50 µm; dried for 8 hours at 300° C. in a stream of nitrogen) are placed in a process filter, 18 l of heptane are introduced and the contents of the reactor are cooled to an internal temperature of 20° C. 6 l of a 2 molar solution of triisobutylaluminum in heptane are added over a period of about 30 minutes at such a rate that the internal temperature does not exceed 30° C. After the addition of the alkyl, the cryostat is switched off and the mixture is stirred further for about 2 hours at a very low stirrer speed. The suspension is filtered using nitrogen pressure, the filter cake is washed three times with 12 l each time of toluene. The solid is resuspended in 11 l of toluene and 291 g of dimethylcyclohexylammonium tetrakis(pentafluorophenyl)borate are added to the suspension. The mixture is subsequently heated to an internal temperature of 80° C. and stirred at this temperature for 30 minutes. The complex rac-dimethylsilylbis(2-methyl-4-phenyl-indenyl)zirconium dichloride is then added and the mixture is stirred for another 1.5 hours at 80° C. The catalyst is then dried under reduced pressure (about 40 mbar) at an internal temperature of about 80° C.

Homopolymerizations

Experiment 103

A dry 16 $dm^3$ reactor which had been flushed firstly with nitrogen and subsequently with propene was charged with 10 $dm^3$ of liquid propene. 8 $cm^3$ of 20% strength by weight triethylaluminum solution in Verso (Witco) were added as scavenger and the mixture was stirred for 15 minutes at 30° C. A suspension of 1.5 g of the catalyst A1 in 20 $cm^3$ of Exxsol was subsequently introduced into the reactor, the mixture was heated to the polymerization temperature of 65° C. and the polymerization system was held at this temperature for 1 hour. The polymerization was stopped by venting and the polymer obtained was dried under reduced pressure. This gave 2.05 kg of polypropylene powder. $M_w$: 260 00.0 g/mol; $M_w/M_n$: 3.6. $^{13}$C-NMR spectrum: ratio of the signal intensities of mm triads/mr triads/rr triads: 96.0/2.9/1.1. Ratio of mm triads/2,1 insertions: 1230/10. Ratio of 2,1 insertions/1,3 insertions: 3/1.

Comparative Experiment 104

The polymerization of Experiment @ [sic] was repeated using 1.1 g of the comparative catalyst B. This gave 3.09 kg of polypropylene powder. $M_w$: 514 000 g/mol; $M_w/M_n$: 3.3. $^{13}$C-NMR spectrum: ratio of the signal intensitities of mm triads/mr triads/rr triads: 97.6/2.0/0.4. Ratio of mm triads/2,1 insertions: 485/10.

Comparative Example 105

The polymerization of Experiment @ [sic] was repeated using 38.8 $cm^3$ of 20% strength by weight diisobutylaluminum solution in Verso (Witco) as scavenger. 630 mg of the comparative catalyst C were added. Immediately after the catalyst, 63 mg of Atmer were introduced. This gave 2.59 kg of polypropylene powder. $M_w$: 350,000 g/mol; $M_w/M_n$: 3.4. $^{13}$C-NMR spectrum: Ratio of the signal intensities of mm triads/mr triads/rr triads: 98.3/ 1.3/0.4. Ratio of mm triads/2,1 insertions: 1100/10.

Copolymerizations

Experiment 106

A dry 5 $dm^3$ reactor which had been flushed firstly with nitrogen and subsequently with propene was charged with 3 $dm^3$ of liquid propene. Ethylene was subsequently introduced until a pressure increase of 500 Pa had been established at 30° C. 2.3 $cm^3$ of 20% strength by weight triethylaluminum solution in Verso (Witco) were added as scavenger, the mixture was stirred for 15 minutes and subsequently heated to 65° C. A suspension of 250 mg of the catalyst A1 in 6 $cm^3$ of heptane was subsequently introduced into the reactor. Immediately afterwards, 25 mg of Atmer 163 were introduced. The polymerization was stopped after 10 minutes by venting and the polymer obtained was dried under reduced pressure. This gave 5 g of polypropylene copolymer. $M_w$: 307,000 g/mol; $M_w/M_n$: 3.2. $^{13}$C-NMR spectrum: signal intensities: $C^1$: 74.171; $C^5$ and $C^{12}$: 14.780; $C^7$: 6.203; $C^9$ and $C^{10}$: 1.931; $C^6$ and $C^{13}$: 2.289; $C^{15}$ and $C^{16}$: 0.625. This gives an ethylene content of 10.0%. Proportion soluble in diethyl ether: 0.54%. GPC—IR spectroscopy: The spectra were combined so that one spectrum corresponds to each chromatographic minute (120 scans/spectrum).

| Retention time [min] | Molar mass range [g/mol] | Proportion of the fraction [% by wt.] | PE content [mol %] |
|---|---|---|---|
| 16 to 17 | 4.5e6-1.1e6 | 4.4 | 10.8 |
| 17 to 18 | 1.1e6-4.2e5 | 13.3 | 9.8 |
| 18 to 19 | 4.2e5-2e5 | 21.6 | 10.0 |
| 19 to 20 | 2e5-1.1e5 | 23.0 | 11.0 |
| 20 to 21 | 1.1e5-6.5e4 | 17.6 | 11.1 |
| 21 to 22 | 6.5e4-3.8e4 | 11.6 | 11.0 |
| 22 to 23 | 3.8e4-2.2e4 | 5.8 | 12.0 |

The differences between the individual fractions are within measurement accuracy (±1%) and purely random. Division into narrower fractions gives an analogous result.

Experiment 107

A dry 16 $dm^3$ reactor which had been flushed firstly with nitrogen and subsequently with. ethylene was charged with ethylene until a pressure increase of 500 Pa had been established at 30° C. 10 l of liquid propene and 8 $cm^3$ of 20% strength by weight triethylaluminum solution in Verso (Witco) as scavenger were subsequently added, the mixture was stirred for 15 minutes and subsequently heated to 65° C. A suspension of 1.1 g of the catalyst A1 in heptane was subsequently introduced into the reactor. Immediately afterwards, 110 mg of Atmer 163 were introduced. The polymerization was stopped after 10 minutes by venting and the polymer obtained was dried under reduced pressure. This gave 22 g of polypropylene copolymer. $M_w$: 362,000 g/mol; $M_w/M_n$: 3.1. $^{13}$C-NMR spectrum: signal intensities: $C^1$: 91.243; $C^5$ and $C^{12}$: 4.741; $C^7$: 2.222; $C^9$ and $C^{10}$: 0.686; $C^6$ and $C^{13}$: 0.574; $C^{15}$ and $C^{16}$: 0.534. This gives an ethylene content of 3.2%.

Comparative Experiment 108

The polymerization of Experiment 106 was repeated using 250 mg of the comparative catalyst B. This gave 31 g of polypropylene copolymer. $M_w$: 273,000 g/mol; $M_w/M_n$: 3.2. $^{13}$C-NMR spectrum: signal intensities: $C^1$: 76.419; $C^5$ and $C^{12}$: 13.199; $C^7$: 5.600; $C^9$ and $C^{10}$: 1.531; $C^6$ and $C^{13}$: 2.220; $C^{15}$ and $C^{16}$: 1.032. This gives an ethylene content of 9.0%.

Comparative Experiment 109

The polymerization of Experiment 106 was repeated using 11.7 $cm^3$ of 20% strength by weight triisobutylaluminum solution in Verso (witco) as scavenger and 190 mg of the comparative catalyst C. This gave 7 g of polypropylene copolymer. $M_w$: 95,700 g/mol; $M_w/M_n$: 2.6. $^{13}$C-NMR spectrum: signal intensities: $C^1$: 74.745; $C^5$ and $C^{12}$: 14.393; $C^7$: 6.009; $C^9$ and $C^{10}$: 1.764; $C^6$ and $C^{13}$: 2.591; $C^{15}$ and $C^{16}$: 0.498. This gives an ethylene content of 9.8%.

We claim:

1. A random propylene-ethylene copolymer having
   an ethylene content of from 0.01 to 50% by weight,
   a molar mass $M_w$ (measured using gel permeation chromatography) in the range from 307 000 to 699 000 g/mol,
   an $M_w/M_n$ (measured using gel permeation chromatography) in the range from 1.8 to 4.0,
   a ratio of the intensities of the signal for $C^1$ to the sum of the intensities of the signals for $C^{15}$ and $C^{16}$ (in each case determined from the 13C-NMR spectrum of the random copolymer of the present invention) of more than 100,
   a ratio of the intensities of the signal for $C^7$ to the sum of the intensities of the signals for $C^9$ and $C^{10}$ (in each case determined from the 13C-NMR spectrum of the random copolymer of the present invention) of more than 0.1, and
   a Charpy impact toughness measured in accordance with ISO 179-2/1eU of more than 200 kJ/m$^2$ at 23° C., and of more than 20 kJ/m$^2$ at −20° C.

2. The random propylene-ethylene copolymer claimed in claim 1 having a minimum content of 2,1 insertions (measured using 13C-NMR spectroscopy) of propene monomers ((intra-chain) reverse insertions) of at least four (intra-chain) reverse insertions per polymer chain.

3. The random propylene-ethylene copolymer claimed in claim 1 having a difference in ethylene content between copolymer fractions of differing molar masses of not more than 10% by weight (determined by TREE as described in the experimental section).

4. The random propylene-ethylene copolymer claimed in claim 1 having TREF elution characteristics (as described in the experimental section) such that from 80 to 100% by weight of the copolymer are eluted within a temperature interval extending from 15° C. below to 15° C. above the peak temperature, namely the temperature at which maximum elution occurs.

5. The random propylene-ethylene copolymer claimed in claim 1 obtained by reacting propylene with ethylene, wherein the polymerization is carried out in the presence of a catalyst system comprising at least one cocatalyst and at least one metallocene of the formula (I)

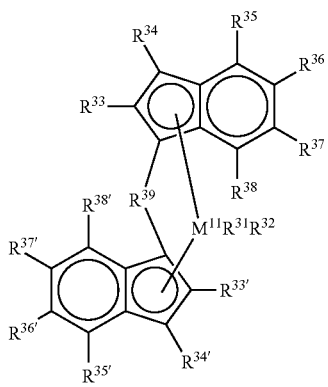

(I)

where $M^{11}$ is a metal of group IVb of the Periodic Table of the Elements, $R^{31}$, $R^{32}$ are identical or different and are each a hydrogen atom, a $C_1$-$C_{10}$-alkyl group, a $C_1$-$C_{10}$-alkoxy group, a $C_6$-$C_{20}$-aryl group, a $C_6$-$C_{20}$-aryloxy group, a $C_2$-$C_{10}$-alkenyl group, an OH group, an $N(R^{32\,a})_2$ group, where $R^{32\,a}$ is a $C_1$-$C_{10}$-alkyl group or a $C_6$-$C_{14}$-aryl group, or a halogen atom, where $R^{31}$ and $R^{32}$ can also be joined to form a ring, $R^{34}$, $R^{36}$, $R^{37}$ and $R^{38}$ and also $R^{34'}$, $R^{36'}$, $R^{37'}$ and $R^{38'}$ are identical or different and are each a hydrogen atom or a hydrocarbon group which may be halogenated, linear, cyclic or branched, $R^{33}$ is a hydrocarbon group which is unbranched in the α position and may be halogenated, $R^{33'}$ is a hydrocarbon group which is cyclized in the α position or branched in the α position and may be halogenated, $R^{35}$, $R^{35'}$ are identical or different and are each a $C_6$-$C_{20}$-aryl group which in the para position relative to the point of linkage to the indenyl ring bears a substituent $R^{43}$ or $R^{43'}$, or

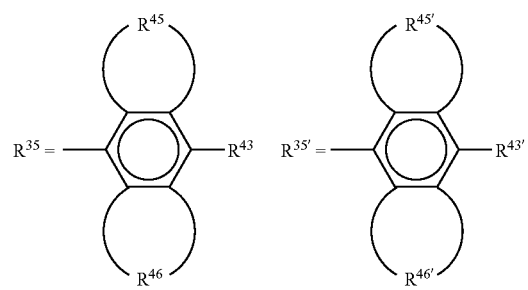

with the proviso that $R^{35}$ and $R^{35'}$ may not be the combinations of phenyl and 1-naphthyl or 1-naphthyl and phenyl when $R^{33}$ is methyl or ethyl and $R^{33'}$ is isopropyl, $R^{39}$ is a bridge

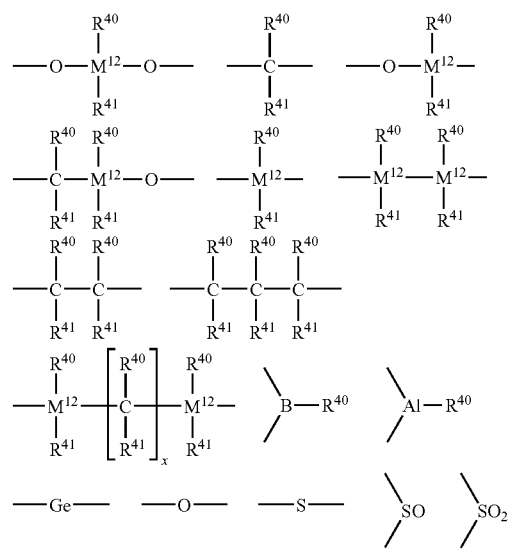

-continued

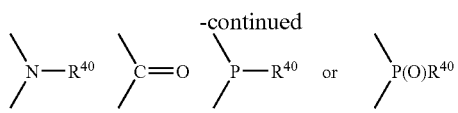

where $R^{40}$, $R^{41}$ can be identical or different, even when they have the same index, and are each a hydrogen atom, a halogen atom or a $C_1$-$C_{40}$ group, where $R^{40}$ and $R^{41}$ may each, together with the atoms connecting them, form one or more rings, x is an integer from zero to 18, $M^{12}$ is silicon, germanium or tin, and $R^{39}$ may also link two units of the formula I with one another, $R^{43}$ can be a hydrogen atom if $R^{35}$ is different from $R^{35'}$, or is a $C_1$-$C_{20}$-alkyl radical, a $C_2$-$C_{10}$-alkenyl radical, a $C_6$-$C_{18}$-aryl radical, a $C_7$-$C_{20}$-arylalkenyl radical, a $C_7$-$C_{20}$-alkylaryl radical, a $C_8$-$C_{20}$-arylalkenyl radical, where the hydrocarbon radicals may also be halogenated or partially halogenated by fluorine or chlorine, —N($R^{44}$)$_2$, —P($R^{44}$)$_2$, —S$R^{44}$, —Si($R^{44}$)$_3$, —[N($R^{44}$)$_3$]$^+$ or —[P($R^{44}$)$_3$]$^+$, where the radicals $R^{44}$ are identical or different and are each a hydrogen atom or a hydrocarbon group which may be halogenated, linear, cyclic or branched, $R^{43'}$ is hydrogen or is as defined for $R^{43}$, $R^{45}$, $R^{45'}$, $R^{46}$ and $R^{46'}$ are each $C_4$-$C_{20}$-aryl, alkenyl or alkyl ring systems which may also be linked to the radicals $R^{36}$, $R^{36'}$ or $R^{34}$, $R^{34'}$.

6. A propylene copolymer having a molar mass $M_w$ (measured using gel permeation chromatography) in the range from 307 000 to 699 000 g/mol, a Charpy impact toughness measured in accordance with ISO 179-2/1eU of more than 200 kJ/m² at 23° C., and of more than 20 kJ/m² at −20° C., and being obtained by reacting propylene with at least one further olefin, wherein the polymerization is carried out in the presence of a catalyst system comprising at least one cocatalyst and at least one metallocene of the formula (I)

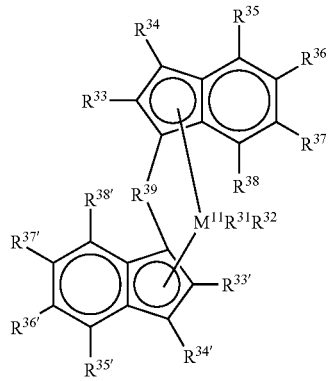

(I)

where $M^{11}$ is a metal of group IVb of the Periodic Table of the Elements, $R^{31}$, $R^{32}$ are identical or different and are each a hydrogen atom, a $C_1$-$C_{10}$-alkyl group, a $C_1$-$C_{10}$-alkoxy group, a $C_6$-$C_{20}$-aryl group, a $C_6$-$C_{20}$-aryloxy group, a $C_2$-$C_{10}$-alkenyl group, an OH group, an N($R^{32a}$)$_2$ group, where $R^{32a}$ is a $C_1$-$C_{10}$-alkyl group or a $C_6$-$C_{14}$-aryl group, or a halogen atom, where $R^{31}$ and $R^{32}$ can also be joined to form a ring, $R^{34}$, $R^{36}$, $R^{37}$ and $R^{38}$ and also $R^{34'}$, $R^{36'}$, $R^{37'}$ and $R^{38'}$ are identical or different and are each a hydrogen atom or a hydrocarbon group which may be halogenated, linear, cyclic or branched, $R^{33}$ is a hydrocarbon group which is unbranched in the α position and may be halogenated, $R^{33'}$ is a hydrocarbon group which is cyclized in the α position or branched in the α position and may be halogenated, $R^{35}$, $R^{35'}$ are identical or different and are each a $C_6$-$C_{20}$-aryl group which in the para position relative to the point of linkage to the indenyl ring bears a substituent $R^{43}$ or $R^{43'}$, or

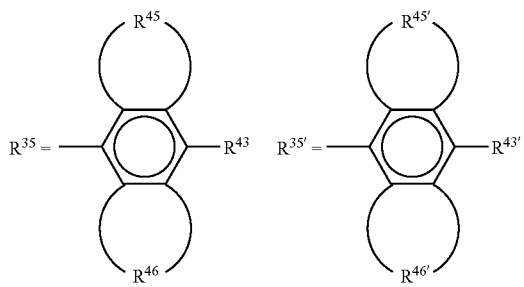

with the proviso that $R^{35}$ and $R^{35'}$ may not be the combinations of phenyl and 1-naphthyl or 1-naphthyl and phenyl when $R^{33}$ is methyl or ethyl and $R^{33'}$ is isopropyl, $R^{39}$ is a bridge

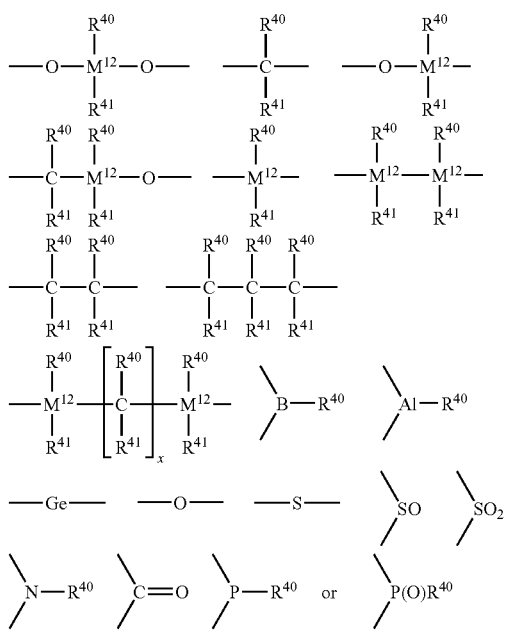

where $R^{40}$, $R^{41}$ can be identical or different, even when they have the same index, and are each a hydrogen atom, a halogen atom or a $C_1$-$C_{40}$ group, where $R^{40}$ and $R^{41}$ may each, together with the atoms connecting them, form one or more rings, x is an integer from zero to 18, $M^{12}$ is silicon, germanium or tin, and $R^{39}$ may also link two units of the formula I with one another, $R^{43}$ can be a hydrogen atom if $R^{35}$ is different from $R^{35'}$, or is a $C_1$-$C_{20}$-alkyl radical, a $C_2$-$C_{10}$-alkenyl radical, a $C_6$-$C_{18}$-aryl radical, a $C_7$-$C_{20}$-arylalkyl radical, a $C_7$-$C_{20}$-alkylaryl radical, a $C_8$-$C_{20}$-arylalkenyl radical, where the hydrocarbon radicals may also be halogenated or partially halogenated by fluorine or chlorine, —N(R$^{44}$)$_2$, —P(R$^{44}$)$_2$, —SR$^{44}$, —Si (R $^{44}$)$_3$, —[N(R$^{44}$)$_3$]$^+$ or —[P(R$^{44}$)$_3$]$^+$, where the radicals $R^{44}$ are identical or different and are each a hydrogen atom or a hydrocarbon group which may be halogenated, linear, cyclic or branched, $R^{43'}$ is hydrogen or is as defined for $R^{43}$, $R^{45}$, $R^{45'}$, $R^{46}$ and $R^{46'}$ are each $C_4$-$C_{20}$-aryl, alkenyl or alkyl ring systems which may also be linked to the radicals $R^{36}$, $R^{36'}$ or $R^{34}$, $R^{34'}$.

7. A random propylene copolymer as claimed in claim 6.

8. The random propylene copolymer claimed in claim 7 wherein from 80 to 100% by weight of this polymer is eluted in TREF analysis within a temperature interval extending from 15° C. below to 15° C. above the temperature at which maximum elution occurs.

9. The random propylene copolymer claimed in claim 7 having at least four reverse insertions per polymer chain.

10. An impact propylene copolymer as claimed in claim 6.

11. The impact propylene copolymer claimed in claim 10 comprising homopolymers and/or random copolymers of propylene wherein from 80 to 100% by weight of this polymer is eluted in TREF analysis within a temperature interval extending from 15° C. below to 15° C. above the temperature at which maximum elution occurs.

12. The impact propylene copolymer claimed in claim 10 comprising a propylene homopolymer or a random copolymer of propylene with from 0.001 to 15% by weight of other 1-alkenes having up to 8 carbon atoms and a propylene-ethylene copolymer having an ethylene content of from 15 to 80% by weight, where the propylene-ethylene copolymer may further comprise additional $C_4$-$C_8$-alk-l-enes, and the propylene-ethylene copolymer which may further comprise additional $C_4$-$C_8$-alk-1-enes is present in a proportion of from 3 to 60% by weight, wherein the propylene-ethylene copolymer which may further comprise additional $C_4$-$C_8$-alk-1-enes has at least four (intra-chain) reverse insertions per polymer chain.

13. The random propylene-ethylene copolymer claimed in claim 1, wherein the ethylene content is at least 3.2% by weight.

14. The random propylene-ethylene copolymer claimed in claim 1, wherein the ethylene content is at least 5.8% by weight.

15. The random propylene-ethylene copolymer claimed in claim 5, wherein the ethylene content is at least 3.2% by weight.

16. The random propylene-ethylene copolymer claimed in claim 5, wherein the ethylene content is at least 5.8% by weight.

* * * * *

UNITED STATES PATENT AND TRADEMARK OFFICE
CERTIFICATE OF CORRECTION

PATENT NO. : 7,569,651 B2  Page 1 of 1
APPLICATION NO. : 11/131251
DATED : August 4, 2009
INVENTOR(S) : Schottek et al.

It is certified that error appears in the above-identified patent and that said Letters Patent is hereby corrected as shown below:

On the title page, item (75), line 2:
   "Soeyer" should read --Speyer--
In Claim 3, col. 71, indicated line 35:
   "TREE" should read --TREF--
In Claim 5, col. 73, indicated line 21:
   "$C_7$-.$C_{20}$-alkylaryl" should read --$C_7$-$C_{20}$-alkylaryl--
In Claim 5, col. 73, indicated line 29:
   a line break should occur between "... defined for $R^{43}$," and "$R^{45}$, $R^{45'}$, $R^{46}$ and ..."
In Claim 6, col. 75, indicated line 12:
   "-Si (R $^{44}$)$_3$," should read -- -Si($R^{44}$)$_3$,--
In Claim 6, col, 75, indicated line 17:
   a line break should occur between "... defined for $R^{43}$," and "$R^{45}$, $R^{45'}$, $R^{46}$ and ..."

Signed and Sealed this

Eighth Day of September, 2009

David J. Kappos
*Director of the United States Patent and Trademark Office*